US005955279A

United States Patent [19]
Gatti et al.

[11] Patent Number: 5,955,279
[45] Date of Patent: Sep. 21, 1999

[54] ATAXIA-TELANGIECTASIA: MUTATIONS IN THE ATM GENE

[76] Inventors: Richard A. Gatti, 3835 Longridge Ave., Sherman Oaks, Calif. 91243; Patrick J. Concannon, 5335 old Mill Rd. NE., Bainbridge Island, Wash. 98110

[21] Appl. No.: 08/874,266

[22] Filed: Jun. 13, 1997

Related U.S. Application Data

[60] Provisional application No. 60/020,079, Jun. 13, 1996.

[51] Int. Cl.⁶ .............................. C12Q 1/68; C12P 19/34; C07H 21/04
[52] U.S. Cl. ........................ 435/6; 435/91.2; 435/172.1; 536/23.1; 536/23.5; 536/24.31; 536/24.33
[58] Field of Search .............................. 435/6, 91.1, 91.2, 435/172.1, 366, 320.1; 536/23.1, 23.5, 24.31, 24.33

[56] References Cited

U.S. PATENT DOCUMENTS

| | | | |
|---|---|---|---|
| 5,225,546 | 7/1993 | Dryja et al. | 536/24.31 |
| 5,380,645 | 1/1995 | Vogelstein | 435/6 |
| 5,382,510 | 1/1995 | Levine et al. | 435/6 |
| 5,407,796 | 4/1995 | Cutting et al. | 435/6 |
| 5,728,807 | 3/1998 | Shiloh et al. | 530/350 |
| 5,756,288 | 5/1998 | Shiloh | 435/6 |

FOREIGN PATENT DOCUMENTS

| | | |
|---|---|---|
| WO 94/00572 | 1/1994 | WIPO . |
| WO 96/36691 | 11/1996 | WIPO . |
| WO 96/36695 | 11/1996 | WIPO . |

OTHER PUBLICATIONS

Science, Vo. 268, Jun. 23, 1995, A Single Ataxia Telangiectasia Gene with a Product Similar to Pl–3 Kinase, pp. 1749–1753, XP–002061971.
Human Molecular Genetics, 1996, Vo. 5, No. 1, 145–149, Mutations revealed by sequencing the 5' half of the gene for ataxia telangiectasia, P.J. Byrd, et al., XP–002061972.
Human Molecular Genetics, 1996, Vo. , No. 4, 433–439, Predominance of null mutations in ataxia–telangiectasia, Shlomit Gilad et al., CP–002061973.
Human Molecular Genetics, 1995, Vo. 4, No. 11 2025–2032, The Complete sequence of the coding region of the ATM gene reveals similarity to cell cycle regulators in different species, Kinneret Savitsky, et al. XP–002061974.
American Journal of Human Genetics, 57:103–111, 1995, Sublocalization of an Ataxia–Telangiectasia Gene Distal to D11S384 by Ancestral Haplotyping in Costra Rican Families, Nancy Uhrhammer, et al., XP–002061975.
Human Molecular Genetics, 1993, Vo. 2, No. 10, 1719–1721, Protein truncation test (PTT) for rapid detection of translation–terminating mutations, Pauline A.M. Roest, et al. XP–002061976.
European Journal of Human Genetics, P.D. Dec. 2, 1991, p. 1955, Linkage analyses with 11q23 markers in Norwegian AT families, Berresen, A.L. et al. XP–002061977.
Genomics 33, 317–320 (1996), Genomic Organization of the ATM Gene, Tamar Uziel, et al. XP–002061978.

European Journal of Human Genetics, 1996, 4:352–355, Exon–Scanning Mutation Analysis of the ATM Gene in Patients with Ataxia–Telangiectasia, XP–002061979.
American Journal of Human Genetics, 59:40–44, 1996, Ataxia–Telangiectasia: Mutation in ATM cDNA Detected by Protein–Truncation Screening, Milhan Telatar, et al., XP–002061980.
American Journal of Human Genetics, 59:320–330, 1996, Mutations Associated with Variant Phenotypes in Ataxia–Telangiectasia, Carmel M. McConville, et al., XP–002061981.
American Journal of Human Genetics, 59:839–846, 1996, A High Frequency of DistincT ATM Gene Mutations in Ataxia–Telangiectasia, Jocyndra Wright, et al., XP–002061982.
American Journal of Human Genetics, 62:86–97, 1998, Ataxia–Telangiectasia: Identification and Detection of Founder–Effect Mutations in the ATM Gene in Ethnic Populations, Milhan Telatar, et al., XP–002061983.
Rojanasakul, Antisense Oligonucleotide Therapeutics: Drug Delivery and Targeting, Advanced Drug Delivery Reviews 18 (1996) 115–131, 1996.
Athma, P., et al. (1996) Molecular genotyping shows that ataxia–telangiectasia heterozygotes are predisposed to breast cancer. Cancer Cenet Cytogenet 92:130–134.
Baumer, A., et al. (1996) New mutations in the ataxia telangiectasia gene. Hum Genet 98:246–249.
Beamish, H., et al. (1994) Radiosensitivity in ataxia–telangiectasia: anomalies in radiation–induced cell cycle delay. Int. J. Radiat. Biol. 65(2):175–184.
Boder, E., et al. (1958) Ataxia–Telangiectasia. Pediatrics 21:526–554.
Boice, J., et al. (1977) Breast cancer in women after repeated fluoroscopic examinations of the chest. J. Natl. Cancer Inst. 59(3):823–832.
Boice, J., et al. (1978) Estimation of breast doses and breast cancer risk associated with repeated fluoroscopic chest examinations of women with tuberculosis. Radiation Research 73:373–390.
Bootsma, D., et al. (1995) Nucleotide excision repair syndrome: molecular basis and clinical symptoms. Phil. Trans. R. Soc. Lond.B 347:75–81.
Borresen, A., et al. (1990) Breast Cancer and other cancers in norwegian families with ataxia–telangiectasia. Genes, Chromosomes & Cancer 2:339–340.
Byrd, P.J., et al. (1996) Mutations revealed by sequencing the 5' half of the gene for ataxia telangiectasia. Human Molecular Genetics 5(1): 145–149.
Chomczynski, P., et al. (1987) Single–step method of RNA isolation by acid guanidinium thiocyanate–phenol–chloroform extraction. Analytical Biochemistry 162:156–159.

(List continued on next page.)

*Primary Examiner*—John L. LeGuyader
*Assistant Examiner*—Mark L. Shibuya
*Attorney, Agent, or Firm*—Knobbe, Martens, Olson & Bear, LLP

[57] ABSTRACT

The invention is related to ataxia-telangiectasia, specifically, mutations in the ataxia-telangiectasia mutated gene.

108 Claims, 13 Drawing Sheets

OTHER PUBLICATIONS

Cortessis, V., et al., (1993) Linkage analysis of DRD2, a marker linked to the ataxia–telangiectasia gene, in 64 families with premenopausal bilateral breast cancer, Cancer Research 53:5083–5086.

Curry, C., et al. (1989) ATfresno: a phenotype linking ataxia–telangiectasia with the nijmegen breakage syndrome. Am. J. Hum. Genet. 45:270–275.

Easton, D.F. (1994) Cancer risks in A–T heterozygotes. Int. J. Radiat. Biol. 66(6):S177–S182.

Ganguly, A., et al. (1993) Conformation–sensitive gel electrophoresis for rapid detection of single–base differences in double–stranded PCR products and DNA fragments . . . Proc. Natl. Acad. Sci. 90:10325–10329.

Gatti, R., et al. (1991) Ataxia–telangiectasia: an interdisciplinary approach to pathogenesis. Medicine 70(2):99–117.

Gatti, R., et al. (1988) Localization of an ataxia–telangiectasia gene to chromosome 11q22–23. Nature 336:577–580.

Gatti, R., et al. (1994) Genetic haplotyping of ataxia–telangiectasia families localizes the major gene to an 850 kb region on chromosome 11q23.1. Int. J. Radiat. Biol. 66(6):S57–S62.

Gilad, S., et al. (1996) Ataxia–telangiectasia: founder effect among north african jews. Human Molecular Genetics 5(12):2033–2037.

Gilad, S., et al. (1996) Predominance of null mutations in ataxia–telangiectasia. Human Molecular Genetics 5(4):433–439.

Hari, K., et al. (1995) The mei–41 gene of D. melanogaster is a structural and functional homolog of the human ataxia telangiectasia gene. Cell 82:815–821.

Hawkins, J.D. (1991) Gene Structure and Expression, 2d ed. Cambridge University Press, Cambridge, pp. 98–134.

Hogervorst, F., et al. (1995) Rapid detection of BRCA1 mutations by the protein truncation test. Nature Genetics 10:208–212.

Huo, Y., et al. (1994) Radiosensitivity of ataxia–telangiectasia, X–linked agammaglobulinemia, and related syndromes using a modified colony survival assay. Cancer Research 54:2544–2547.

Jaspers, N., et al. (1988) Genetic complementation analysis of ataxia telangiectasia and nijmegen breakage syndrome: a survey of 50 patients. Cytogenet Cell Genet 49:259–263.

Keegan, K., et al. (1996) The Atr and Atm protein kinases associate with difference sites along meiotically pairing chromosomes. Genes & Development 10:2423–2437.

Keith, C., et al. (1995) PIK–related kinases: DNA repair, recombination, and cell cycle checkpoints. Science 270:50–51.

Lange, E., et al. (1995) Localization of an ataxia–telangiectasia gene to an 500–kb interval on chromosome 11q23.1: linkage analysis of 176 families by an international consortium. Am. J. Hum. Genet. 57:112–119.

Lavin, M., et al. (1995) Relationship of the ataxia–telangiectasia protein ATM to phosphoinositide 3–kinase. TIBS 20:382–383.

Lehmann, A., et al. (1995) The ataxia–telangiectasia gene: a link between checkpoint controls, neurodegeneration and cancer. TIG 11(10):375–377.

Lehmann, A.R., et al. (1986) A derivative of an ataxia–telangiectasia (A–T) cell line with normal radiosensitivity but A–T–like inhibition of DNA synthesis. Int. J. Radiat. Biol. 49(4):639–643.

Liu, Q., et al. (1995) Restriction endonuclease fingerprinting (REF): a sensitive method for screening mutations in long, contiguous segments of DNA. BioTechniques 18(3):470–477.

McConville, C., et al. (1996) Mutations associated with variant phenotypes in ataxia–telangiectasia. Am. J. Hum. Genet. 59:320–330.

Meyn, S. (1990) Marked elevation of intrachromosomal mitotic recombination: a new facet of the ataxia telangiectasia phenotype. Cancer Genetics A13 12.9.

Meyn, S. (1993) high spontaneous intrachromosomal recombination rates in ataxia–telangiectasia. Science 260:1327–1330.

Meyn, S. (1995) Ataxia–telangiectasia and cellular responses to DNA damage. Cancer Research 55:5991–6001.

Morrow, D., et al. (1995) TEL1, an *S. cerevisiae* homolog of the human gene mutated in ataxia telangiectasia, is functionally related to the yeast checkpoint gene MEC1. Cell 82:831–840.

Mulligan, R., et al. (1993) The basic science of gene therapy. Science 260:926–932.

Nabel, G., et al. (1993) Direct gene transfer with DNA–liposome complexes in melanoma: expression, biologic activity, and lack of toxicity in humans. Proc. Natl. Acad. Sci. 90:11307–11311.

Orita, M., et al. (1989) Rapid and sensitive detection of point mutations and DNA polymorphisms using the polymerase chain reaction. Genomics 5:874–879.

Nowak, R. (1995) Discovery of AT gene sparks biomedical research bonanza. Science 268:1700–1701.

Painter, R. (1985) Ataxia–telangiectasia: genetics, neuropathology, and immunology of a degenerative disease of childhood. (RA Gatti and M Swift, eds.) Alan R. Liss, Inc. New York, pp. 89–100.

Painter, R. (1986) Inhibition of mammalian cell DNA synthesis by ionizing radiation. Int. J. Radiat. Biol. 49(5):771–781.

Painter, R. (1993) Ataxia–telangiectasia. NATO ASI Series. (RA Gatti and RB Painter, Eds.) Springer–Verlag, Heidelberg, pp. 257–268.

Paterson, M., et al. (1979) Enhanced radiosensitivity of cultured fibroblasts from ataxia telangiectasia heterozygotes manifested by defective colony–forming ability and reduced DNA . . . Cancer Research 39:3725–3734.

Pippard, E., et al. (1988) Cancer in homozygotes and heterozygotes of ataxia–telangiectasia and xeroderman pigmentosum in britain. Cancer Research 48:2929–2932.

Rasio, D., et al. (1995) Genomic organization of the ATM locus involved in ataxia–telangiectasia. Cancer Research 55:6053–6057.

Roest, P., et al. (1993) Protein truncation test (PTT) for rapid detection of translation–terminating mutations. Human Molecular Genetics 2(10):1719–1721.

Savitsky, K., et al. (1995) A single ataxia telangiectasia gene with a product similar to PI–3 kinase. Science 268:1749–1753.

Savitsky, K., et al. (1995) The complete sequence of the coding region of the ATM gene reveals similarity to cell cycle regulators in difference species. Human Molecular Genetics 4(11):2025–2032.

Sedgwick, R., et al., (1991) Handbook of clinical neurology vol. 16: Hereditary neuropaties and spinocerebellar atrophies. (JMBV de Jong. Ed.) Elsevier Science Publishers B.V., Amsterdam, pp. 347–423.

Shiloh, Y. (1995) Ataxia–telangiectasia: closer to unraveling the mystery. Eur J. Hum. Genet. 3:116–138.

Snouwaert, J., et al. (1992) An animal model for cystic fibrosis made by gene targeting. Science 257:1083–1088.

Swift, M., et al. (1991) Incidence of cancer in 161 families affected by ataxia–telangiectasia. Cancer Incidence in Families with Ataxia–Telangiectasia 325(26):1831–1836.

Swift, M., et al. (1987) Brast and other cancers in families with ataxia–telangiectasia. The New England Journal of Medicine. 316(21):1289–1294.

Swift, M., et al. (1976) Malignant neoplasms in the families of patients with ataxia–telangiectasia. Cancer Research 36:209–215.

Swift, M., et al. (1986) The incidence and gene frequency of ataxia–telangiectasia in the united states. Am J. Hum. Genet. 39:573–583.

Svedmyr, E., et al. (1975) Possible use of established cell lines for MLR locus typing. Tissue Antigens 5:186–195.

Taylor, A., et al. (1975) Ataxia telangiectasia: a human mutation with abnormal radiation sensitivity. Nature 258:427–429.

Telatar, M., et al. (1996) Ataxia–telangiectasia: mutations in ATM cDNA detected by protein–truncation screening. Am. J. Hum. Genet. 59:40–44.

Tokunaga, M., et al. (1987) Incidence of female breast cancer among atomic bomb survivors, hiroshima and nagasaki, 1950–1980. Radiation Research 112:243–272.

Uhrhammer, N., et al. (1995) Sublocalization of an ataxia–telangiectasia gene distal to DI IS384 by ancestral haplotyping in costa rican families. Am. J. Hum. Genet. 57:103–111.

Uziel, T., et al. (1996) Genomic organization of the ATM gene. Genomics 33:317–320.

Vorechovsky, I., et al. (1996) The ATM gene and susceptibility to breast cancer: analysis of 38 breast tumors reveals no evidence for mutation. Cancer Research 56:2726–2732.

Vorechovsky, I., et al. (1996) ATM mutations in cancer families. Cancer Research 56:4130–4133.

Vorechovsky, I., et al. (1996) Exon–scanning mutation anlysis of the ATM gen in patients with ataxia–telangiectasia. Eur. J. Hum. Genet. 4:352–355.

Weeks, D., et al. (1991) Assessment of chronic γ radiosensitivity as an in vitro assay for heterozygote identification of ataxia–telangiectasia. Radiation Research 128:90–99.

Wooster, R., et al. (1993) Absence of linkage to the ataxia telangiectasia locus in familial breast cancer. Hum. Genet. 92:91–94.

Wright, J., et al. (1996) A high frequency of distinct ATM gene mutations in ataxia–telangiectasia. Am. J. Hum. Genet. 59:839–846.

Xu, Y., et al. (1996) Targeted disruption of ATM leads to growth retardation, chromosomal fragmentation during meiosis, immune defects, and thymic lymphoma. Genes & Development 10:2411–2422.

Xu, Y., et al. (1996) Dual roles of ATM in the cellular response to radiation and in cell growth control. Genes & Development 10:2401–2410.

Young, B., et al. (1989) Radioresistant DNA synthesis and human genetic diseases. Hum. Genet. 82:113–117.

Zakian, V., et al. (1995) ATM–related genes: what do they tell us about functions of the human gene? Cell 82:685–687.

Ziv. Y., et al. (1995) Human cDNA clones that modify radiomimetic sensitivity of ataxia–telangiectasia (group A) cells. Somatic Cell and Molecular Genetics 21(2):99–111.

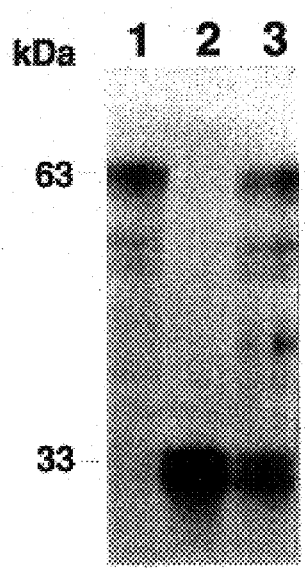 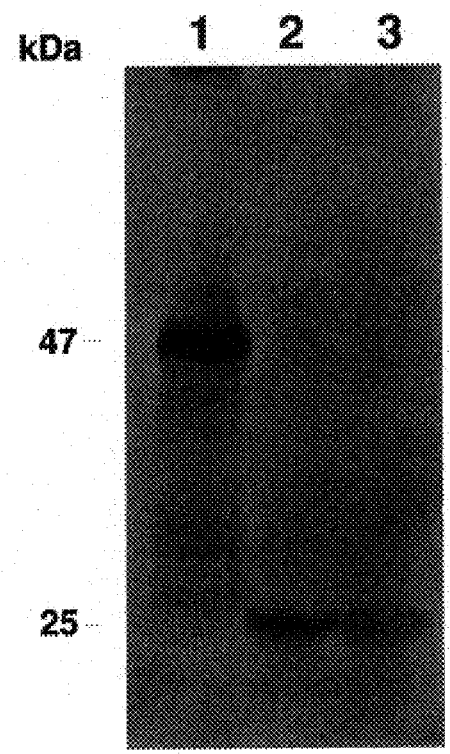
*FIG. 3a*  *FIG. 3b*

| | S1817 | S1819 | NS22 | S2179 | S1294 | S1818 |
|---|---|---|---|---|---|---|
| W9 (top) | 6 | 3 | 1 | 7 | 1 | 2 |
| W9 (bottom) | 6 | 5 | 3 | 9 | 4 | 3 |
| W1 (top) | 7 | 1 | 4 | 9 | 3 | 3 |
| W1 (bottom) | 6 | 3 | 1 | 7 | 2 | 2 |
| W15 (top) | 6 | 7 | 4 | 5 | 1 | 3 |
| W15 (bottom) | 21 | 5 | 4 | 9 | 3 | 3 |
| W24 (top) | 4 | 4 | 2 | 3 | 2 | 3 |
| W24 (bottom) | 4 | 5 | 4 | 9 | 3 | 3 |
| W23 (top) | 21 | 3 | 4 | 11 | 4 | 1 |
| W23 (bottom) | 4 | 5 | 4 | 9 | 3 | 3 |
| W22 (top) | 4 | 5 | 4 | 13 | 3 | 4 |
| W22 (bottom) | 6 | 2 | 3 | 15 | 5 | 2 |
| W6 (top) | 4 | 5 | 4 | 13 | 3 | 6 |
| W6 (bottom) | 20 | 1 | 2 | 11 | 2 | 6 |
| W19 (top) | 6 | 2 | 3 | 9 | 5 | 2 |
| W19 (bottom) | 4 | 5 | 4 | 13 | 4 | 3 |
| W3 (top) | 4 | 3 | 3 | 11 | 2 | 3 |
| W3 (bottom) | 4 | 4 | 6 | 13 | 2 | 6 |
| W10 (top) | 5 | 7 | 4 | 17 | 3 | 3 |
| W10 (bottom) | 4 | 3 | 3 | 11 | 2 | 3 |

ATAXIA-TELANGIECTASIA: MUTATIONS IN THE ATM GENE

This application claims the benifit of U.S. Provisional application No. 60/020,079, filed Jun. 13, 1996.

STATEMENT

This invention was made with Government support under DOE Contract No. DE-FG03-87ER60548. The Government has certain rights in this invention.

FIELD OF THE INVENTION

The field of the invention is ataxia-telangiectasia, specifically, mutations in the ataxia-telangiectasia mutated gene.

BACKGROUND OF THE INVENTION

Ataxia-telangiectasia (AT) is an autosomal recessive disorder characterized by progressive cerebellar ataxia, immunodeficiency, chromosomal instability, cancer susceptibility and radiation sensitivity (Gatti et al., Medicine 70: 99–117, 1991). The disease has a well-defined phenotype, in most cases easily diagnosed and shows complete penetrance. The disease frequency has been estimated at 1/40,000–1/100,000 live births (Swift et al., N Engl J Med 325: 1831–36, 1991). The gene responsible for AT was localized by linkage analysis to within 300 kb at chromosome 11q23.1, using an international consortium of ~200 families (Gatti et al., Nature 336: 577–580, 1988; Gatti et al., Intl J Radiat Biol 66: S57–S62, 1994; Lange et al., Am J Hum Genet 57,112–119, 1995; Uhrhammer et al., Am J Hum Genet 58: 103–111, 1995). Savitsky and workers identified a gene in this region, ATM, encoding a very large protein (~350 kDa), with a transcript of 12 kb and alternative splicing (Savitsky et al., Science 268: 1749–1753, 1995; Savitsky et al., Hum Mol Genet 4: 2025–2032, 1995). ATM stands for ataxia-telangiectasia mutated. The gene shows homology with protein kinases in yeast (TEL-1), Drosophila, and human (DNA-PK) and is most closely related to DNA-PK and TEL-1 (Savitsky et al., Science 268: 1749–1753, 1995; Savitsky et al., Hum Mol Genet 4: 2025–2032, 1995; Lehmann et al., Trends Genet 11: 375–377, 1995; Zakian, Cell 82: 685–687, 1995; Lavin et al., Trends Biol Sci 20: 382–383, 1995; Keith et al., Science 270: 50–51, 1995). SEQ ID NO:1 is the nucleotide sequence encoding the ATM protein, corresponding to GenBank Accession No. U33841. The open reading frame is 9168 nucleotides. There is a 3' untranslated region (UTR), and a 5' UTR. SEQ ID NO:2 is the amino acid sequence of the deduced ATM protein. It has 3056 amino acids. The ATM gene product contains a phosphatidylinositol-3 kinase (PI-3) signature sequence at codons 2855–2875. Mutation analyses in the initial report by Savitsky et al., Science 268: 1749–1753, 1995, used restriction endonuclease fingerprinting (REF) to identify mutations in the reverse-transcribed 5.9 kb carboxy-terminal end, which included the PI-3 signature sequence, of the 10 kb transcript that was available at that time (Savitsky et al., Hum Mol Genet 4: 2025–2032, 1995). Both in-frame and frameshift mutations were found. Because the methodology used for screening for mutations biases the types of mutations found, there is a need to use different screening methods to identify further mutations in the ATM gene.

These and other objects of the invention will be apparent to one of ordinary skill in the art upon consideration of the specification as a whole.

SUMMARY OF THE INVENTION

The invention relates to an isolated and purified fragment comprising nucleic acid having complementarity or identity to a mutation in the ataxia-telangiectasia mutated (ATM) gene, the mutation selected from the group consisting of the mutations in Table 1.

The invention additionally relates to an isolated and purified fragment comprising nucleic acid having complementarity or identity to a mutation in the ataxia-telangiectasia mutated (ATM) gene, the mutation selected from the group consisting of the mutations in Table 2.

The invention further relates to an isolated and purified fragment comprising nucleic acid having complementarity or identity to a mutation in the ataxia-telangiectasia mutated (ATM) gene, the mutation selected from the group consisting of:

3245ATC>TGAT(c1081),
5908delC(c1970),
7449G>A(c2481del70),
7630-2A>C(c2544del159),
6095G>A(c2003del89),
7010delGT(c2337),
5932G>T(c1973del88),
3214G>T(c1026del207),
432insA(c144),
3087insA(c1029),
8766insT(c2922),
7517del4(c2506),
1607G>T(c536ins800),
2493insA(c835),
1563delAG(c522),
4612-12A>G(c1538ins11),
8494C>T(c2832),
8786G>A(c2891del115),
2251-10T>G(c750ins9),
2810insCTAG(c937ins),
7327C>T(c2443), and
7926A>C(c2544del298).

In another embodiment, the invention relates to a method of testing a DNA sample of a human for the presence of a mutation in the ATM gene, comprising:
  providing a sample of DNA from a human, and
  testing the sample for the presence of a mutation in the ATM gene, the mutation selected from the group consisting of the mutations in Table 1.

In yet another embodiment, the invention additionally relates to a method of testing a DNA sample of a human for the presence of a mutation in the ATM gene, comprising:
  providing a sample of DNA from a human, and
  testing the sample for the presence of a mutation in the ATM gene, the mutation selected from the group consisting of the mutations in Table 2.

In still another embodiment, the invention further relates to a method of testing a DNA sample of a human for the presence of a mutation in the ATM gene, comprising:
  providing a sample of DNA from a human, and
  testing the sample for the presence of a mutation in the ATM gene, the mutation selected from the group consisting of:

3245ATC>TGAT(c1081),
5908delC(c1970),
7449G>A(c2481del70),
7630-2A>C(c2544del159),
6095G>A(c2003del89),
7010delGT(c2337),
5932G>T(c1973del88),
3214G>T(c1026del207), 432insA(c144),
3087insA(c1029),
8766insT(c2922),
7517del4(c2506),
1607G>T(c536ins800),
2493insA(c835),
1563delAG(c522),
4612-12A>G(c1538ins11),
8494C>T(c2832),
8786G>A(c2891del115),
2251-10T>G(c750ins9),
2810insCTAG(c937ins),
7327C>T(c2443), and
7926A>C(c2544del298).

In the above method, the mutation may be 3245ATC>TGAT(c1081), and the step of testing may comprise PCR amplifying exon 24 of the gene with primers SEQ ID NO:20 and SEQ ID NO:21 in a sample of DNA from the human to form PCR products and subjecting the PCR products to heteroduplex analysis.

In the above method, the mutation may be 5908delC (c1970), and the step of testing may comprise PCR amplifying exon 41 of the gene with primers SEQ ID NO:22 and SEQ ID NO:23 in a sample of DNA from the human to form PCR products and subjecting the PCR products to restriction enzyme digestion analysis using Sau3A I.

In the above method, the mutation may be 7449G>A (c2481del70).

In the above method, the mutation may be 7630-2A>C (c2544del159), and the step of testing may comprise PCR amplifying exon 54 of the gene with primers SEQ ID NO:32 and SEQ ID NO:33 in a sample of DNA from the human to form PCR products and subjecting the PCR products to restriction enzyme digestion analysis using Alu I.

In the above method, the mutation may be 6095G>A (c2003del89), and the step of testing may comprise PCR amplifying exon 43 of the gene with primers SEQ ID NO:26 and SEQ ID NO:27 in a sample of DNA from the human to form PCR products and subjecting the PCR products to restriction enzyme digestion analysis using Bfa I.

In the above method, the mutation may be 7010delGT (c2337), and the step of testing may comprise PCR amplifying exon 50 of the gene with primers SEQ ID NO:28 and SEQ ID NO:29 in a sample of DNA from the human to form PCR products and subjecting the PCR products to restriction enzyme digestion analysis using Tfi I.

In the above method, the mutation may be 5932G>T (c1973del88), and the step of testing may comprise PCR amplifying exon 42 of the gene with primers SEQ ID NO:24 and SEQ ID NO:25 in a sample of DNA from the human to form PCR products and subjecting the PCR products to restriction enzyme digestion analysis using Mse I.

In the above method, the mutation may be 3214G>T (c1026del207), and the step of testing may comprise PCR amplifying exon 24 of the gene with primers SEQ ID NO:20 and SEQ ID NO:21 in a sample of DNA from the human to form PCR products and subjecting the PCR products to restriction enzyme digestion analysis using Mse I.

In the above method, the mutation may be 432insA(c144).

In the above method, the mutation may be 3087insA (c1029).

In the above method, the mutation may be 8766insT (c2922).

In the above method, the mutation may be 7517del4 (c2506), and the step of testing may comprise PCR amplifying exon 53 of the gene with primers SEQ ID NO:30 and SEQ ID NO:31 in a sample of DNA from the human to form PCR products and subjecting the PCR products to heteroduplex analysis.

In the above method, the mutation may be 1607G>T (c536ins800).

In the above method, the mutation may be 2493insA (c835).

In the above method, the mutation may be 1563delAG (c522), and the step of testing may comprise PCR amplifying exon 12 of the gene with primers SEQ ID NO:18 and SEQ ID NO:19 in a sample of DNA from the human to form PCR products and subjecting the PCR products to heteroduplex analysis.

In the above method, the mutation may be 4612-12A>G (c1538ins11).

In the above method, the mutation may be 8494C>T (c2832).

In the above method, the mutation may be 8786G>A (c2891del115).

In the above method, the mutation may be 2251-10T>G (c750ins9).

In the above method, the mutation may be 2810insCTAG (c937ins).

In the above method, the mutation may be 7327C>T (c2443).

In the above method, the mutation may be 7926A>C (c2544del298).

In another aspect, the invention provides an isolated and purified protein, polypeptide, or peptide encoded by a polynucleotide that comprises any of the above nucleic acid fragments.

In another manifestation, the invention provides an isolated and purified antibody that specifically recognizes any of the above proteins, polypeptides, or peptides.

The invention also features a transgenic mouse all of whose germ cells and somatic cells contain any of the above nucleic acids fragments introduced into the mouse, or an ancestor of the mouse, at an embryonic stage.

BRIEF DESCRIPTION OF THE DRAWINGS

FIG. 3. Protein truncation testing. (a). Norwegian patients: region g. Lane 1 is a normal control, lanes 2 and 3 are patients both showing truncated protein of 33 kDa (one homozygous, the other heterozygous). (b). Costa Rican patients: region b. Lane 1 is a normal control, lanes 2 and 3 are homozygous patients, both showing a truncated protein of 25 kDa.

FIG. 5. Haplotype analysis of 27 Costa Rican patients. Boxes heavily outlined indicate conserved haplotypes. Shaded allele 5 indicates a new allele in haplotype [A].

DETAILED DESCRIPTION OF THE PREFERRED EMBODIMENT

Figure 1:
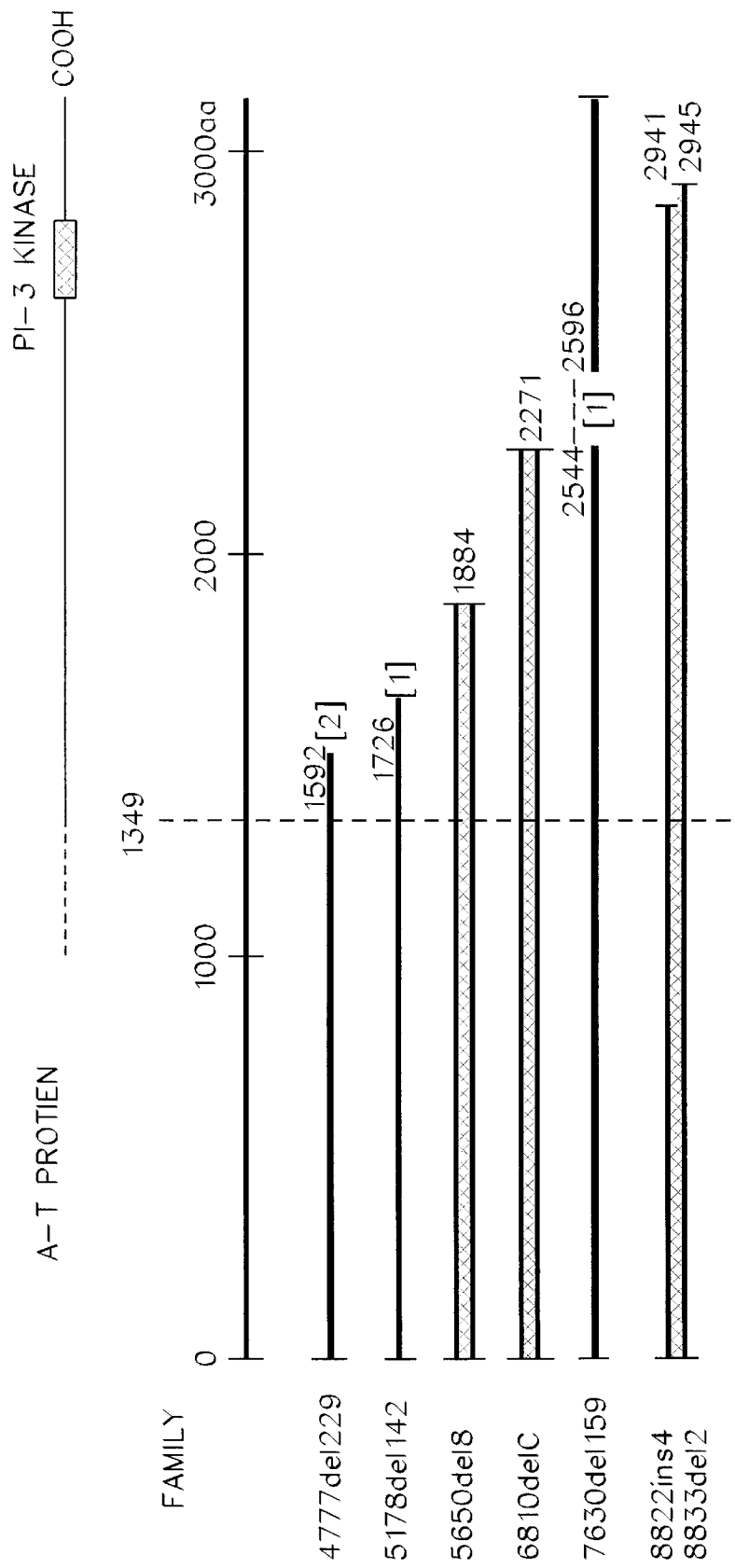
FIG. 1. Schematic diagram of six types of mutations detected by the protein truncation test (PTT). The first missing codon is shown at the truncation site. The numbers in brackets represent skipped exons in the cDNA. Thick shaded bars represent families with homozygous mutations, or both mutations defined.

The ATM sequences and other materials comprising the present invention can advantageously be in isolated form. As used herein, the term "isolated" denotes that the material has been removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated.

It is also advantageous that the sequences and other materials comprising the invention be in purified form. The term "purified" does not require absolute purity; rather, it is intended as a relative definition. Purification of starting material or natural material means that the concentration of the material is at least about 2, 5, 10, 100 or 1000 times its original concentration (for example), advantageously 0.01% by weight, preferably at least about 0.1% by weight. Purified preparations of about 0.5%, 1%, 5%, 10% and 20% by weight are also contemplated.

I. Mutations in ATM cDNA Detected by Protein-Truncation Screening

Mutation analyses in the initial report by Savitsky et al., Science 268: 1749–1753, 1995, used REF to identify mutations in the reverse-transcribed 5.9 kb carboxy-terminal end of the 10 kb transcript that was available at that time (Savitsky et al., Hum Mol Genet 4: 2025–2032, 1995). The protein-truncation test (PTT) has been used successfully for detecting mutations in the DMD and BRCA1 genes (Roest et al., Hum Mol Genet 2: 1719–1721, 1993; Hogervorst et al., Nat Genet 10: 208–212, 1995). This method was chosen for screening patient-derived cDNAs for mutations in the same 5.9 kb fragment. Twenty-one mutations were identified in 48 patients (8 of whom were consanguineous), by using a set of eight primers.

The distal half of the ATM gene transcript was examined for truncation mutations in 48 AT affecteds. Twenty-one mutations were found; four of the mutations were seen in more than one individual. Genotyping of the individuals sharing mutations, using nearby microsatellite markers, established that 3 of the 4 groups shared common haplotypes, indicating that these were probably founder effects, not public mutations. The one public mutation was found in two American families, one of Ashlkenazi Jewish background, the other not. Most truncations deleted the PI-3-kinase domain, although some exceptions to this were found in patients with typical AT phenotypes. All patients not previously known to be consanguineous were found to be compound heterozygotes when mutations could be identified, i.e., showing normal and abnormal protein segments on SDS-PAGE gels. All 48 patients gave RT-PCR products, indicating the presence of relatively stable mRNAs despite their mutations. These results suggest that few public mutations or hot spots can be expected in the ATM gene, and that epidemiological studies of AT carrier status and associated health risks will probably have to be designed around populations with frequent founder effect mutations.

Using reversed-transcribed RNA from 48 AT patients as template and screening in vitro transcribed/translated protein for truncated segments, according to Example 1, the following results were obtained. Primarily small deletions and insertions were detected, none larger than several hundred nucleotides. Base substitutions were also observed leading to nonsense mutations.

Beginning at codon 1349, the transcript was divided into four overlapping regions of ~1200–1550 nucleotides (nt) which were tested for protein truncation. These regions included codons 1349–1805 (region a), 1760–2176 (region b), 2107–2618 (region c), and 2550–3057 (region d). RNA from lymphoblastoid cell lines of AT patients was isolated and reverse transcribed by priming with random hexamers and a poly T primer. It was then amplified with a T7-modified forward primer for each region.

Of twenty-one mutations identified (Table 1), four were shared in nine supposedly unrelated families. However, when "unrelated" was further defined by genotyping these patients with microsatellite markers located within 1 cM of the gene, 3 of the 4 groups shared haplotypes, indicating that three founder effect mutations and one "public" mutation had been defined. The public mutation was C6100T at codon 2034 and was found in two unrelated American families (AT44LA and AT81LA), one being of Ashkenazi Jewish origin. Most patients who are not consanguineous appear to be compound heterozygotes.

In seven of the 21 patients with truncation mutations, the analysis of RT-PCR products on 1% agarose gel showed fragments of smaller size, as well as those of expected size. When the translated protein products of these individuals were analyzed on SDS-PAGE gels, the presence of one normal and one truncated product was confirmed. As shown in Table 1, all seven cases had deletions that skipped regions corresponding to entire exons: 1) AT83LA had one exon of 142 nt deleted; 2) AT65LA and AT93LA had 89 nt deleted, also a single exon; 3) AT71LA had 229 nt deleted, accounting for two adjacent exons; 4) AT6LA had 115 nt deleted, again accounting for a single exon. All of these deletions resulted in frameshifts. 5) In two patients, AT98LA and AT72LA, a mutation (7630del159) was found that, although it deletes an entire exon, remains in-frame (FIG. 1). This was confirmed in an affected sibling. The other 13 patients gave expected (normal) sizes for products on agarose gels but, nonetheless, had truncated protein products by PTT. Sequence analyses showed that these patients were carrying either nonsense mutations or small insertions or deletions that resulted in frameshifts. Only one large deletion (of 85 kb) has been observed thus far in a Palestinian Arab family (Savitsky et al., Hum Mol Genet 4: 2025–2032, 1995).

The intensity of the PTT products on SDS-PAGE autoradiogram was sometimes equal and other times not. Given that both mRNA alleles are mutated in compound heterozygotes and might, therefore, be expected to be unstable, it is surprising that RT-PCR-based mutation screening methods, such as REF, PTT, conformation-sensitive gel electrophoresis (CSGE), and single strand conformational polymorphism (SSCP), have all been generally effective in identifying mutation sites. This may reflect the ability of PCR to detect even small amounts of unstable messages. However, PTT probably does not accurately reflect quantitative differences in mRNA stability.

FIG. 1 depicts the translational effects of the types of mutations observed by PTT. The regions screened cover only the carboxy-terminal 1708 codons of the ATM protein and contain the PI-3 kinase domain. Most of the truncation mutations reported here delete this highly conserved domain. Patients AT76LA(5650de18) and AT48LA (6810delC) are homozygous for their mutations, and their ATM proteins do not have the PI-3 kinase domain. In AT79LA(8822insAACT;8833delCT), a compound heterozygote, both mutations result in truncation of the ATM protein by 111 and 115 amino acids, respectively, conserving the kinase domain. Despite this, the phenotype in these patient includes early onset of a progressive cerebellar ataxia, cerebellar atrophy on magnetic resonance imaging, telangiectasia, radiosensitivity, t(7;14)(p13;q11.2) translocations, elevated alphafetoprotein, frequent infections, and multiple immunological abnormalities. Thus, while it is tempting to speculate that the frequent occurrence of truncation mutations in AT patients suggests that the PI-3 kinase domain at the 3' end of the gene is indispensable, the results for this patient suggest that even more limited 3' end truncations are deleterious and can lead to essentially the same phenotype.

These PTT studies were performed to: 1) identify mutation sites and types so that they could be compared with AT phenotypes, and 2) test the efficiency of PTT for mutation screening within this gene. In-frame mutations, such as those detected by REF, would not be detected by this approach. Some investigative groups are screening for such in-frame mutations by CSGE. On the other hand, it should be noted that some DNA changes detected by REF or CSGE may represent polymorphisms and not the defect causing the disease, whereas changes that result in protein truncation are almost certain to represent true mutations. This is believed to be the first attempt at applying PTT to mutation analysis of the ATM gene.

Characterizing the worldwide spectrum of ATM mutations should now enable the epidemiological observations of others suggesting high cancer risk in AT heterozygotes, to be critically evaluated. If AT carrier females are at a five-fold increased risk of breast cancer, ATM could play an important role in the etiology of breast cancer. When the mutation results presented here are considered together with those of others it appears that public mutations are rare, and hot spots will also be uncommon. Thus, in order to screen a cadre of breast cancer patients for ATM mutations, it might be necessary either to use populations related by founder effects, such as Costa Rica (Uhrhammer et al., Am J Hum Genet 58: 103–111, 1995) or to screen the entire gene for a single mutation in each cancer patient.

TABLE 1

AT MUTATIONS (listed by codon position)*

| Family | Ethnicity** | Mutation | Codon | Protein |
|---|---|---|---|---|
| AT71LA | Polish | 4777de1229 | 1592 | truncated |
| AT83LA[X] | U.S. | 5178de1142 | 1726 | truncated |
| AT76LA[X] | Bolivian$ | 5650de18 | 1884 | truncated |
| AT65LA[X] | Polish*** | 6007de189 | 2003 | truncated |
| AT93LA[X] | Polish*** | | | |
| AT14LA | U.S. | 6015insC | 2005 | truncated |
| AT81LA | Ashkenazi | C6100T | 2034 | truncated |
| AT44LA | U.S. | | | |
| AT30LA | U.S. | 6372insG | 2124 | truncated |
| GM1524 | U.K. | 6404insTT | 2135 | truncated |
| AT48LA | Italian$ | 6810delC | 2271 | truncated |
| AT66LA | Polish | 7009delTG | 2337 | truncated |
| AT98LA[X] | Polish*** | 7630del159 | 2544 | truncated |
| AT72LA | Polish*** | | | |
| GHAT | Australian*** | A8266T | 2756 | truncated |
| GM3189 | U.S.*** | | | |
| AT41LA | Irish*** | | | |
| AT6LA | U.S. | 8672del115 | 2891 | truncated |
| AT79LA | Italian | 8822insAACT | 2941 | truncated |
| AT79LA | Italian | 8833de1CT | 2945 | truncated |
| AT34LA | Hispanic | 8985de113 | 2995 | truncated |

*Numbering of nucleotides is based on the full sequence of the ATM gene, with the first nucleotide of the initiating ATG codon considered to be "1."
**In some U.S. families with only one allele defined, ethnicity has been stated if both parents were of the same ethnic background. Others have been purposely left vague until the ethnic origin of each allele can be definitively traced.
***Persons sharing a mutation and a haplotype, i.e., a founder effect.
[X]Sibling had same mutation.
$Homozygotes by consanguinity, confirmed by genotyping, PTT data, and sequencing.

II. A High Frequency of Distinct ATM Gene Mutations in Ataxia-Telangiectasia

The clinical features of the autosomal recessive disorder ataxia-telangiectasia include a progressive cerebellar ataxia, hypersensitivity to ionizing radiation, and an increased susceptibility to malignancies. Epidemiological studies have suggested that AT heterozygotes may also be at increased risk for malignancy, possibly as a consequence of radiation exposure. A gene mutated in AT patients (ATM) has recently been isolated, making mutation screening in both patients and the general population possible. Because of the relatively large size of the ATM gene, the design of screening programs will depend on the types and distribution of mutations in the general population. As a result of the experiments described in Example 2, 30 mutations were identified in a panel of unrelated AT patients and controls. Twenty-five of the 30 were distinct, and most patients were compound heterozygotes. The most frequently detected mutation was found in three different families and had previously been reported in five others. This corresponds to a frequency of 8% of all reported ATM mutations. Twenty-two of the alterations observed would be predicted to lead to protein truncation at sites scattered throughout the molecule. Two fibroblast cell lines, which displayed normal responses to ionizing radiation, also proved to be heterozygous for truncation mutations of ATM.

Sequence Variation in the ATM Gene

A panel of PCR primers were synthesized that would amplify overlapping fragments between 250 and 500 nt, spaced over the length of the initially published sequence (approximately half) of the ATM gene (Savitsky et al., Science 268: 1749–1753, 1995). ATM cDNA was synthesized from each of a panel of 36 lymphoblastoid cell lines derived from unrelated AT patients. Two SV40 transformed fibroblast cell lines derived from donors without a family history of AT were also analyzed. PCR amplification products from the 3' half of the ATM gene from all 38 cell lines were screened for sequence variation by SSCP under two different gel conditions. With the subsequent publication of the nucleotide sequence of the 5' half of the TM gene (Savitsky et al., Hum Mol Genet 4: 2025–2032 1995; Byrd et al., Hum Mol Genet 5: 145–149, 1996), selected samples were also screened for variation in this region. All bands exhibiting aberrant migration on SSCP gels were excised, reamplified, and sequenced on both strands.

With this approach, 30 instances of sequence variation in the ATM gene were detected (Table 2). The sequence alterations observed include nucleotide substitutions (2), insertions (1), and most commonly, deletions (27) of from 2 to 298 nt. The recent publication of the exon-intron structure of the ATM gene (Uziel et al., Genomics 33: 317–320, 1996) allowed many of the deletions to be identified as corresponding to the failure to splice correctly one or two exons. The bias in favor of detection of large deletions may reflect the relatively large sizes of these PCR products for screening by SSCP. However, these deletions were usually of sufficient size to be detected by visual examination of PCR products in agarose gels prior to SSCP analysis.

Twenty-five different variants were represented among the 30 sequence differences observed, and no one variant was detected more than three times. In the cases of two pairs of cell lines where the same alteration to cDNA was detected (AT4SE/1AT2203 and AT7SE/GM11255), genotyping of two markers flanking ATM (D11S1818 and D11S1819) and one marker within the gene (D11S2179) revealed that the cell lines shared no alleles at any marker. This indicates that the losses of exons detected in these samples result from distinct mutations. In the case of AT4SE and 1AT2203, subsequent analysis of genomic DNA provided additional evidence that they harbored distinct mutations, both leading to the incorrect splicing of exon 55.

In virtually all cases where abnormal SSCP pattern was observed, bands corresponding to the normal allele were present, as well. Thus, most AT patients appeared to be compound heterozygotes. The once exception was an Amish patient, AT7LA, from the pedigree originally used to localize the ATM gene (Gatti et al., Nature 336: 577–580, 1988). This patient was homozygous for a 2-nt deletion in codon 521. It is interesting to note that this mutation has also been described in one patient from the United Kingdom (Byrd et al., Hum Mol Genet 5: 145–149, 1996).

In the absence of functional data, it is difficult to determine conclusively whether an observed variation in sequence represents a true mutation. However, 19 of the 25 unique variants observed would be predicted to truncate the ATM protein, in most cases by frameshifting and thus are likely to represent true mutations. The locations of these mutations are broadly distributed throughout the gene. Although there is no obvious clustering of these mutations that might point to critical domains of the ATM protein, it may be significant that the two regions of homology to other genes lie in the 3' half of ATM would thus be affected by the majority of these truncation mutations.

Among variants observed in more than one patient, the most frequent was a 9-nt deletion occurring at codon 2546 in exon 54. It was observed in three unrelated AT families and was confirmed in one family in a second sibling (AT8SE and AT9SE). In all cases, it was also confirmed by amplification from genomic DNA. Genotyping of these families with microsatellite markers flanking and within the ATM gene (D11S1818, D11S1819, and D11S2179) suggested that the mutation was present on at least two distinct haplotypes. Among alterations reported in the ATM gene in AT families to date (Savitsky et al., Science 268: 1749–1753, 1995; Byrd et al., Hum Mol Genet 5: 145–149, 1996; Gilad et al., Hum Mol Genet 5: 433–439, 1996), this is the most frequently observed change (8 of 103 total mutations reported).

The deletion at codon 2546 would be predicted to delete only three amino acids and leave the reading frame intact. It has been argued that it is, indeed, a mutation since one of the amino acids lost is conserved in a *Saccharomyces cerevisiae* homologue of ATM, TEL1 (Morrow et al., Cell 82: 831–840, 1995). However, its modest predicted effect on the protein might also be consistent with a polymorphic allele of ATM. The deletion results in the loss of a unique XbaI restriction site, thus making it possible to assay for the mutation by amplification of genomic DNA and subsequent XbaI digestion of the product. When this assay was performed on the parents of the CEPH gene mapping families (n=75), no examples of the deletion were detected, indicating that this alteration is not a common allele of ATM.

Several of the AT cell lines screened here have been studied previously (Savitsky et al., Science 268: 1749–1753, 1995; Gilad et al., Hum Mol Genet 5: 433–439, 1996). The present study extends these observations by providing the identity of the second mutant allele in compound heterozygous patients. For example, SSCP screening of AT3LA revealed the previously reported splicing defect leading to the loss of exon 55 or both exons 54 and 55. (Savitsky et al., Science 268: 1749–1753, 1995). However, a band corresponding to the normal allele was also present. Further screening of the gene revealed two additional alterations, a conservative substitution (ACA→ATA) at position 2438 and a nonsense substitution (AAG→TAG) at 2443. The nonsense substitution at codon 2443, which would truncate the protein, is a clearly deleterious mutation. In order to determine the relationship between these observed alterations, fragments spanning all of the changes were amplified from cDNA, separated on an SSCP gel, and sequenced. In this analysis, fragments with one or two exons deleted always had the normal sequence at codons 2438 and 2443, indicating that the null mutation and the splicing aberration correspond to different alleles.

Confirmation of Variation in Genomic DNA

All previously published studies of ATM gene variation have relied on cDNA templates because of the relatively large size of the gene to be surveyed. Many of the changes detected, both in this study and in previous ones (Savitsky et al., Science 268: 1749–1753, 1995; Byrd et al., Hum Mol Genet 5: 145–149, 1996; Gilad et al., Hum Mol Genet 5: 433–439, 1996), appear to correspond to splicing errors. In order to confirm results obtained with cDNA as the SSCP template in this study, intronic nucleotide sequences were determined, and primers were designed so that selected samples could be analyzed after amplification from genomic DNA. As indicated in Table 2, the short nucleotide deletions in cDNA from AT7LA, GM08436, AT9SE, AT31LA, and AT8SE and the nucleotide substitutions in exon 52 of GM11261 and exon 58 of AT3ABR were all confirmed.

Putative splicing mutations were examined in AT30LA, GM11261, AT4SE, 1AT2203, ATISE, GM09587, GM11254 and AT13SE. In the case of AT30LA an insertion of a single G residue in exon 46 was detected that would lead to frameshifting and premature termination. A fraction of the cDNA had this exon deleted, presumably allowing the production of a shortened, in-frame transcript, which could still have some partial function. A similar observation was made for 1AT2203, where a single nucleotide substitution creating a stop codon was detected in exon 55. This exon was deleted in cDNA from 1AT2203.

Other observed splicing variants resulted from mutations in conserved residues in and around the splice donor and acceptor sequences (Table 2). Perhaps the most interesting was detected in GM11261, which, in both this study and that of Savitsky et al., Science 268: 1749–1753, 1995, displayed a complex splicing pattern in which either exon 55 alone or both exons 54 and 55 were deleted. Genomic nucleotide sequence analysis of exons 54 and 55 and their flanking and intervening introns revealed that penultimate nucleotide of exon 55 was altered (A→C). In eukaryotic exons, this residue is most often A (60%) and least often C (12%) (Hawkins, *Gene Structure and Expression*, 2d ed. Cambridge University Press, Cambridge, pp. 98–134, 1991). Further, exon 55 of ATM already has another nonstandard residue, A, at the adjacent last position of the exon, which in most eukaryotic exons is G (79%) (Hawkins, *Gene Structure and Expression* 2d ed. Cambridge University Press, Cambridge, pp. 98–134, 1991). Thus, this combination of mutated and nonstandard residues at the splice junction likely reduces the match to optimal splicing sequences to such a level that frequent aberrant splicing events are observed.

GM11261 was only one of three cell lines in which deletion of exon 55 was detected in cDNA. Genomic analysis of the other two cell lines, AT4SE and 1AT2203, revealed that each of the three cell lines had a distinct mutation that affected splicing of this exon. A similar analysis of GM09587 and AT1SE, each of which delete exon 59 in cDNA, revealed that they shared a mutation at the 3' splice donor site of exon 59.

Complementation Groups

The finding that a single gene is mutated in AT cell lines derived from different complementation groups raises questions as to why complementation is observed in cell-fusion experiments. Several of the cell lines studied here have been fused with each other (or with cell lines from siblings) in complementation experiments. For example, AT8LA and AT9LA, which are derived from members of the same family as AT7LA, were previously shown to complement AT3LA in cell-fusion experiments (Jaspers et al., Cytogenet Cell Genet, 49: 259–263 1988). As described above, both alleles in AT3LA and AT7LA contain mutations that would truncate the ATM protein before the P1-3 kinase homology region. Thus, a heterokaryon of these cell lines would not be predicted to make an intact ATM protein even allowing for intragenic complementation. By present understanding, these results are inconsistent with the assignments of those cells to different complementation groups.

AT Heterozygotes

Two fibroblast cell lines not derived from AT patients or their families, GM00637 and LM217, were screened by SSCP for mutations across the entire ATM cDNA sequence. Both GM00637 and LM217 have been used frequently as normal controls in radiation biology experiments, and their responses to radiation are well characterized (e.g., Lehmann et al., Int J Radiat Biol 49: 639–643, 1986; Ziv et al., Somat Cell Mol Genet 21: 99–111 1995). Despite their apparently normal radiation phenotypes, aberrant splicing products were detected in both LM217 and GM00637, which would be predicted to truncate the ATM protein. In the case of GM00637, the observed alteration corresponded to the loss of two exons and was not detected in any other cell line screened. In LM217, an aberrantly migrating SSCP band containing a deletion of the first 19 nt of exon 17 was detected. This alteration was also observed in an AT cell line GM02782 (Table 2). The last 5 nt of the deleted region, TGCAG, conforms to the consensus sequence for a 3' splice acceptor, YNCAG, suggesting that it may be serving as a cryptic splice-acceptor sequence. Nucleotide sequencing of the normal and variant SSCP bands derived from LM217 cDNA revealed that the final nucleotide of exon 16 was, in both cases, a G rather than the C reported for the ATM sequence (Savitsky et al., Hum Mol Genet 4: 2025–2032 1995; Uziel et al., Genomics 33: 317–320, 1996). While this change may be responsible for the observed alteration in splicing, its observation in both normal and mutant SSCP products, along with the 250-fold greater preference for G as opposed to C at the −1 position of 5' splice donors (Hawkins, *Gene Structure and Expression*, 2d ed. Cambridge University Press, Cambridge, pp. 98–134, 1991), may be more consistent with an error in the original ATM sequence.

Knowledge of the spectrum of mutations occurring in the ATM gene in AT patients is an important prerequisite for structure-function studies of the gene, as well as a guide for mutation screening strategies in the general population of individuals without a family history of AT. The large size of the ATM gene creates significant obstacles for both of these approaches. Here, the availability of cell lines from AT patients has been taken advantage of to carry out SSCP screening on amplified ATM cDNA fragments. A diverse array of mutations, the majority of which would be predicted to lead to truncation of the protein, were detected. This high frequency of truncation mutations may have important implications for AT heterozygotes where some of these mutations may function as mild dominant negatives. These results suggest that there are a large number of different mutant ATM alleles in the general population and that non occur at a high frequency.

TABLE 2

Sequence Variants Identified in the ATM Gene

| | | cDNA | | Protein | | | Genomic DNA | |
| --- | --- | --- | --- | --- | --- | --- | --- | --- |
| Cell Line | Exon | Change | Nucleotide[a] | Change[b] | Codon[c] | Change | Nucleotide[a] | Comments |
| AT7LA | 12 | ΔAG | 1561 | Ter | 521 | ΔAG | 1561 | Homozygous |
| GM02782 | 17 | Δ19 nt | 2251 | Ter | 750 | | | Cryptic 3' acceptor |
| LM217[d] | 17 | Δ19 nt | 2251 | Ter | 750 | | | Cryptic 3' acceptor |
| GM11255 | 17 | Δ217 nt | 2251 | Ter | 750 | | | Δexons 17, 18 |

TABLE 2-continued

Sequence Variants Identified in the ATM Gene

| Cell Line | Exon | cDNA Change | Nucleotide[a] | Protein Change[b] | Codon[c] | Genomic DNA Change | Nucleotide[a] | Comments |
|---|---|---|---|---|---|---|---|---|
| AT7SE | 17 | Δ217 nt | 2251 | Ter | 750 | | | Δexons 17, 18 |
| GM00637[d] | 20 | Δ283 nt | 2639 | Ter | 880 | | | Δexons 20, 21 |
| AT31LA | 23 | Δ207 nt | 3078 | Δ69 aa | 1026 | | | Δexons 23, 24 |
| AT10SE | 23 | Δ73 nt | 3109 | Ter | 1037 | | | |
| GM08436 | 33 | ΔGATA | 4638 | Ter | 1546 | ΔGATA | 4638 | |
| GMO2782 | 40 | Δ88 nt | 5675 | Ter | 1892 | | | Δexon 40 |
| AT13LA | 41 | ins 130 | 5763 | Ter | 1921 | | | insert between exons 40, 41 |
| AT16LA | 44 | Δ103 nt | 6096 | Ter | 2032 | | | Δexon 44 |
| AT30LA[e] | 46 | Δ105 nt | 6348 | Ter | 2124 | ins G | 6348 | splices out mutant exon |
| GMO2782 | 48 | Δ81 nt | 6573 | Δ27 aa | 2191 | | | cyrptic 3' acceptor |
| AT6SE | 50 | Δ114 nt | 6976 | Δ38 aa | 2326 | | | Δexon 50 |
| AT5B1 | 51 | Δ34 nt | 7274 | Ter | 2425 | | | cryptic donor |
| GM11261 | 52 | C→T | 7327 | R→Ter | 2443 | C→T | 7327 | |
| AT13LA | 54 | Δ159 nt | 7630 | Δ53 aa | 2544 | | | Δexon 54 |
| AT9SE | 54 | Δ9 nt | 7638 | Δ3 aa | 2546 | Δ9 nt | 7638 | |
| AT31LA | 54 | Δ9 nt | 7638 | Δ3 aa | 2546 | Δ9 nt | 7638 | |
| AT8SE | 54 | Δ9 nt | 7638 | Δ3 aa | 2546 | Δ9 nt | 7638 | Confirmed in sib, AT9SE |
| GM11261[e] | 54[f] | Δ298 nt | 7630 | Ter | 2544 | | | Δexon 54, 55 |
| GM11261 | 55[f] | Δ139 nt | 7789 | Ter | 2597 | | | Δexon 55 |
| GM11261 | 55[f] | | | R→S | 2642 | (A→C)Agtatgtttt | 7926 | conserved position for splicing |
| AT4SE | 55 | Δ139 nt | 7789 | Ter | 2597 | ttattaa(t→g)agGA | intron | splice-acceptor mutation |
| 1AT2203 | 55 | Δ139 nt | 7789 | R→Ter | 2598 | C→T | 7792 | Δexon 55 |
| AT13SE | 57 | Δ140 nt | 8011 | Ter | 2671 | (A→G)Ggtgagcct | 8150 | Δexon 57 |
| GMO3189 | 58 | Δ117 | 8152 | Δ39 aa | 2758 | | | Δexon 58 |
| AT3ABR | 58 | A→T | 8266 | K→Ter | 2756 | A→T | 8266 | |
| GMO9587[e] | 59 | Δ150 nt | 8269 | Ter | 2758 | TG(Δgtga)gtgaca | intron | splice-donor mutation |
| AT1SE | 59 | Δ150 nt | 8269 | Ter | 2758 | TG(Δgtga)gtgaca | intron | splice-donor mutation |
| GM11254[e] | 62 | Δ115 nt | 8672 | Ter | 2891 | AG(g→a)taagtgata | intron | splice-donor mutation |

[a]The first nucleotide of the open reading frame in the ATM gene was designated as "1."
[b]Changes in which specific numbers of amino acids are indicated are predicted to be in-frame alterations.
[c]Indicates the codon interrupted by mutation.
[d]Cell line derived from an individual without family history of AT.
[e]Alteration in cDNA described elsewhere (Savitsky et al., Science 268:1749–1753, 1995; Gilad et al., Hum Mol Genet 5:433–439, 1996).
[f]All one allele of GM11261.

III. Common Ethnic Mutations in the ATM Gene

Using a protein truncation test that detects approximately 70% of ATM mutations, new mutations were defined in the ATM gene in ethnic populations so as to make possible the screening of these populations for other conditions that may relate to AT heterozygosity. Both genomic mutations and their effects on cDNA are reported. Based on these findings, rapid assays were designed that now allow screening of small amounts of DNA. These assays detect mutations in 55% of Costa Rican patients, 50% of Norwegians, 27% of Polish, 7% of Italians, as well as those of patients from Amish/Mennonite and Utah-Mormon backgrounds. The broad spectrum of ATM mutations observed suggests that perhaps the ATM protein itself plays a role in preventing spontaneous ATM mutations from becoming fixed into future generations.

There is great interest in screening cancer-risk populations for mutations in the ATM gene. With over 200 mutations now defined, a spectrum of ATM mutations is emerging that distributes mutations rather uniformly along the gene. This will influence how large-scale screening experiments should be designed. The results of the experiments reported herein show that instead of screening and sequencing over the entire gene, it is possible to identify distinct ethnic mutations for which rapid assays can be developed that use genomic DNA to detect public or "founder effect" mutations in Norwegian, Costa Rican, Polish, Italian, Japanese, Amish, and Utah-Mormon populations.

The general design of the experiments reported in Example 3 was to first identify sites of truncation by PTT. Suspect cDNA and DNA segments were then sequenced to characterize the cDNA defect and the underlying genomic DNA mutation, respectively. With this information, rapid assays were designed and used to screen additional patients so that the mutation frequencies could be estimated.

Nomenclature

ATM mutations were initially detected in cDNAs derived from lymphoblastoid cell lines (LCLs) of AT patients; genomic mutation sites occasionally differed from the mutation sites observed in cDNA. This was especially true of splice site mutations. Thus, reference is made herein first to the nucleotide position of the genomic mutation (e.g., 6095G>A), and then to the cDNA lesion and the first affected codon (e.g., c2003del89): 6095G>A (c2003del89nt).

Results

Figure 2:
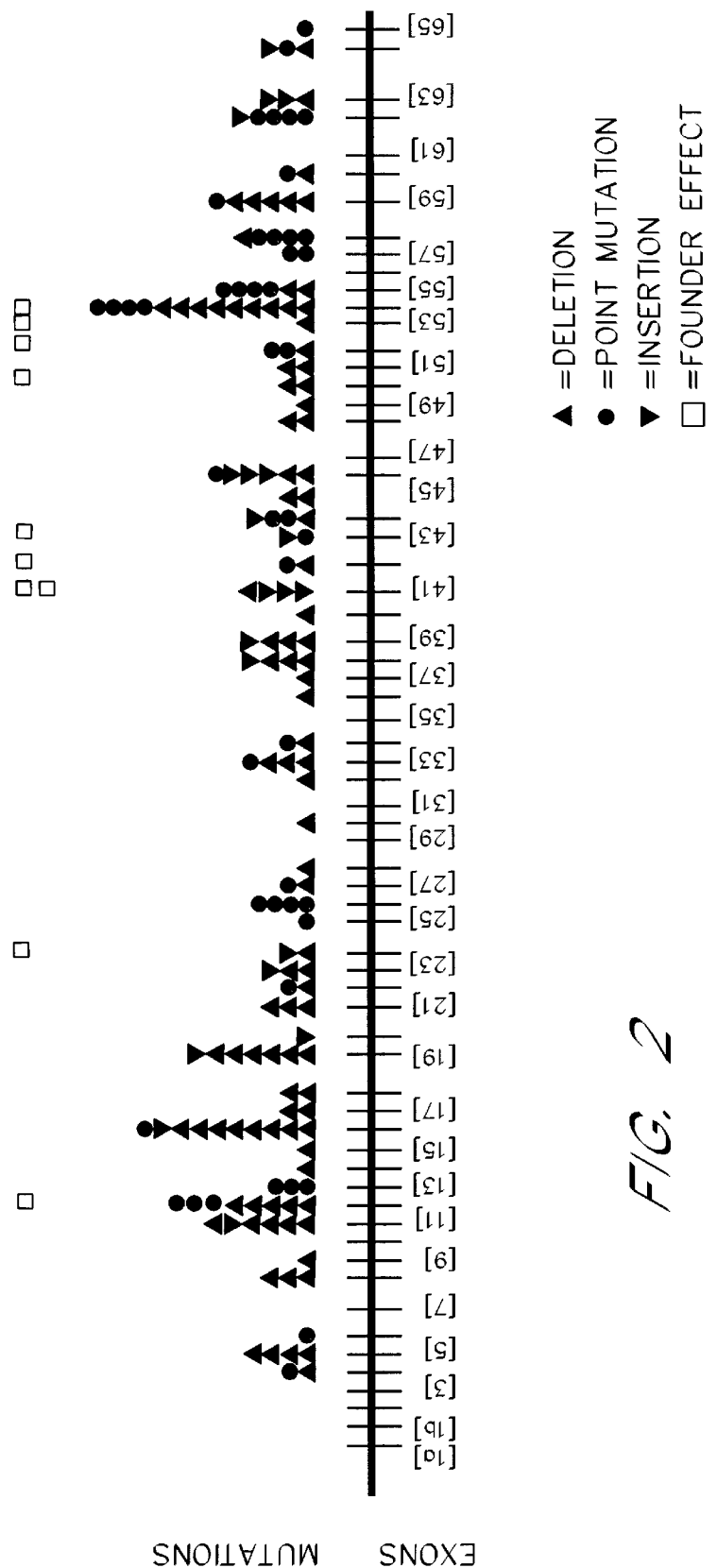
FIG. 2. Spectrum of ATM mutations, based on over 200 mutations (see text).

FIG. 2 depicts the spectrum of all published ATM mutations (Savitsky et al., Science 268: 1749–1753, 1995; Savitsky et al., Hum Mol Genet 4: 2025–2032, 1995; Gilad et al., Hum Mol Genet 5: 433–439, 1996; Gilad et al., Hum Mol Genet 5: 2033–2037, 1996; Baumer et al., Hum Genet 98: 246–249, 1996; Byrd et al., Hum Mol Genet 5: 145–149, 1996; McConville et al., Am J Hum Genet 59: 320–330, 1996; Wright et al., Am J Hum Genet 59: 839–846, 1996; Vorechovsky Eur J Hum Genet 4: 352–355, 1996), as well as those reported herein and 50 previously unpublished mutations. So as not to bias the emerging spectrum of ATM mutations, the mutations that recurred in certain ethnic populations or were associated with shared haplotypes were represented only once and boxes placed at those locations in FIG. 2. These are considered founder effect mutations. User-friendly assays were designed for rapid detection of some of these more common mutations using genomic DNA as the template for PCR amplification. Norwegian, Costa Rican, Italian, Polish and Amish mutations were selected as well as a generally common mutation at 7638del9(c2546) (Savitsky et al., Science 268: 1749–1753, 1995; Gilad et al., Hum Mol Genet 5: 433–439, 1996; Wright et al., Am J Hum Genet 59: 839–846, 1996).

Norwegian Mutation

Figure 4:
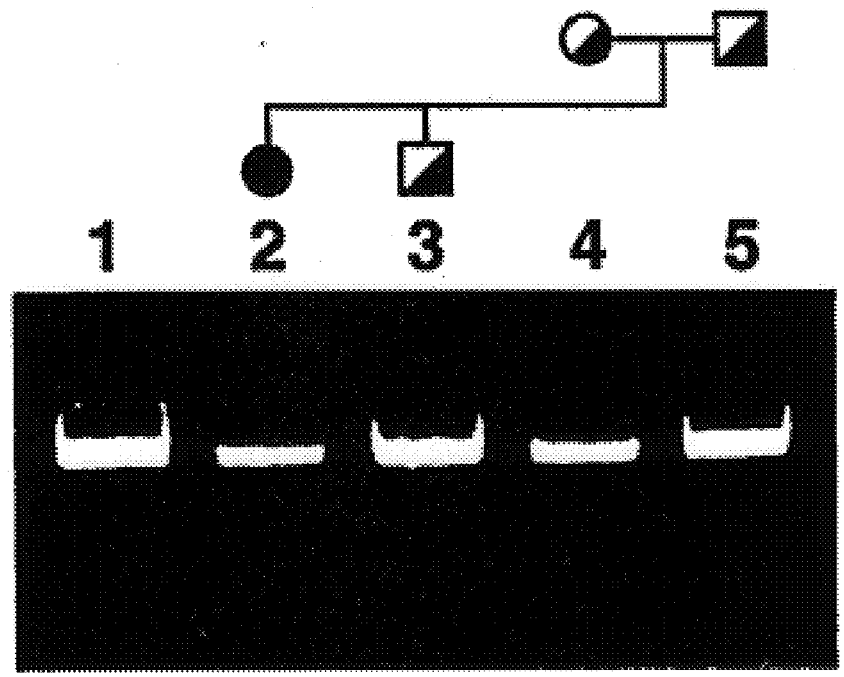
FIG. 4. Heteroduplex and haplotype analysis of a Norwegian family. Lane 1 is a heteroduplex mixture of DNA from an affected child and a normal; lane 2 is the affected child alone; lanes 3–5 are heterozygotes (sister, lane 3; mother, lane 4; father, lane 5). Bracketed letters indicate corresponding haplotypes.

3245ATC>TGAT (c1081) mutation. Two Norwegian patients showed protein truncation in PTT region g; one was homozygous for the same truncated band, the other heterozygous (FIG. 3a). Sequence analysis revealed a complex frame shift mutation, 3245ATC>TGAT(c1081) in exon 24. Primers flanking the mutation were designed from genomic DNA sequence (Savitsky et al., Hum Mol Genet 4: 2025–2032, 1995; Rasio et al., Canc Res 55: 6053–6057, 1995; Vorechovsky et al., Canc Res 56: 2726–2732, 1996). DNA from eight unrelated Norwegian AT patients and their siblings were amplified for this region and their PCR products subjected to heteroduplex analysis (FIG. 4). Three patients were found to be homozygous and two heterozygous for this mutation. The carrier status of the siblings was also identified. Haplotype analysis with seven markers demonstrated that all of the five patients who had the mutation shared the same haplotype. An American patient of Norwegian ancestry was also found to have this mutation.

Costa Rican Mutations

Figure 5:
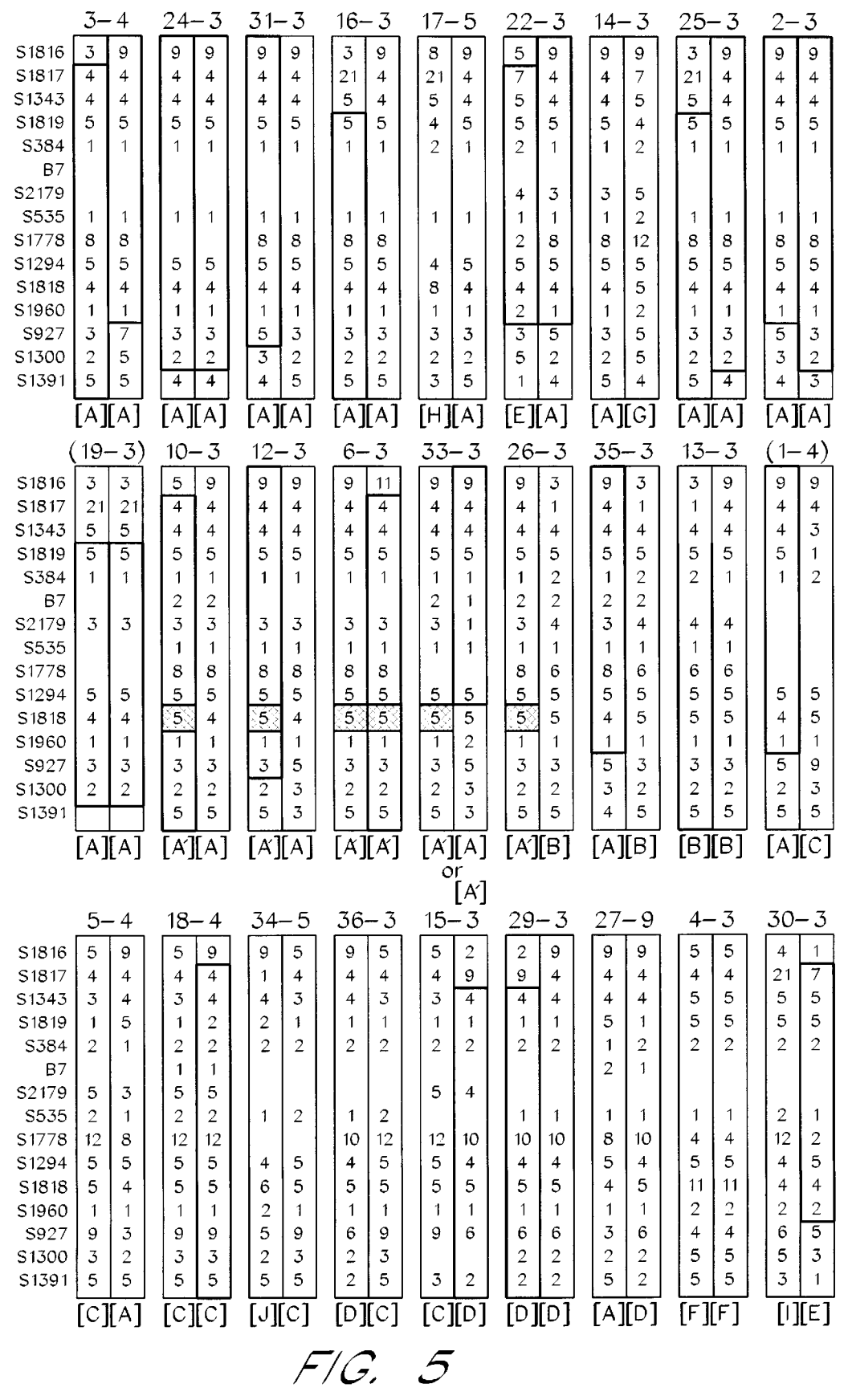

In a previous study, only 10 distinct marker haplotypes were found to encompass all Costa Rican AT patients (Uhrhammer et al., Am J Hum Genet 57: 103–111, 1995). Since that report, further testing has slightly altered the characterization of haplotype [B] (FIG. 5). Other than this, the original haplotype assignments of A to J were retained. Together, the haplotypes [A], [B], [C] and [D] account for 85% of the Costa Rican patients studied. The mutations of haplotypes [A], [B] and [C] have been identified herein.

Figure 6:
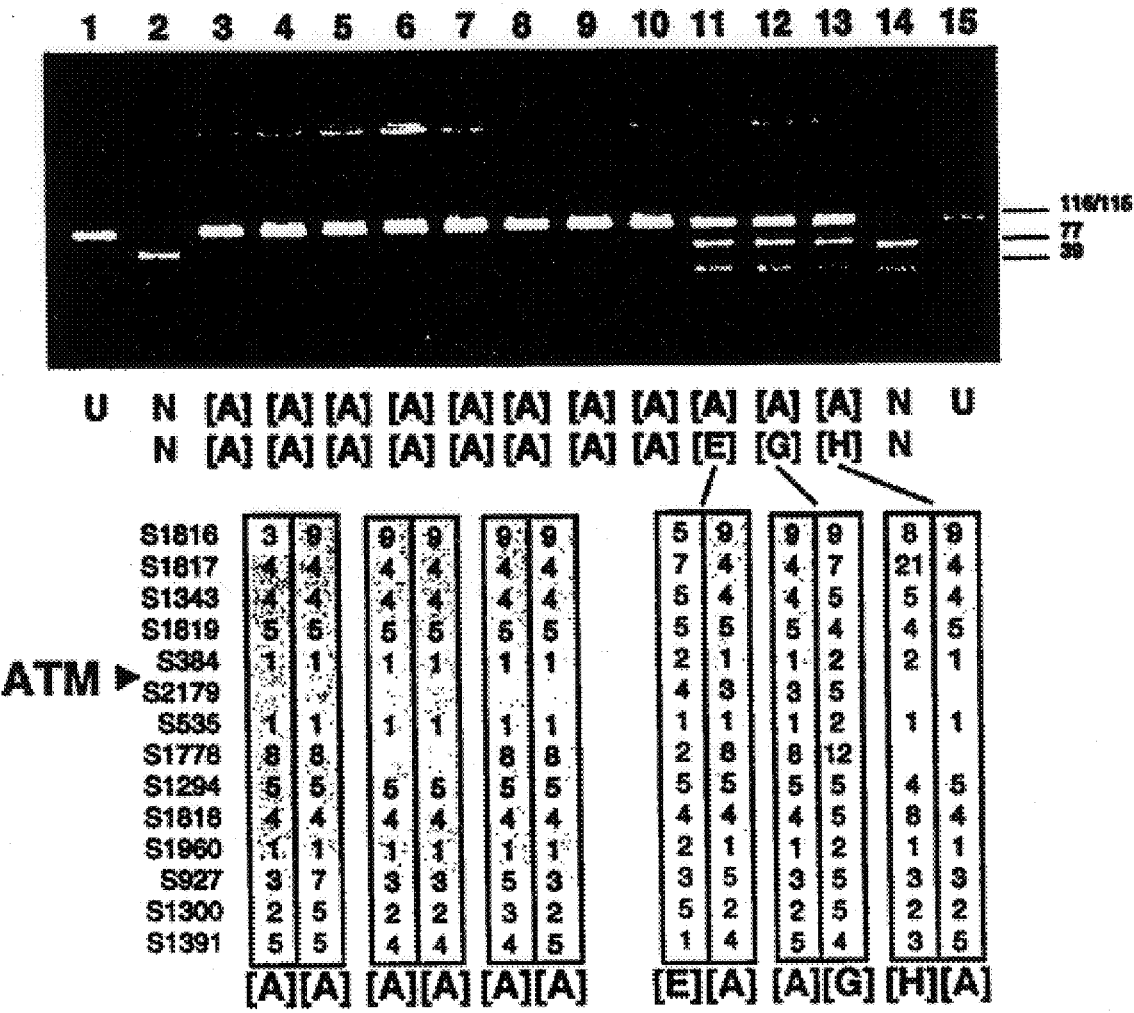
FIG. 6. Sau3A I digestion of 11 PCR products from Costa Rican patients. Lanes 1 and 15 are undigested (U) samples; lanes 2 and 14 are digested normals (N); lanes from 3 to 10 are AT patients who were homozygous for haplotype [A] and are homozygous for the 5908delC mutation, as indicated by the undigested bands. Lanes 11, 12 and 13 are compound heterozygotes showing both digested and undigested bands.

1. Haplotype [A] mutation. PTT of a haplotype [A] patient demonstrated protein truncation in region b (FIG. 3b). Sequence analysis identified the mutation as a deletion of a C residue in exon 41 at position 5908 (c1970), (5908delC). The mutation abolishes a Sau3A 1 restriction enzyme digestion (RED) site. Primers flanking the mutation were designed from genomic DNA sequence. The PCT product (116 bp) of a normal individual was expected to produce two bands of sizes 77 bp and 39 bp when digested with Sau3A 1; however, since the 5908delC mutation abolishes the RED site, only one band of size 115 bp is observed in patients who are homozygous for haplotype [A]. Genomic DNA from twenty-seven Costa Rican patients was PCR amplified across this region, digested with Sau3A 1, and the products were electrophoresed on a 3:1 NU SIEVE agarose gel (FIG. 6). Thirteen patients were found to be homozygous and six patients were heterozygous for the 5908delC mutation. This result was in complete agreement with the haplotyping data. The frequency of the 5908delC mutation in 27 Costa Rican patients is 56%.

Figure 7:
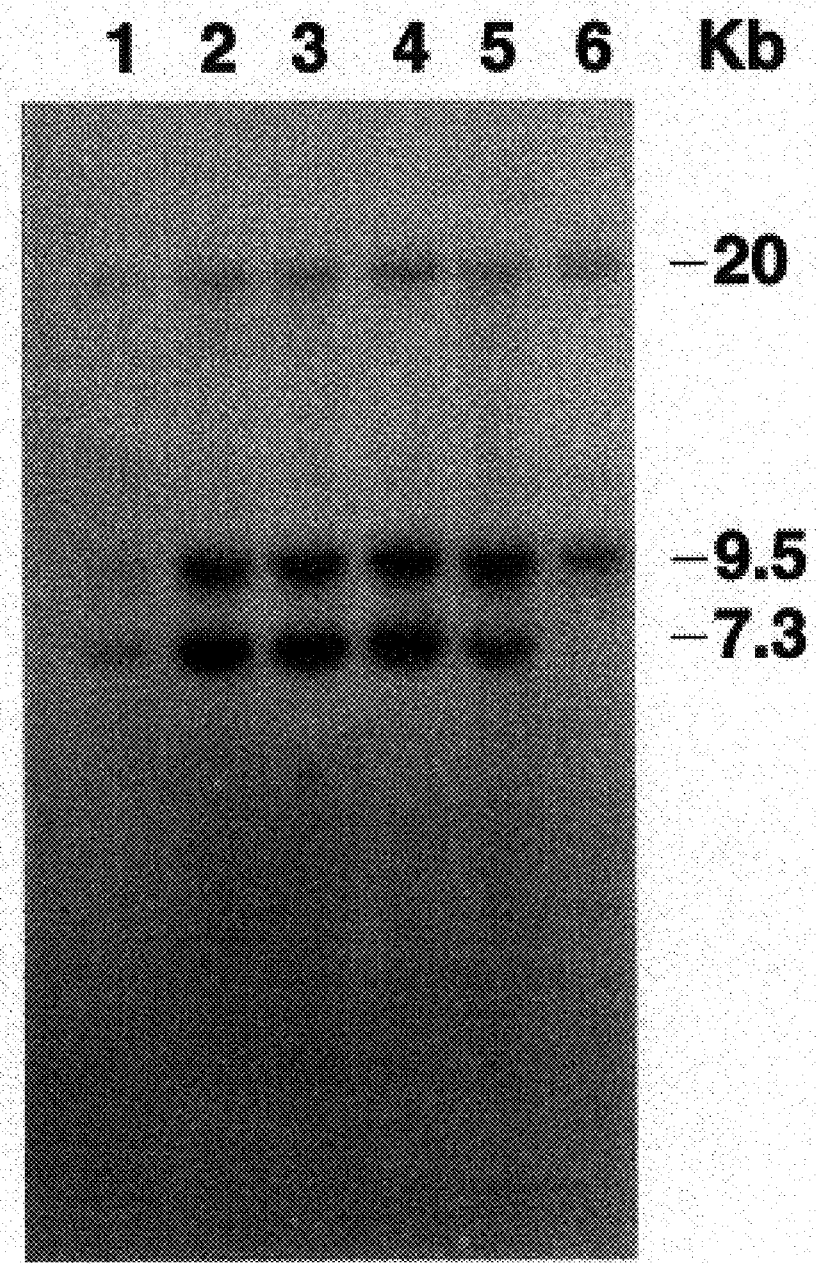
FIG. 7. Southern blot analysis to demonstrate deleted segment at 3' end of ATM gene. The cDNA probe covers the last five exons. Lanes 1–4 are normals, lane 5 is a heterozygote, lane 6 is a homozygous haplotype [B] patients. DNA was digested with Bgl II.

2. Haplotype [B] mutation. The haplotype [B] mutation is a large deletion at the 3' end of the gene. Southern blot analysis with restriction enzyme Bgl II shows that the homozygous patient (lane 6) deletes a fragment of the gene (FIG. 7). Three patients share the [B] haplotype. The frequency of this mutation is 7.4%.

Figure 8:
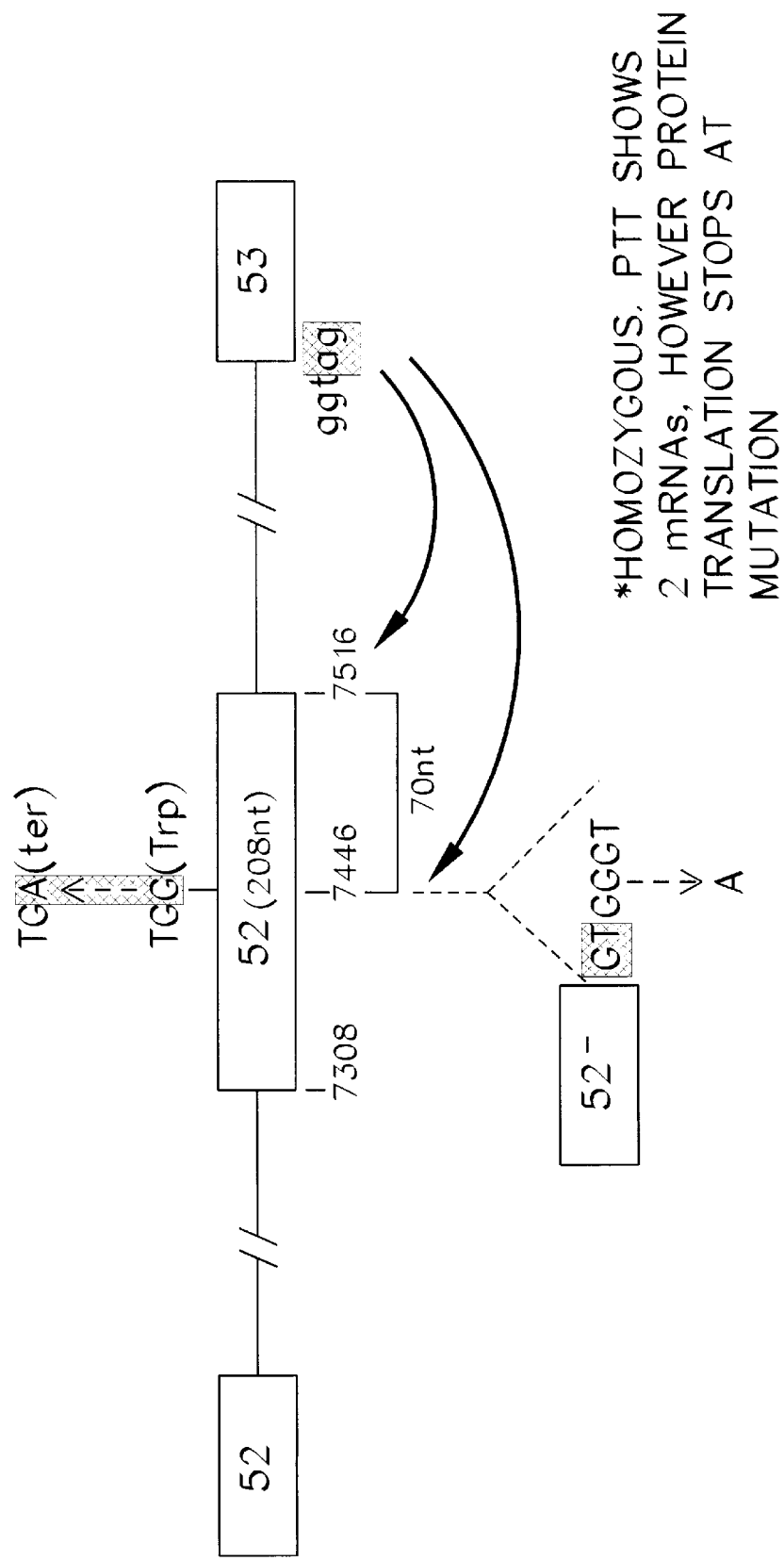
FIG. 8. Proposed mechanism for the deletion of 70 nt in the cDNA of a Costa Rican haplotype [C] patient, as a consequence of the genomic G>A substitution.

3. Haplotype [C] mutation. A haplotype [C] patient showed truncation in region c. The mutation was identified by sequencing as a substitution of G to A at position 7449. This G to A transition creates a TGG(trp)>TGA(ter) and a cryptic splice site at 7446 so that 70 nucleotides are deleted from the 3' end of exon 52 beginning at codon 2481 (FIG. 8); this deletion includes the TGG(trp)>TGA(ter) mutation site. Haplotype [C] was observed in 7 chromosomes out of 54, a frequency of 13%.

Polish Mutations

Haplotypes of twenty-two Polish AT patients were analyzed for linkage disequilibrium. Ten patients with representative haplotypes were screened by PTT. Eight distinct mutations were identified. Rapid assays were designed for five of these mutations and used to screen all 22 patients, as well as to screen American patients of Polish ancestry.

Figure 9A:
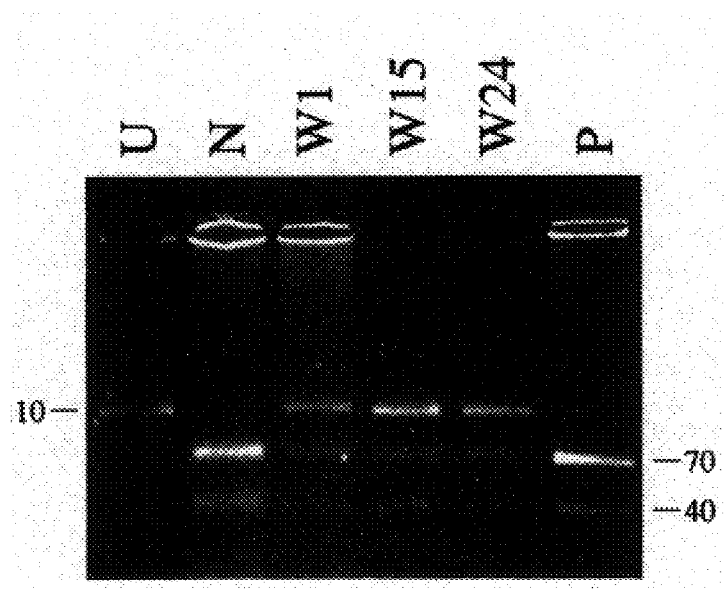
FIG. 9. Comparison of Polish mutations and haplotypes. (a). Alu I digestion; three heterozygous Polish patients who have the 7630-2A>C mutation. Lanes 3–5 are patient samples; lane 6 is a patient with a cDNA deletion of exon 54 who does not have the 7630-2A>C genomic mutation. Haplotype analysis shows that patients in lanes 3, 4 and 5 share a common haplotype around the ATM gene (data shown in f), whereas the patient in lane 6 does not. (b). Bfa I digestion: three heterozygous Polish patients (lanes 3–5) who have the 6095G>A(2003del89nt) mutation in exon 43. (c). Tfi I digestion: four Polish patients. Lanes 1 and 2 are patients who have the 7010delGT mutation in exon 50. Patients in lanes 3 and 4 do not. (d). Mse I digestion: six Polish patients (lanes 3–8). Lanes 4 and 8 are patients with the 5932G>T mutation in exon 42. (e). Mse I digestion: three Polish patients (lanes 1–3). Lane 1 is a patient with the 3214G>T mutation in exon 24. (f). Haplotype analysis of the ten Polish patients described above. Shaded areas represent four shared haplotypes.

1. 7630-2A>C(c2544del159nt) mutation. This mutation results in a deletion of exon 54 beginning at codon 2544. The mutation alters the invariant splice acceptor site at −2 from exon 54 (Wright et al., Am J Hum Genet 59: 839–846, 1996). The mutation abolishes an Alu I RED site. Primers flanking the mutation were designed from genomic sequence. When normal DNA is digested with Alu I, a 110 bp PCR product is divided into bands of 70 bp and 40 bp; the 110 bp PCR product of alleles with the 7630-2A>C mutation remains undigested (FIG. 9a). Of seven AT patients with deletions of exon 54 by RT-PCR-based tests, four had this mutation on genomic testing. These four patients were all Polish and shared a common haplotype. Thus, this mutation is represented only once in FIG. 2 and as a founder effect mutation (box) as well. We failed to find this mutation in 80 normal chromosomes.

Figure 9B:
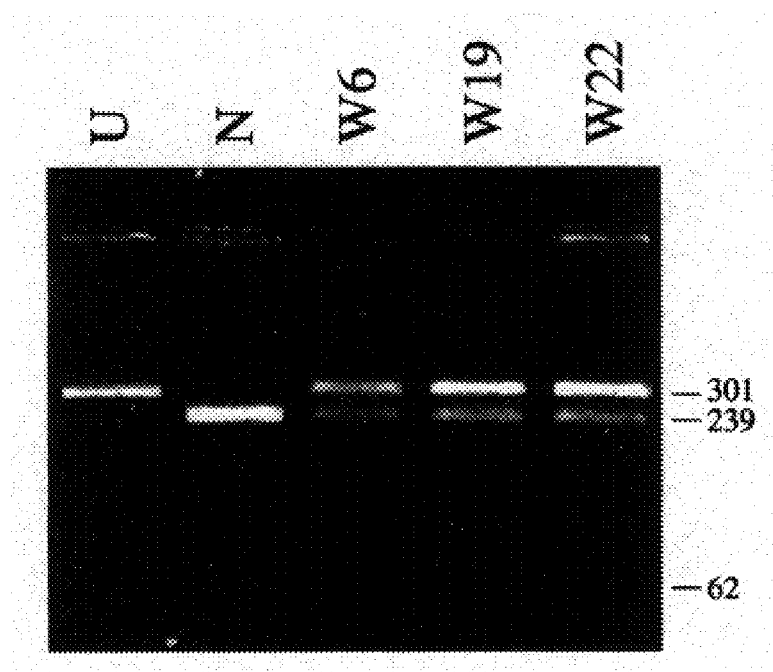

2. 6095G>A(c2003del89nt) mutation. This mutation, found in Polish AT patients, involves a G>A substitution of the last nucleotide of exon 43 and results in the deletion of exon 43 from the CDNA. The mutation abolishes a Bfa I RED site. Primers flanking the mutation were designed from genomic sequence. When digested with Bfa I, a 301 bp PCR product from normal individuals shows two bands of 239 bp and 62 bp, whereas patients with the 6095G>A mutation show only the 301 bp product undigested. Genomic DNA from twenty-two Polish AT patients was screened for this mutation; three were found to be heterozygous (FIG. 9b). These patients shared a common haplotype. We failed to find this mutation in 80 normal chromosomes.

Figure 9C:
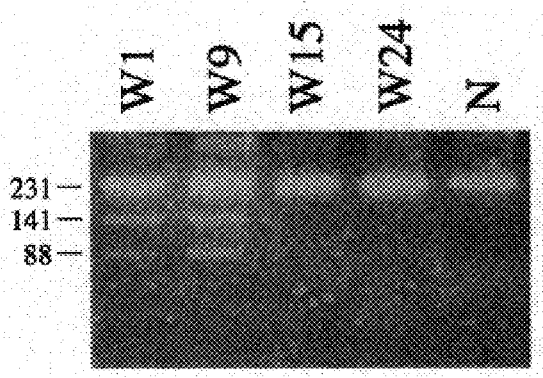

3. 7010delGT(c2337) mutation. Deletion of GT at position 7010 in exon 50 is another mutation seen in Polish patients. The mutation creates a Tfi I RED site. Genomic DNAs were amplified with primers flanking exon 50 and the products were digested with Tfi I. When digested with Tfi I, a 231 bp PCR product remains undigested in the normals, whereas the patients with this mutation produce two bands of 141 bp and 88 bp (FIG. 9c). Two of twenty-two patients were found to be heterozygous for 7010delGT mutation. These two patients shared a common haplotype.

Figure 9D:
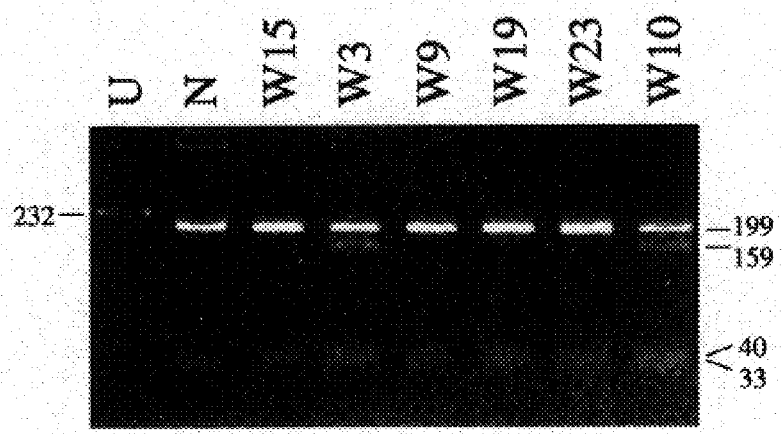

4. 5932G>T(c1973del88nt) mutation. This mutation creates a stop codon (GAA>TAA). In cDNA, exon 42 is frequently deleted. The G>T substitution creates a GAA (Glu)>TAA(ter), a Mse I RED site. Primers flanking the mutation were designed from genomic DNA sequence. When the normal 232 bp PCR product is digested with Mse I, two bands of 33 bp and 199 bp are observed, whereas patients with the 5932>GT mutation produce three bands of 33 bp, 40 bp and 159 bp (FIG. 9d). Genomic DNAs of twenty-two Polish AT patients were screened and two were found to be heterozygous for this mutation. These two patients shared a common haplotype. We failed to find this mutation in 80 normal chromosomes.

Figure 9E:
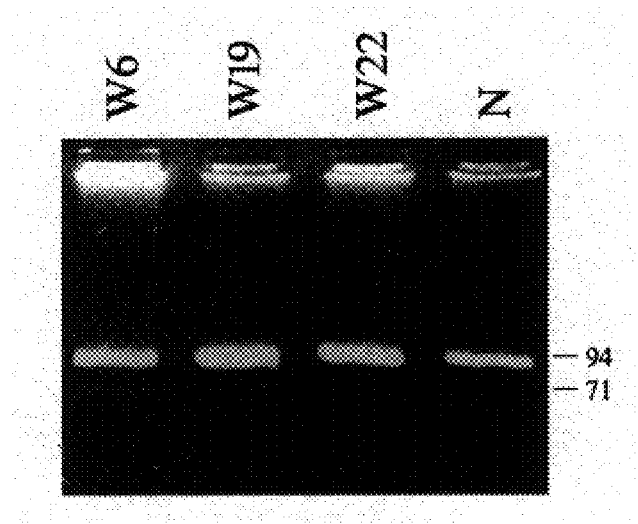

5. 3214G>T(c1026del207nt) mutation. This mutation in exon 24 also results in the creation of a stop codon GAA (Glu)>TAA(ter). In cDNA, a variant form of mRNA is observed in which exons 23 and 24 are deleted and splicing over occurs maintaining the correct reading frame. The mutation creates a Mse I RED site. PCR primers flanking the mutation were designed from genomic DNA sequences. When digested with Mse I, a 94 bp PCR product remains undigested in normals, whereas patients with this mutation produce two bands of 71 bp and 23 bp (FIG. 9e). Genomic DNA of twenty-two Polish AT patients were amplified for exon 24 (with the same primers used for detecting the 3245 ATC>TGAT Norwegian mutation) and digested with Mse I; only one Polish patient was found to be heterozygous for this mutation. We failed to find this mutation in 80 normal chromosomes.

6. Three additional and unique mutations were identified in Polish patients for which rapid assays were not designed: 432insA (c144), 3087insA (c1029) and 8766insT (c2922).

Figure 10:
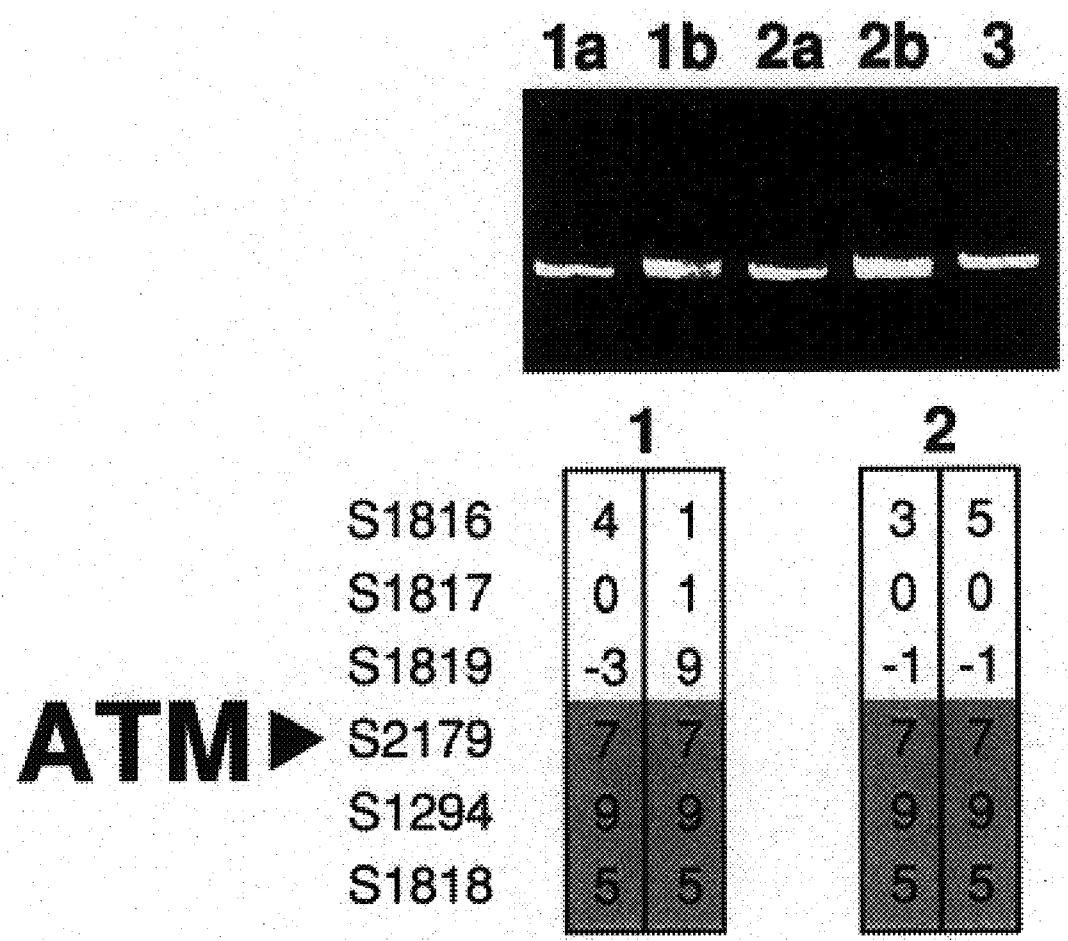
FIG. 10. Heteroduplex and haplotype analysis of two homozygous Italian patients showing the 7517del4 mutation. Lanes 1a and 2a are the patient samples; lanes 1b and 2b contain the heteroduplex mixture of DNAs from normals with those of patients 1a and 2a, respectively; lane 3 is a normal control. Haplotype analysis has shown that both patients share both haplotypes at chromosome 11q23. 1.

Italian Mutations 1. 7517del4(c2506) mutation. The most common Italian mutation is a deletion of 4 nucleotides at position 7517 in exon 53, originally described by Gilad et al., Hum Mol Genet 5: 433–439, 1996, that is found primarily in Central-South Italy (LC). Primers flanking the mutation were designed from genomic sequence of heteroduplex analysis. Twenty-eight additional AT patients of Italian ancestry were screened for the mutation. Two patients showed this mutation; both were homozygous (FIG. 10) and shared the same two haplotypes at the chromosome 11q23.1.

2. Two other mutations were identified in Italian AT patients, both sharing protein truncations in region f. One mutation, 1607G>T(c536ins800), is a G>T substitution at the last nucleotide of exon 12; this leads to a failure to splice the 800 bp intron 12, and a consequent frameshift. The other mutation is 2493insA(c835).

Amish Mutation

Figure 11:
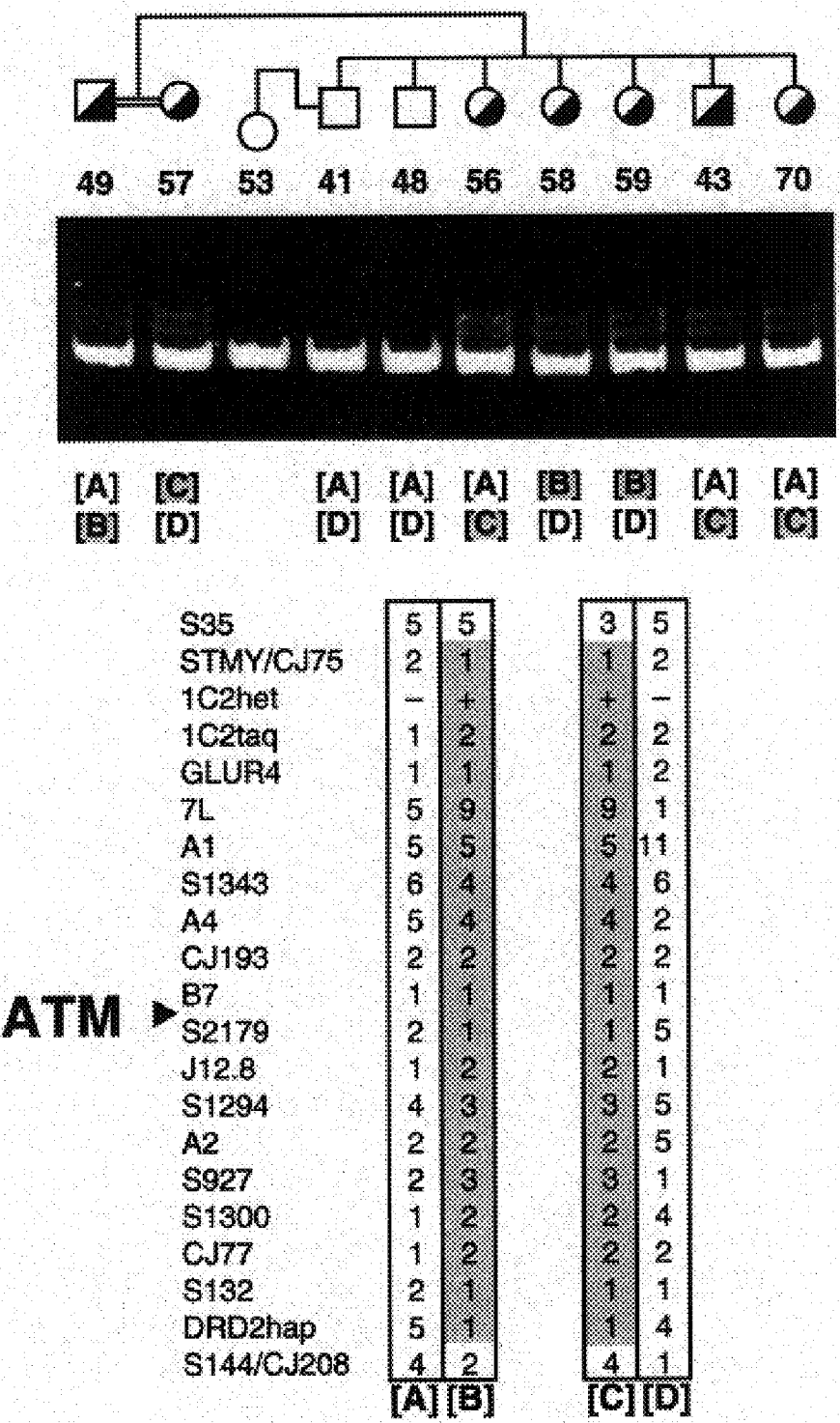
FIG. 11. Heteroduplex and haplotype analysis of a consanguineous Amish family showing the inheritance of the 1563delAG mutation. Haplotype analysis has shown that the mutation is inherited through haplotypes B and C. Heteroduplex analysis confirms that any person in the family with either haplotype B or C is a carrier for the mutation.

1563delAG(c522) mutation. This mutation, observed in the original Amish family described by Gatti et al., Nature 336: 577–580, 1988, was a deletion of AG at position 1563 in exon 12 (c522). PCR primers flanking the mutation were designed from genomic DNA sequence. Seventy-one members of an Amish pedigree (complementation group A) were screened for the mutation by heteroduplex analysis (FIG. 11). All patients were found to be homozygous for this mutation, as well as for all adjacent markers. Two other families of Mennonite/Amish origins with AT-like affecteds were screened; surprisingly, neither the mutation nor the expected haplotype in these families was observed. Lymphoblastoid cell lines from the affecteds were tested for radiosensitivity and showed the characteristic decreased postradiation colony survival of AT cells (Huo et al., Canc Res 54: 2544–2547, 1994). A second homozygous mutation was identified in one of these families, 5932G>T (c1973del88), which is described above in two Polish patients who share a common haplotype. This haplotype is also found in the Mennonite family.

Utah-Mormon Mutations

Three different mutations were identified in Utah-Mormon families. One patient was homozygous for 4612-12A>G(c1538ins11). This resulted in at least four cDNA mutations; an insertion of 11 nt lengthened exon 33 in all of them; in three of the cDNAs, exon skipping of 1, 2, or 3 exons was observed. Another patient was heterozygous for the mutation 8494C>T(c2832), and one patient was heterozygous for the 8786G>A(c2891del115) mutation.

African-American Mutations

Four mutations were identified in two African-American patients. One patient was heterozygous for mutations 2251-10T>G(c750ins9nt) and 2810insCTAG(c937ins); the other patient was heterozygous for mutations 7327C>T(c2443) and 7926A>C(c2544del298nt). The latter patient was described previously by Wright et al., Am J Hum Genet 59: 839–846, 1996.

Japanese Mutations

Gilad et al., Hum Mol Genet 5: 433–439, 1996, reported two ATM mutations in Japanese patients. One of these mutations, 7883del5, was homozygous in one patient and heterozygous in the second. In one additional Japanese patient, one copy of this mutation was detected. Thus, in a limited survey, 7883del5 accounts for 4 of 6 mutant alleles assayed in this population. Although no convenient restriction enzyme site is created or destroyed by this mutation, it is easily detected by SSCP or heteroduplex analysis.

Public Mutation

7638del9(c2546) mutation. This appears to be a public mutation in exon 54 in that it has been observed in nine AT patients of apparently different origins and at least two different haplotypes (Savitsky et al., Science 268: 1749–1753, 1995; Gilad et al., Hum Mol Genet 5: 433–439, 1996; Wright et al., Am J Hum Genet 59: 839–846, 1996). The mutation has also been observed in a Swedish breast cancer family (Vorechovsky et al., Canc Res 56: 4130–4133, 1996). A simple assay for its detection was designed and tested. The same exon 54 primers were used that were employed for detection of the 7630-2A>C mutation seen in Polish patients. The nine nucleotide deletion includes the deletion of a Bfa I RED site; two bands are observed in normal individuals of sizes 78bp and 32bp, whereas patients with this mutation show only a single band of 101bp. Using another rapid assay (Wright et al., Am J Hum Genet 59: 839–846, 1996), this mutation has not been observed in >300 normal chromosomes.

Discussion

From the vantage of having over 200 ATM mutations now defined in AT patients, one can begin to assess the various approaches to mutation detection for the ATM gene. First, virtually all patients who are not of a consanguineous background are compound heterozygotes. Further, there are few, if any, "hotspots" in the gene. The most common mutation, 2544del9, accounts for ~8% and is found worldwide (Savitsky et al., Science 268: 1749–1753, 1995; Gilad et al., Hum Mol Genet 5: 433–439, 1996; Wright et al., Am J Hum Genet 59: 839–846, 1996). Most patients make mRNA for both mutated alleles. Approximately 70% of ATM mutations result in a truncated protein. Thus, many patients make a foreshortened mRNA that does not contain the catalytic kinase domain at exons 60–62. On the other hand, a few patients have been identified whose mutations do not delete the kinase region, with no discernible difference in clinical symptoms.

A wide array of mutation detection techniques have been tried. Since the gene is so large (~150 kb), most of these have used cDNA as the starting template. To date, the single most effective method of screening for cDNA mutations has been the protein truncation test (PTT). As a complementary method to PTT, CSGE has been used to screen 600–800 nt segments of ATM cDNA. This has yielded ~35 mutations per 100 chromosomes screened, some of which detected those identified by PTT as well. Several laboratories have used REF to screen cDNA segments of 1000–2000 nt, with good success (Liu et al., BioTechniques 18: 470–477, 1995; Gilad et al., Hum Mol Genet 5: 433–439, 1996). However, because all ATM exons are smaller than 372 nt (exon 12), none of these methods can be applied to screening genomic DNA.

Great interest was aroused by two reports from Swift et al., N Engl J Med 316: 1289–1294, 1987, and Swift et al., N EngI J Med 325: 1831–36, 1991, suggesting that the risk of breast cancer among female AT heterozygotes was increased by 5- to 8-fold. Reports from the United Kingdom (Pippard, et al., Canc Res 48: 2929–2933, 1988; Easton, Intl J Radiat Biol 66: S177–S184, 1994) and Norway (Borresen et al., Genes Chromosom Cancer 2: 339–341, 1990) supported this observation although the limited number of families in each study prevented statistically convincing conclusions. A recent report by Athma et al., Canc Genet Cytogenet 92: 130–134, 1996, used haplotyping to unambiguously identify carriers in AT families and again demonstrated an increased incidence of breast cancer in these individuals.

The effort here has been to move as quickly as possible towards testing genomic DNA so that large numbers of breast cancer patients might be screened for ATM mutations. The problem of testing for many ATM mutations may be circumvented by defining the frequency of founder-effect and common mutations in ethnic populations. In this way, it is hoped that heterozygote screening efforts can begin on these limited populations. Thus far, rapid genomic testing allows mutations to be detected in 55% of Costa Ricans, 50% of Norwegians, 27% of Polish, 7% of Italians, as well as a rapid test for the Mennonite/Old Order Amish. The effectiveness of using the three known Utah-Mormon mutations for heterozygote identification in this largely-outbred population is likely to be low. A common mutation, 7638del9(c2546), observed in ~8% worldwide, can now be detected rapidly by either of two assays (Wright et al., Am J Hum Genet 59: 839–846, 1996; and herein).

Each rapid assay also allows large-scale screening of AT homozygotes with as-yet-unidentified mutations. In so doing, the Norwegian and Italian mutations in a few American families of these ancestries was detected, and this approach has allowed us to rapidly determine the frequency of particular mutations across a large sample of AT homozygotes. Nonetheless, new mutations are still being detected and are far from saturating the list of possible mutations.

Investigators wishing to test hypotheses relating breast cancer incidence to AT heterozygosity in outbred populations face a daunting task. AT is an infrequent disorder. Extending AT families with known mutations to include cases of breast cancer will be difficult and may not yield sufficient numbers of cases and controls to resolve this issue. On the other hand, population screening in breast cancer cases and controls for a large gene characterized by a heterogeneous collection of mutations, as with ATM, is a major technical challenge.

Heretofore, only a single large mutation has been reported in AT affecteds, i.e., the 85 kb deletion (exons 8–56) (Savitsky et al., Science 268: 1749–1753, 1995). A second "large" deletion is reported herein extending from exon 64 to well beyond the 3' untranslated region of ATM. Thus, early attempts at probing Southern blots containing DNAs from multiple AT homozygotes with candidate transcripts were doomed to very low yields. This observation also should discourage the use of karyotyping to search for chromosome 11q-related translocations or microdeletions in undiagnosed patients suspected of having AT.

During the positional cloning of the ATM gene, over 200 families were analyzed through an international consortium. Approximately 25 of those families were set apart for one reason or another, usually because one member of the family had or lacked a clinical feature that brought the diagnosis of the entire family into question. Such families certainly had to be carefully excluded from linkage analyses. Six of the 176 families with firm diagnoses did not link to 11q23.1 (Gatti et al., Intl J Radiat Biol 66: S57–S62, 1994; Lange et al., Am J Hum Genet 57: 112–119, 1995). One of these six, CRAT 10 (Uhrhammer et al., Am J Hum Genet 57: 103–111, 1995), later linked when a young child with two affected haplotypes finally developed ataxia. Of the other five, and among many of the 25 "variant" families, at least one ATM mutation has been identified in about half. Several patients with $AT_{Fresno}$ (Curry et al., Am J Hum Genet 45: 270–275, 1989) also harbor mutations in the ATM gene. Taken together, these findings make it increasingly more unlikely that genetic heterogeneity exists for the AT syndrome.

In the Amish studies, the failure to find either the common haplotype or the 522delAG(c1563) mutation (Savitsky et al., Science 268: 1749–1753, 1995) in patients who were not members of the immediate Pennsylvania/Ohio/Indiana extended family was surprising. Further, when all other AT patients were tested with the rapid gDNA assay for this mutation, it was found in a non-Amish American family and in a Turkish family. Byrd et al., Hum Mol Genet 5: 145–149, 1996, have also reported this mutation in a British family. As described above, a second Mennonite mutation was found, 5932G>T(c1973del88), that also appears in two Polish patients.

Taken together, this increasingly broad spectrum of mutations suggests that perhaps the ATM gene product itself may somehow play a role in preventing spontaneous mutations from becoming fixed into later generations. Its recently documented dual role in both meiosis (Xu et al., Genes & Develop 10: 2411–2422, 1996; Xu et al., Genes & Develop 10: 2401–2410, 1996; Keegan, et al., Genes & Develop 10: 2423–2437, 1996) and mitosis (Meyn, Amer Soc Hum Genet 47: A13, 1990; Meyn, Science 260: 1327–1330, 1993; Meyn, Canc Res 55: 5991–6001, 1995; Shiloh, Eur J Hum Genet 3: 116–138, 1995) at times of homologous recombination and gene rearrangement, respectively, indicates that earlier interpretations describing the AT lesion as one of "DNA processing" (Painter, *Ataxia-telangiectasia: Genetics, neuropathology, and immunology of a degenerative disease of childhood* (RA Gatti and M Swift, Eds.) Alan R. Liss, Inc., New York, pp. 89–100, 1985; Painter, Intl J Radiat Biol 49: 771–781, 1986; Painter, *Ataxia-Telangiectasia*. NATO ASI Series. (RA Gatti and RB Painter, Eds.) Springer-Verlag, Heidelberg, pp. 257–268, 1993) were indeed correct.

TABLE 3

Primers used in PTT analysis and rapid detection of ethnic mutations

| PTT Fragments (Nucleotide Position) | | Nucleotide Sequence (5'–3') |
|---|---|---|
| region e (76–1392) | forward | (T7)-GAAGTTGAGAAATTTAAGC (SEQ ID NO:12) |
| | reverse | AATGCAACTTCCGTAAGGC (SEQ ID NO:13) |

TABLE 3-continued

Primers used in PTT analysis and rapid detection of ethnic mutations

PTT Fragments
(Nucleotide Position) | | Nucleotide Sequence (5'–3')
--- | --- | ---
region f (1048–2817) | forward | (T7)-GCAGATATCTGT
 | | (SEQ ID NO:14)
 | reverse | GTAGGTTCTAGCGTGCTAGA
 | | (SEQ ID NO:15)
region g (2437–4092) | forward | (T7)-AATGACATTGCAGATATTT
 | | (SEQ ID NO:16)
 | reverse | TCAGTGCTCTGACTGGCACT
 | | (SEQ ID NO:17)
region a (4048–5435) | forward | (T7)-ACGTTACATGAGCCAG
 | | (SEQ ID NO:3)
 | reverse | TCCAAATGTCATGATTTTCAC
 | | (SEQ ID NO:4)
region b (5282–6529) | forward | (T7)-CTGGCCTATCTACAGC
 | | (SEQ ID NO:5)
 | reverse | CAACCTGCTAAGTGTGGGAT
 | | (SEQ ID NO:6)
region c (6322–7856) | forward | (T7)-CAGTGGGACCATTGC
 | | (SEQ ID NO:7)
 | reverse | TTCTGACCATCTGAGGTCTCC
 | | (SEQ ID NO:8)
region d (7651–9172) | forward | (T7)-GATCACCCCATCACA
 | | (SEQ ID NO:9)
 | reverse | TCACACCCAAGCTTTCCATC
 | | (SEQ ID NO:10)
T7 | | GGATCCTAATACGACTCACTATAGGAACAG
 | | ACCACCATG
 | | (SEQ ID NO:11)
Exons | |
exon 12 | forward | GCTTACTTGGAGCCATAATTC
 | | (SEQ ID NO:18)
 | reverse | TGAAGGTCTGCAGGCTGAC
 | | (SEQ ID NO:19)
exon 24 | forward | TGGGAAAAGACTTTCCTGTAAA
 | | (SEQ ID NO:20)
 | reverse | CTATTGATTGACTCTGCAGCC
 | | (SEQ ID NO:21)
exon 41 | forward | CTCTATGCAGAAATCTATGCAG
 | | (SEQ ID NO:22)
 | reverse | ATACCCTTATTGAGACAATGCC
 | | (SEQ ID NO:23)
exon 42 | forward | GTATTCAGGAGCTTC
 | | (SEQ ID NO:24)
 | reverse | ATGGCATCTGTACAGTGTCT
 | | (SEQ ID NO:25)
exon 43 | forward | CAGAACTGTATTTCAGAATCAT
 | | (SEQ ID NO:26)
 | reverse | ACATAACTCCTTCATAAACAGA
 | | (SEQ ID NO:27)
exon 50 | forward | AGTTGGGTACAGTCATGGTA
 | | (SEQ ID NO:28)
 | reverse | GAAAAGATGAAGCATATTCATG
 | | (SEQ ID NO:29)
exon 53 | forward | TTACTTGCTTAGATGTGAGA
 | | (SEQ ID NO:30)
 | reverse | ATATGTTGGAATCTTCATTCCG
 | | (SEQ ID NO:31)
exon 54 | forward | AAGCAAAATGAAAAATATGG
 | | (SEQ ID NO:32)
 | reverse | AAGTGTGATGGGGGTGA
 | | (SEQ ID NO:33)

IV. Other Embodiments

Alterations in either the nucleotide sequence of the gene or the amino acid sequence of the protein may be assayed for diagnostic purposes in order to determine whether a mutation in accordance with the present invention exists. Alterations in the amino acid sequence may be probed by functional testing. Alterations in the nucleotide sequence may be probed by means of nucleotide probes or primers, or by restriction enzyme digestion, for example, as in the rapid assays reported herein.

A further application of the present invention features a transgenic non-human mammal (preferably a mouse). Since a gene equivalent to the ATM gene has been identified in mice, an animal model for human ataxia-telangiectasia is created. Mice are generated from embryonic stem cells in which the ATM gene is mutated by gene targeting. Mice homozygous for the mutated gene provide an invaluable means to study the nature of the disease and test potential therapies. See Snowwaert et al., Science 257: 1083–1088, 1992, describing an animal model for cystic fibrosis, another autosomal recessive disease.

Another application of the present invention is in gene therapy. Gene therapy involves the transfer of genetic material into cells of a subject to correct a defect (Mulligan, Science 260: 926–931, 1993). Ex vivo gene therapy involves removal of the relevant target cells from the body, transduction of the cells in vitro, and subsequent reintroduction of the modified cells into the host. In contrast, in vivo gene therapy is a method in which genetic material is transferred directly into cells and tissues of the subject. Viral vectors are presently the most frequently used means for gene delivery. Such vectors include retrovirus vectors, adenovirus vectors, adeno-associated virus vectors, herpes virus vectors, vaccinia virus vectors, polio virus vectors, and sindbis and other RNA virus vectors. Nonviral methods of gene transfer have been reported for ligand-DNA conjugates, adenovirus-ligand-DNA conjugates, lipofection, naked DNA, and calcium phosphate precipitation. In preferred protocols, a mutant ATM gene is delivered into tumor cells by way of in vivo gene therapy, using viral or non-viral mediated methods. Those skilled in the art can adapt, for example, the Nabel et al. work to this application, which demonstrates gene therapy of malignancy by in vivo gene transfer into tumors. Nabel et al., Proc. Natl. Acad. Sci. USA 90: 11307–11311, 1993. Thus, for instance, tumor cells containing the mutant ATM gene can be made more sensitive to x-irradiation so that they may be selectively killed and normal cells spared during radiation treatment for cancer therapy.

EXAMPLES

Particular aspects of the invention may be more readily understood by reference to the following examples, which are intended to exemplify the invention, without limiting its scope to the particular exemplified embodiments.

Example 1

Patients: Forty-eight unrelated AT patients from different populations (American, Polish, Turkish, Italian, Irish, and Australian) were screened.

Preparation of cDNA: Total RNA was isolated from lymphoblastoid cell lines (LCLs) using a guanidinium thiocyanate-phenol-chloroform single-step extraction (Chomczynski et al., Anal Biochem 162: 156–159, 1987). The LCLs were derived from peripheral blood lymphocytes of patients by Epstein-Barr virus transformation (Svedmyr et al., Tissue Antigens 5: 186–195, 1975). First strand CDNA was prepared in a total volume of 50 ul containing 15 ug total RNA, 1x first strand buffer (Gibco BRL), 10 mM DTT, 3 mM dNTP, 1.25 ug oligo d(T)18 primer, 0.1 A260 units random hexamer primer (Pharmacia Biotech), 36 units RNase Inhibitor, 200 units Moloney Murine Leukemia Virus reverse transcriptase. The reaction mixture was incubated at 37° C. for 1 hour, and 2–3 ul was used as a PCR template.

Primers: The 3' region of the ATM gene was divided into four overlapping regions: a (1408 bp), b (1290 bp), c (1573 bp), and d (1560 bp). Forward primers were designed to include a T7 promoter sequence for the initiation of transcription by T7 RNA polymerase, as well as consensus sequence for the initiation of translation. The primer sequences used were: for region a, [F] (T7)-ACG TTA CAT GAG CCAG (SEQ ID NO:3) and [R] TCC AAA TGT CAT GAT TTT CAC (SEQ ID NO:4); for region b, [F] (T7)-CTG GCC TAT CTA CAGC (SEQ ID NO:5) and [R] CAA CCT GCT AAG TGT GGG AT(SEQ ID NO:6); for region c, [F] (T7)-CAG TGG GAC CAT TGC (SEQ ID NO:7) and [R] TTC TGA CCA TCT GAG GTC TCC (SEQ ID NO:8); for region d, [F] (T7)-GAT CAC CCC CAT CACA (SEQ ID NO:9) and [R] TCA CAC CCA AGC TTT CCA TC (SEQ ID NO:10); and for [T7], GGA TCC TAA TAC GAC TCA CTA TAG GAA CAG ACC ACC ATG (SEQ ID NO:11).

RT-PCR: PCR of each region was performed for 30 cycles in a total volume of 15 ul, the mixture containing 1x PCR buffer (Perkin Elmer), 0.7 mM dNTP, 50 ng of each primer, and 2 units Taq DNA polymerase. Each cycle consisted of a denaturation step at 94° C. for 30 seconds, an annealing step (55° C. for regions a and b; 62° C. for regions c and d) for 30 seconds, and an extension step at 72° C. for 3 minutes.

PTT: 100 ng of RT-PCR product from each sample was used directly as template in a coupled transcription-translation reaction using rabbit reticulocytes, according to the protocol recommended by the manufacturer (Promega). Reactions were performed in 12.5 ul with 6 uCi of $^{35}$S-methionine. The translation products were separated through 14% discontinuous SDS-PAGE using 200 V for 3 hours. The gel was fixed, soaked in Amplify (Amersham) for 30 minutes, dried and placed on X-ray film.

Sequencing: PCR products were gel purified and manually sequenced with Sequenase Version 2.0, according to the protocol recommended by the manufacturer (USB).

Example 2

Cell Lines: A total of 38 cell lines, all derived from unrelated individuals, were assayed for variation in the ATM gene. Cell lines designated "AT#SE" (Seattle) have not been previously described and were derived from AT patients. Those designated "AT#LA" (Los Angeles) were from the UCLA Ataxia-Telangiectasia Research Laboratory and were derived from other patients. Cell lines designated with GM numbers were obtained from the National Institute of General Medical Sciences (NIGMS) Mutant Cell Repository. In some cases, isolates of the same cell line, obtained separately, were studied and were found concordant in all cases. All of the above were Epstein Barr virus-transformed lymphoblastoid cell lines. The SV40-transformed normal fibroblast cell lines LM217 and GM00637 and the AT fibroblast cell line AT5B1 were provided by Stanford Research Institute.

SSCP Analysis: RNA was prepared from cell lines by using Trizol reagent (Gibco-BRL) and protocols from the manufacturer. Randomly primed first-strand cDNA was prepared using Superscript II reverse transcriptase. Sets of PCR primers spaced 250–500 nt apart were used to amplify overlapping fragments of the ATM gene from cDNA. Amplifications were done in two stages, with the second amplification using hemi- or fully nested primers to ensure high specificity. Prior to SSCP analysis, all PCR products were examined by electrophoresis in 1.5% agarose gels. Larger deletions and insertions were usually visible at this stage. PCR products were then assayed for sequence variation by SSCP essentially as described by Orita et al., Genomics 5: 874–879, 1989. All samples were analyzed on 0.5x MDE gels both with and without glycerol (5%–10%).

Nucleotide Sequencing: Variant bands and, in some cases, normal bands identified in SSCP gels were individually excised from the gels. DNA was eluted from bands by soaking overnight in 10 mM Tris 7.0, reamplified, and sequenced using fluorescent dye terminators on an ABI 373A sequencer. All nucleotide sequences were determined on both strands.

Genomic DNA Assays: Confirmations of alterations detected in cDNA were carried out using genomic DNA as a template. Primers were synthesized such that they would amplify the exon of interest as well as 40 nt of flanking intronic sequence on each side of the exon. Intron nucleotide sequences flanking exons of interest were determined by sequencing long PCR products generated from a YAC clone containing the entire ATM gene. Variation in amplified exons was assessed by SSCP and nucleotide sequencing as done with cDNA templates or, in some cases, by cloning of the amplification product and nucleotide sequencing of a minimum of six independent clones.

Example 3

Patient Materials: Eight Norwegian families, 27 Costa Rican patients (previously described in Uhrhammer et al., Am J Hum Genet 57: 103–111, 1995), 22 Polish patients, 28 Italian patients, and several Mennonite/Amish families were studied (totalling 80 individuals). Approximately 150 cDNA and DNA samples from AT patients and 40 DNAs from normal persons were screened.

Primers: The ATM cDNA sequence was divided into seven overlapping fragments (a, b, c, d, e, f, and g) and each fragment was subjected to PTT. Primers used for the PTT analysis of the ATM gene are shown in Table 3. Primers used in rapid assays are also shown in Table 3.

Haplotype Analyses: A panel of 10–15 genetic markers were used to haplotype Norwegian, Costa Rican, Polish, Italian and Amish individuals.

Heteroduplex Analysis: Heteroduplexes were formed by mixing the PCR products of a patient with normal DNA. The DNA mixture was then denatured at 95° C. for five minutes and allowed to reanneal at 55° C. for 45 minutes. Samples were run on 12% polyacrylamide gel under nondenaturing conditions for 1.30 h. at 120 V. Bands were visualized by staining the gel with ethidium bromide.

RNA Isolation, cDNA Synthesis and PTT: These methods are described elsewhere herein. Protein products of the coupled-PTT reaction were run on 10–20% gradient SDS-PAGE gels for 5 h. at 250V.

While particular embodiments of the invention have been described in detail, it will be apparent to those skilled in the art that these embodiments are exemplary, rather than limiting. The true scope of the invention is that defined within the attached claims and equivalents thereof. All references cited herein are hereby expressly incorporated by reference.

What is claimed is:

1. An isolated ataxia telangiectasia mutated (ATM) gene, or the complement thereof, consisting of SEQ ID NO:1 and having a mutation, said mutation being a member selected from the group consisting of 4777 del 229 (c1592), 5650 del 8 (c1884), 6007 del 89 (c2003), 6015 ins C (c2005), 6100 C>T (c2034), 6372 ins G (c2124), 6404 ins TT (c2135), 6810 del C (c2271), 7009 del TG (c2337), 8266 A>T (c2756), 8672 del 115 (c2891), 8822 ins AACT (c2941), 8833 del CT (c2945), 8985 del 13 (c2995), 2251 del 19 (c750), 2251 del 217 (c750), 2639 del 283 (c880), 3078 del 207 (c1026), 3109 del 73 (c1037), 4638 del GATA (c1546), 5675 del 88 (c1892), 5763 ins 130 (c1921), 6096 del 103 (c2032), 6573 del 81 (c2191), 6976 del 114 (c2326), 7274 del 34 (c2425), 7327 C>T (c2443), 7926 A>C (c2642), ttattaa(t>g)agGA (c2597), 7792 C>T (c2598), 8150 A>G (c2671), 8152 del 117 (c2758), Costa Rican Haplotype, 3245 ATC>TGAT (c1081), 5908 del C (c1970), 7449 G>A (c2481 del 70), 6095 G>A (c2003 del 89), 7010 del GT (c2337), 5932 G>T (c1973 del 88), 3214 G>T (c1026 del 207), 432 ins A (c144), 3087 ins A (c1029), 8766 ins T (c2922), 1607 G>T (c536 ins 800), 2493 ins A (c835), 4612-12 A>G (c1538 ins 11), 8494 C>T (c2832), 8786 G>A (c2891 del 115), 2251-10 T>G (c750 ins 9), and 2810 ins CTAG (c937 ins 4).

2. The isolated gene, or complement thereof, of claim 1, said mutation being 4777 del 229 (c1592).

3. The isolated gene, or complement thereof, of claim 1, said mutation being 5650 del 8 (c1884).

4. The isolated gene, or complement thereof, of claim 1, said mutation being 6007 del 89 (c2003).

5. The isolated gene, or complement thereof, of claim 1, said mutation being 6015 ins C (c2005).

6. The isolated gene, or complement thereof, of claim 1, said mutation being 6100 C>T (c2034).

7. The isolated gene, or complement thereof, of claim 1, said mutation being 6372 ins G (c2124).

8. The isolated gene, or complement thereof, of claim 1, said mutation being 6404 ins TT (c2135).

9. The isolated gene, or complement thereof, of claim 1, said mutation being 6810 del C (c2271).

10. The isolated gene, or complement thereof, of claim 1, said mutation being 7009 del TG (c2337).

11. The isolated gene, or complement thereof, of claim 1, said mutation being 8266 A>T (c2756).

12. The isolated gene, or complement thereof, of claim 1, said mutation being 8672 del 115 (c2891).

13. The isolated gene, or complement thereof, of claim 1, said mutation being 8822 ins AACT (c2941).

14. The isolated gene, or complement thereof, of claim 1, said mutation being 8833 del CT (c2945).

15. The isolated gene, or complement thereof, of claim 1, said mutation being 8985 del 13 (c2995).

16. The isolated gene, or complement thereof, of claim 1, said mutation being 2251 del 19 (c750).

17. The isolated gene, or complement thereof, of claim 1, said mutation being 2251 del 217 (c750).

18. The isolated gene, or complement thereof, of claim 1, said mutation being 2639 del 283 (c880).

19. The isolated gene, or complement thereof, of claim 1, said mutation being 3078 del 207 (c1026).

20. The isolated gene, or complement thereof, of claim 1, said mutation being 3109 del 73 (c1037).

21. The isolated gene, or complement thereof, of claim 1, said mutation being 4638 del GATA (c1546).

22. The isolated gene, or complement thereof, of claim 1, said mutation being 5675 del 88 (c1892).

23. The isolated gene, or complement thereof, of claim 1, said mutation being 5763 ins 130 (c1921).

24. The isolated gene, or complement thereof of claim 1, said mutation being 6096 del 103 (c2032).

25. The isolated gene, or complement thereof, of claim 1, said mutation being 6573 del 81 (c2191).

26. The isolated gene, or complement thereof, of claim 1, said mutation being 6976 del 114 (c2326).

27. The isolated gene, or complement thereof, of claim 1, said mutation being 7274 del 34 (c2425).

28. The isolated gene, or complement thereof, of claim 1, said mutation being 7327 C>T (c2443).

29. The isolated gene, or complement thereof, of claim 1, said mutation being 7926 A>C (c2642).

30. The isolated gene, or complement thereof, of claim 1, said mutation being ttattaa(t>g)agGA (c2597).

31. The isolated gene, or complement thereof, of claim 1, said mutation being 7792 C>T (c2598).

32. The isolated gene, or complement thereof, of claim 1, said mutation being 8150 A>G (c2671).

33. The isolated gene, or complement thereof, of claim 1, said mutation being 8152 del 117 (c2758).

34. The isolated gene, or complement thereof, of claim 1, said mutation being Costa Rican Haplotype.

35. The isolated gene, or complement thereof, of claim 1, said mutation being 3245 ATC>TGAT (c1081).

36. The isolated gene, or complement thereof, of claim 1, said mutation being 5908 del C (c1970).

37. The isolated gene, or complement thereof, of claim 1, said mutation being 7449 G>A (c2481 del 70).

38. The isolated gene, or complement thereof, of claim 1, said mutation being 6095 G>A (c2003 del 89).

39. The isolated gene, or complement thereof, of claim 1, said mutation being 7010 del GT (c2337).

40. The isolated gene, or complement thereof, of claim 1, said mutation being 5932 G>T (c1973 del 88).

41. The isolated gene, or complement thereof, of claim 1, said mutation being 3214 G>T (c1026 del 207).

42. The isolated gene, or complement thereof, of claim 1, said mutation being 432 ins A (c144).

43. The isolated gene, or complement thereof, of claim 1, said mutation being 3087 ins A (c1029).

44. The isolated gene, or complement thereof, of claim 1, said mutation being 8766 ins T (c2922).

45. The isolated gene, or complement thereof, of claim 1, said mutation being 1607 G>T (c536 ins 800).

46. The isolated gene, or complement thereof, of claim 1, said mutation being 2493 ins A (c835).

47. The isolated gene, or complement thereof, of claim 1, said mutation being 4612-12 A>G (c1538 ins 11).

48. The isolated gene, or complement thereof, of claim 1, said mutation being 8494 C>T (c2832).

49. The isolated gene, or complement thereof, of claim 1, said mutation being 8786 G>A (c2891 del 115).

50. The isolated gene, or complement thereof, of claim 1, said mutation being 2251-10 T>G (c750 ins 9).

51. The isolated gene, or complement thereof, of claim 1, said mutation being 2810 ins CTAG (c937 ins 4).

52. A method of testing a DNA sample of a human for the presence of a mutation in the ATM gene, comprising:
providing a sample of DNA from a human, and
testing the sample for the presence of a mutation in the ATM gene, said mutation being a member selected from the group consisting of 4777 del 229 (c1592), 5650 del 8 (c1884), 6007 del 89 (c2003), 6015 ins C (c2005), 6100 C>T (c2034), 6372 ins G (c2124), 6404 ins TT (c2135), 6810 del C (c2271), 7009 del TG (c2337), 8266 A>T (c2756), 8672 del 115 (c2891), 8822 ins AACT (c2941), 8833 del CT (c2945), 8985 del 13 (c2995), 2251 del 19 (c750), 2251 del 217 (c750), 2639 del 283 (c880), 3078 del 207 (c1026), 3109 del 73 (c1037), 4638 del GATA (c1546), 5675 del 88 (c1892), 5763 ins 130 (c1921), 6096 del 103 (c2032), 6573 del 81 (c2191), 6976 del 114 (c2326), 7274 del 34 (c2425), 7327 C>T (c2443), 7926 A>C (c2642), ttattaa(t>g)agGA (c2597), 7792 C>T (c2598), 8150 A>G (c2671), 8152 del 117 (c2758), Costa Rican Haplotype, 3245 ATC>TGAT (c1081), 5908 del C (c1970), 7449 G>A (c2481 del 70), 6095 G>A (c2003 del 89), 7010 del GT (c2337), 5932 G>T (c1973 del 88), 3214 G>T (c1026 del 207), 432 ins A (c144), 3087 ins A (c1029), 8766 ins T (c2922), 1607 G>T (c536 ins 800), 2493 ins A (c835), 4612-12 A>G (c1538 ins 11), 8494 C>T (c2832), 8786 G>A (c2891 del 115), 2251-10 T>G (c750 ins 9), and 2810 ins CTAG (c937 ins 4).

53. The method of claim 52, said mutation being 4777 del 229 (c1592).

54. The method of claim 52, said mutation being 5650 del 8 (c1884).

55. The method of claim 52, said mutation being 6007 del 89 (c2003).

56. The method of claim 52, said mutation being 6015 ins C (c2005).

57. The method of claim 52, said mutation being 6100 C>T (c2034).

58. The method of claim 52, said mutation being 6372 ins G (c2124).

59. The method of claim 52, said mutation being 6404 ins TT (c2135).

60. The method of claim 52, said mutation being 6810 del C (c2271).

61. The method of claim 52, said mutation being 7009 del TG (c2337).

62. The method of claim 52, said mutation being 8266 A>T (c2756).

63. The method of claim 52, said mutation being 8672 del 115 (c2891).

64. The method of claim 52, said mutation being 8822 ins AACT (c2941).

65. The method of claim 52, said mutation being 8833 del CT (c2945).

66. The method of claim 52, said mutation being 8985 del 13 (c2995).

67. The method of claim 52, said mutation being 2251 del 19 (c750).

68. The method of claim 52, said mutation being 2251 del 217 (c750).

69. The method of claim 52, said mutation being 2639 del 283 (c880).

70. The method of claim 52, said mutation being 3078 del 207 (c1026).

71. The method of claim 52, said mutation being 3109 del 73 (c1037).

72. The method of claim 52, said mutation being 4638 del GATA (c1546).

73. The method of claim 52, said mutation being 5675 del 88 (c1892).

74. The method of claim 52, said mutation being 5763 ins 130 (c1921).

75. The method of claim 52, said mutation being 6096 del 103 (c2032).

76. The method of claim 52, said mutation being 6573 del 81 (c2191).

77. The method of claim 52, said mutation being 6976 del 114 (c2326).

78. The method of claim 52, said mutation being 7274 del 34 (c2425).

79. The method of claim 52, said mutation being 7327 C>T (c2443).

80. The method of claim 52, said mutation being 7926 A>C (c2642).

81. The method of claim 52, said mutation being ttattaa (t>g)agGA (c2597).

82. The method of claim 52, said mutation being 7792 C>T (c2598).

83. The method of claim 52, said mutation being 8150 A>G (c2671).

84. The method of claim 52, said mutation being 8152 del 117 (c2758).

85. The method of claim 52, said mutation being Costa Rican Haplotype.

86. The method of claim 52, said mutation being 3245 ATC>TGAT (c1081).

87. The method of claim 52, said mutation being 5908 del C (c1970).

88. The method of claim 52, said mutation being 7449 G>A (c2481 del 70).

89. The method of claim 52, said mutation being 6095 G>A (c2003 del 89).

90. The method of claim 52, said mutation being 7010 del GT (c2337).

91. The method of claim 52, said mutation being 5932 G>T (c1973 del 88).

92. The method of claim 52, said mutation being 3214 G>T (c1026 del 207).

93. The method of claim 52, said mutation being 432 ins A (c144).

94. The method of claim 52, said mutation being 3087 ins A (c1029).

95. The method of claim 52, said mutation being 8766 ins T (c2922).

96. The method of claim 52, said mutation being 1607 G>T (c536 ins 800).

97. The method of claim 52, said mutation being 2493 ins A (c835).

98. The method of claim 52, said mutation being 4612-12 A>G (c1538 ins 11).

99. The method of claim 52, said mutation being 8494 C>T (c2832).

100. The method of claim 52, said mutation being 8786 G>A (c2891 del 115).

101. The method of claim 52, said mutation being 2251-10 T>G (c750 ins 9).

102. The method of claim 52, said mutation being 2810 ins CTAG (c937 ins 4).

103. The method of claim 86, wherein the step of testing comprises PCR amplifying exon 24 of said gene with primers SEQ ID NO:20 and SEQ ID NO:21 in a sample of DNA from the human to form PCR products and subjecting the PCR products to heteroduplex analysis.

104. The method of claim 87, wherein the step of testing comprises PCR amplifying exon 41 of said gene with primers SEQ ID NO:22 and SEQ ID NO:23 in a sample of DNA from the human to form PCR products and subjecting the PCR products to restriction enzyme digestion analysis using Sau3A I.

105. The method of claim 89, wherein the step of testing comprises PCR amplifying exon 43 of said gene with primers SEQ ID NO:26 and SEQ ID NO:27 in a sample of DNA from the human to form PCR products and subjecting the PCR products to restriction enzyme digestion analysis using Bfa I.

106. The method of claim 90, wherein the step of testing comprises PCR amplifying exon 50 of said gene with primers SEQ ID NO:28 and SEQ ID NO:29 in a sample of DNA from the human to form PCR products and subjecting the PCR products to restriction enzyme digestion analysis using Tfi I.

107. The method of claim 91, wherein the step of testing comprises PCR amplifying exon 42 of said gene with primers SEQ ID NO:24 and SEQ ID NO:25 in a sample of DNA from the human to form PCR products and subjecting the PCR products to restriction enzyme digestion analysis using Mse I.

108. The method of claim 92, wherein the step of testing comprises PCR amplifying exon 24 of said gene with primers SEQ ID NO:20 and SEQ ID NO:21 in a sample of DNA from the human to form PCR products and subjecting the PCR products to restriction enzyme digestion analysis using Mse I.

* * * * *

SEQUENCE LISTING (1) GENERAL INFORMATION:

(iii) NUMBER OF SEQUENCES: 33

(2) INFORMATION FOR SEQ ID NO:1:

(i) SEQUENCE CHARACTERISTICS:
      (A) LENGTH: 9385 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 190...9357
      (D) OTHER INFORMATION:

(xi) SEQUENCE DESCRIPTION: SEQ ID NO:1:

```
GCGAGAGGAG TCGGGATCTG CGCTGCAGCC ACCGCCGCGG TTGATACTAC TTTGACCTTC    60

CGAGTGCAGT GAGGCATACA TCACAATTTG GAATTATGCA TTGGTTTATC AATTTACTTG   120

TTTATTGTCA CCCTGCTGCC CAGATATGAC TTCATGAGGA CAGTGATGTG TGTTCTGAAA   180

TTGTGAACC ATG AGT CTA GTA CTT AAT GAT CTG CTT ATC TGC TGC CGT CAA   231
           Met Ser Leu Val Leu Asn Asp Leu Leu Ile Cys Cys Arg Gln
             1               5                  10

CTA GAA CAT GAT AGA GCT ACA GAA CGA AAG AAA GAA GTT GAG AAA TTT    279
Leu Glu His Asp Arg Ala Thr Glu Arg Lys Lys Glu Val Glu Lys Phe
 15                  20                  25                  30

AAG CGC CTG ATT CGA GAT CCT GAA ACA ATT AAA CAT CTA GAT CGG CAT    327
Lys Arg Leu Ile Arg Asp Pro Glu Thr Ile Lys His Leu Asp Arg His
                     35                  40                  45

TCA GAT TCC AAA CAA GGA AAA TAT TTG AAT TGG GAT GCT GTT TTT AGA    375
Ser Asp Ser Lys Gln Gly Lys Tyr Leu Asn Trp Asp Ala Val Phe Arg
                 50                  55                  60

TTT TTA CAG AAA TAT ATT CAG AAA GAA ACA GAA TGT CTG AGA ATA GCA    423
Phe Leu Gln Lys Tyr Ile Gln Lys Glu Thr Glu Cys Leu Arg Ile Ala
             65                  70                  75
```

-continued

| | | |
|---|---|---|
| AAA CCA AAT GTA TCA GCC TCA ACA CAA GCC TCC AGG CAG AAA AAG ATG<br>Lys Pro Asn Val Ser Ala Ser Thr Gln Ala Ser Arg Gln Lys Lys Met<br>80                85                      90 | 471 |
| CAG GAA ATC AGT AGT TTG GTC AAA TAC TTC ATC AAA TGT GCA AAC AGA<br>Gln Glu Ile Ser Ser Leu Val Lys Tyr Phe Ile Lys Cys Ala Asn Arg<br>95                  100              105              110 | 519 |
| AGA GCA CCT AGG CTA AAA TGT CAA GAA CTC TTA AAT TAT ATC ATG GAT<br>Arg Ala Pro Arg Leu Lys Cys Gln Glu Leu Leu Asn Tyr Ile Met Asp<br>              115              120              125 | 567 |
| ACA GTG AAA GAT TCA TCT AAT GGT GCT ATT TAC GGA GCT GAT TGT AGC<br>Thr Val Lys Asp Ser Ser Asn Gly Ala Ile Tyr Gly Ala Asp Cys Ser<br>              130              135              140 | 615 |
| AAC ATA CTA CTC AAA GAC ATT CTT TCT GTG AGA AAA TAC TGG TGT GAA<br>Asn Ile Leu Leu Lys Asp Ile Leu Ser Val Arg Lys Tyr Trp Cys Glu<br>            145              150              155 | 663 |
| ATA TCT CAG CAA CAG TGG TTA GAA TTG TTC TCT GTG TAC TTC AGG CTC<br>Ile Ser Gln Gln Gln Trp Leu Glu Leu Phe Ser Val Tyr Phe Arg Leu<br>160                165              170 | 711 |
| TAT CTG AAA CCT TCA CAA GAT GTT CAT AGA GTT TTA GTG GCT AGA ATA<br>Tyr Leu Lys Pro Ser Gln Asp Val His Arg Val Leu Val Ala Arg Ile<br>175                180              185              190 | 759 |
| ATT CAT GCT GTT ACC AAA GGA TGC TGT TCT CAG ACT GAC GGA TTA AAT<br>Ile His Ala Val Thr Lys Gly Cys Cys Ser Gln Thr Asp Gly Leu Asn<br>              195              200              205 | 807 |
| TCC AAA TTT TTG GAC TTT TTT TCC AAG GCT ATT CAG TGT GCG AGA CAA<br>Ser Lys Phe Leu Asp Phe Phe Ser Lys Ala Ile Gln Cys Ala Arg Gln<br>            210              215              220 | 855 |
| GAA AAG AGC TCT TCA GGT CTA AAT CAT ATC TTA GCA GCT CTT ACT ATC<br>Glu Lys Ser Ser Ser Gly Leu Asn His Ile Leu Ala Ala Leu Thr Ile<br>        225              230              235 | 903 |
| TTC CTC AAG ACT TTG GCT GTC AAC TTT CGA ATT CGA GTG TGT GAA TTA<br>Phe Leu Lys Thr Leu Ala Val Asn Phe Arg Ile Arg Val Cys Glu Leu<br>240                245              250 | 951 |
| GGA GAT GAA ATT CTT CCC ACT TTG CTT TAT ATT TGG ACT CAA CAT AGG<br>Gly Asp Glu Ile Leu Pro Thr Leu Leu Tyr Ile Trp Thr Gln His Arg<br>255                260              265              270 | 999 |
| CTT AAT GAT TCT TTA AAA GAA GTC ATT ATT GAA TTA TTT CAA CTG CAA<br>Leu Asn Asp Ser Leu Lys Glu Val Ile Ile Glu Leu Phe Gln Leu Gln<br>              275              280              285 | 1047 |
| ATT TAT ATC CAT CAT CCG AAA GGA GCC AAA ACC CAA GAA AAA GGT GCT<br>Ile Tyr Ile His His Pro Lys Gly Ala Lys Thr Gln Glu Lys Gly Ala<br>            290              295              300 | 1095 |
| TAT GAA TCA ACA AAA TGG AGA AGT ATT TTA TAC AAC TTA TAT GAT CTG<br>Tyr Glu Ser Thr Lys Trp Arg Ser Ile Leu Tyr Asn Leu Tyr Asp Leu<br>        305              310              315 | 1143 |
| CTA GTG AAT GAG ATA AGT CAT ATA GGA AGT AGA GGA AAG TAT TCT TCA<br>Leu Val Asn Glu Ile Ser His Ile Gly Ser Arg Gly Lys Tyr Ser Ser<br>320                325              330 | 1191 |
| GGA TTT CGT AAT ATT GCC GTC AAA GAA AAT TTG ATT GAA TTG ATG GCA<br>Gly Phe Arg Asn Ile Ala Val Lys Glu Asn Leu Ile Glu Leu Met Ala<br>335                340              345              350 | 1239 |
| GAT ATC TGT CAC CAG GTT TTT AAT GAA GAT ACC AGA TCC TTG GAG ATT<br>Asp Ile Cys His Gln Val Phe Asn Glu Asp Thr Arg Ser Leu Glu Ile<br>            355              360              365 | 1287 |
| TCT CAA TCT TAC ACT ACT ACA CAA AGA GAA TCT AGT GAT TAC AGT GTC<br>Ser Gln Ser Tyr Thr Thr Thr Gln Arg Glu Ser Ser Asp Tyr Ser Val<br>              370              375              380 | 1335 |
| CCT TGC AAA AGG AAG AAA ATA GAA CTA GGC TGG GAA GTA ATA AAA GAT<br>Pro Cys Lys Arg Lys Lys Ile Glu Leu Gly Trp Glu Val Ile Lys Asp<br>        385              390              395 | 1383 |

```
CAC CTT CAG AAG TCA CAG AAT GAT TTT GAT CTT GTG CCT TGG CTA CAG     1431
His Leu Gln Lys Ser Gln Asn Asp Phe Asp Leu Val Pro Trp Leu Gln
        400                 405                 410

ATT GCA ACC CAA TTA ATA TCA AAG TAT CCT GCA AGT TTA CCT AAC TGT     1479
Ile Ala Thr Gln Leu Ile Ser Lys Tyr Pro Ala Ser Leu Pro Asn Cys
415                 420                 425                 430

GAG CTG TCT CCA TTA CTG ATG ATA CTA TCT CAG CTT CTA CCC CAA CAG     1527
Glu Leu Ser Pro Leu Leu Met Ile Leu Ser Gln Leu Leu Pro Gln Gln
                    435                 440                 445

CGA CAT GGG GAA CGT ACA CCA TAT GTG TTA CGA TGC CTT ACG GAA GTT     1575
Arg His Gly Glu Arg Thr Pro Tyr Val Leu Arg Cys Leu Thr Glu Val
        450                 455                 460

GCA TTG TGT CAA GAC AAG AGG TCA AAC CTA GAA AGC TCA CAA AAG TCA     1623
Ala Leu Cys Gln Asp Lys Arg Ser Asn Leu Glu Ser Ser Gln Lys Ser
465                 470                 475

GAT TTA TTA AAA CTC TGG AAT AAA ATT TGG TGT ATT ACC TTT CGT GGT     1671
Asp Leu Leu Lys Leu Trp Asn Lys Ile Trp Cys Ile Thr Phe Arg Gly
        480                 485                 490

ATA AGT TCT GAG CAA ATA CAA GCT GAA AAC TTT GGC TTA CTT GGA GCC     1719
Ile Ser Ser Glu Gln Ile Gln Ala Glu Asn Phe Gly Leu Leu Gly Ala
495                 500                 505                 510

ATA ATT CAG GGT AGT TTA GTT GAG GTT GAC AGA GAA TTC TGG AAG TTA     1767
Ile Ile Gln Gly Ser Leu Val Glu Val Asp Arg Glu Phe Trp Lys Leu
                    515                 520                 525

TTT ACT GGG TCA GCC TGC AGA CCT TCA TGT CCT GCA GTA TGC TGT TTG     1815
Phe Thr Gly Ser Ala Cys Arg Pro Ser Cys Pro Ala Val Cys Cys Leu
        530                 535                 540

ACT TTG GCA CTG ACC ACC AGT ATA GTT CCA GGA GCG GTA AAA ATG GGA     1863
Thr Leu Ala Leu Thr Thr Ser Ile Val Pro Gly Ala Val Lys Met Gly
545                 550                 555

ATA GAG CAA AAT ATG TGT GAA GTA AAT AGA AGC TTT TCT TTA AAG GAA     1911
Ile Glu Gln Asn Met Cys Glu Val Asn Arg Ser Phe Ser Leu Lys Glu
        560                 565                 570

TCA ATA ATG AAA TGG CTC TTA TTC TAT CAG TTA GAG GGT GAC TTA GAA     1959
Ser Ile Met Lys Trp Leu Leu Phe Tyr Gln Leu Glu Gly Asp Leu Glu
575                 580                 585                 590

AAT AGC ACA GAA GTG CCT CCA ATT CTT CAC AGT AAT TTT CCT CAT CTT     2007
Asn Ser Thr Glu Val Pro Pro Ile Leu His Ser Asn Phe Pro His Leu
                    595                 600                 605

GTA CTG GAG AAA ATT CTT GTG AGT CTC ACT ATG AAA AAC TGT AAA GCT     2055
Val Leu Glu Lys Ile Leu Val Ser Leu Thr Met Lys Asn Cys Lys Ala
        610                 615                 620

GCA ATG AAT TTT TTC CAA AGC GTG CCA GAA TGT GAA CAC CAC CAA AAA     2103
Ala Met Asn Phe Phe Gln Ser Val Pro Glu Cys Glu His His Gln Lys
625                 630                 635

GAT AAA GAA GAA CTT TCA TTC TCA GAA GTA GAA GAA CTA TTT CTT CAG     2151
Asp Lys Glu Glu Leu Ser Phe Ser Glu Val Glu Glu Leu Phe Leu Gln
        640                 645                 650

ACA ACT TTT GAC AAG ATG GAC TTT TTA ACC ATT GTG AGA GAA TGT GGT     2199
Thr Thr Phe Asp Lys Met Asp Phe Leu Thr Ile Val Arg Glu Cys Gly
655                 660                 665                 670

ATA GAA AAG CAC CAG TCC AGT ATT GGC TTC TCT GTC CAC CAG AAT CTC     2247
Ile Glu Lys His Gln Ser Ser Ile Gly Phe Ser Val His Gln Asn Leu
                    675                 680                 685

AAG GAA TCA CTG GAT CGC TGT CTT CTG GGA TTA TCA GAA CAG CTT CTG     2295
Lys Glu Ser Leu Asp Arg Cys Leu Leu Gly Leu Ser Glu Gln Leu Leu
        690                 695                 700

AAT AAT TAC TCA TCT GAG ATT ACA AAT TCA GAA ACT CTT GTC CGG TGT     2343
Asn Asn Tyr Ser Ser Glu Ile Thr Asn Ser Glu Thr Leu Val Arg Cys
705                 710                 715
```

```
TCA CGT CTT TTG GTG GGT GTC CTT GGC TGC TAC TGT TAC ATG GGT GTA    2391
Ser Arg Leu Leu Val Gly Val Leu Gly Cys Tyr Cys Tyr Met Gly Val
720                 725                 730

ATA GCT GAA GAG GAA GCA TAT AAG TCA GAA TTA TTC CAG AAA GCC AAC    2439
Ile Ala Glu Glu Glu Ala Tyr Lys Ser Glu Leu Phe Gln Lys Ala Asn
735                 740                 745                 750

TCT CTA ATG CAA TGT GCA GGA GAA AGT ATC ACT CTG TTT AAA AAT AAG    2487
Ser Leu Met Gln Cys Ala Gly Glu Ser Ile Thr Leu Phe Lys Asn Lys
                755                 760                 765

ACA AAT GAG GAA TTC AGA ATT GGT TCC TTG AGA AAT ATG ATG CAG CTA    2535
Thr Asn Glu Glu Phe Arg Ile Gly Ser Leu Arg Asn Met Met Gln Leu
        770                 775                 780

TGT ACA CGT TGC TTG AGC AAC TGT ACC AAG AAG AGT CCA AAT AAG ATT    2583
Cys Thr Arg Cys Leu Ser Asn Cys Thr Lys Lys Ser Pro Asn Lys Ile
            785                 790                 795

GCA TCT GGC TTT TTC CTG CGA TTG TTA ACA TCA AAG CTA ATG AAT GAC    2631
Ala Ser Gly Phe Phe Leu Arg Leu Leu Thr Ser Lys Leu Met Asn Asp
                800                 805                 810

ATT GCA GAT ATT TGT AAA AGT TTA GCA TCC TTC ATC AAA AAG CCA TTT    2679
Ile Ala Asp Ile Cys Lys Ser Leu Ala Ser Phe Ile Lys Lys Pro Phe
815                 820                 825                 830

GAC CGT GGA GAA GTA GAA TCA ATG GAA GAT GAT ACT AAT GGA AAT CTA    2727
Asp Arg Gly Glu Val Glu Ser Met Glu Asp Asp Thr Asn Gly Asn Leu
                835                 840                 845

ATG GAG GTG GAG GAT CAG TCA TCC ATG AAT CTA TTT AAC GAT TAC CCT    2775
Met Glu Val Glu Asp Gln Ser Ser Met Asn Leu Phe Asn Asp Tyr Pro
                850                 855                 860

GAT AGT AGT GTT AGT GAT GCA AAC GAA CCT GGA GAG AGC CAA AGT ACC    2823
Asp Ser Ser Val Ser Asp Ala Asn Glu Pro Gly Glu Ser Gln Ser Thr
            865                 870                 875

ATA GGT GCC ATT AAT CCT TTA GCT GAA GAA TAT CTG TCA AAG CAA GAT    2871
Ile Gly Ala Ile Asn Pro Leu Ala Glu Glu Tyr Leu Ser Lys Gln Asp
    880                 885                 890

CTA CTT TTC TTA GAC ATG CTC AAG TTC TTG TGT TTG TGT GTA ACT ACT    2919
Leu Leu Phe Leu Asp Met Leu Lys Phe Leu Cys Leu Cys Val Thr Thr
895                 900                 905                 910

GCT CAG ACC AAT ACT GTG TCC TTT AGG GCA GCT GAT ATT CGG AGG AAA    2967
Ala Gln Thr Asn Thr Val Ser Phe Arg Ala Ala Asp Ile Arg Arg Lys
                915                 920                 925

TTG TTA ATG TTA ATT GAT TCT AGC ACG CTA GAA CCT ACC AAA TCC CTC    3015
Leu Leu Met Leu Ile Asp Ser Ser Thr Leu Glu Pro Thr Lys Ser Leu
            930                 935                 940

CAC CTG CAT ATG TAT CTA ATG CTT TTA AAG GAG CTT CCT GGA GAA GAG    3063
His Leu His Met Tyr Leu Met Leu Leu Lys Glu Leu Pro Gly Glu Glu
        945                 950                 955

TAC CCC TTG CCA ATG GAA GAT GTT CTT GAA CTT CTG AAA CCA CTA TCC    3111
Tyr Pro Leu Pro Met Glu Asp Val Leu Glu Leu Leu Lys Pro Leu Ser
    960                 965                 970

AAT GTG TGT TCT TTG TAT CGT CGT GAC CAA GAT GTT TGT AAA ACT ATT    3159
Asn Val Cys Ser Leu Tyr Arg Arg Asp Gln Asp Val Cys Lys Thr Ile
975                 980                 985                 990

TTA AAC CAT GTC CTT CAT GTA GTG AAA AAC CTA GGT CAA AGC AAT ATG    3207
Leu Asn His Val Leu His Val Val Lys Asn Leu Gly Gln Ser Asn Met
                995                 1000                1005

GAC TCT GAG AAC ACA AGG GAT GCT CAA GGA CAG TTT CTT ACA GTA ATT    3255
Asp Ser Glu Asn Thr Arg Asp Ala Gln Gly Gln Phe Leu Thr Val Ile
            1010                1015                1020

GGA GCA TTT TGG CAT CTA ACA AAG GAG AGG AAA TAT ATA TTC TCT GTA    3303
Gly Ala Phe Trp His Leu Thr Lys Glu Arg Lys Tyr Ile Phe Ser Val
        1025                1030                1035
```

```
AGA ATG GCC CTA GTA AAT TGC CTT AAA ACT TTG CTT GAG GCT GAT CCT          3351
Arg Met Ala Leu Val Asn Cys Leu Lys Thr Leu Leu Glu Ala Asp Pro
         1040                1045                1050

TAT TCA AAA TGG GCC ATT CTT AAT GTA ATG GGA AAA GAC TTT CCT GTA          3399
Tyr Ser Lys Trp Ala Ile Leu Asn Val Met Gly Lys Asp Phe Pro Val
1055                1060                1065                1070

AAT GAA GTA TTT ACA CAA TTT CTT GCT GAC AAT CAT CAC CAA GTT CGC          3447
Asn Glu Val Phe Thr Gln Phe Leu Ala Asp Asn His His Gln Val Arg
              1075                1080                1085

ATG TTG GCT GCA GAG TCA ATC AAT AGA TTG TTC CAG GAC ACG AAG GGA          3495
Met Leu Ala Ala Glu Ser Ile Asn Arg Leu Phe Gln Asp Thr Lys Gly
         1090                1095                1100

GAT TCT TCC AGG TTA CTG AAA GCA CTT CCT TTG AAG CTT CAG CAA ACA          3543
Asp Ser Ser Arg Leu Leu Lys Ala Leu Pro Leu Lys Leu Gln Gln Thr
         1105                1110                1115

GCT TTT GAA AAT GCA TAC TTG AAA GCT CAG GAA GGA ATG AGA GAA ATG          3591
Ala Phe Glu Asn Ala Tyr Leu Lys Ala Gln Glu Gly Met Arg Glu Met
         1120                1125                1130

TCC CAT AGT GCT GAG AAC CCT GAA ACT TTG GAT GAA ATT TAT AAT AGA          3639
Ser His Ser Ala Glu Asn Pro Glu Thr Leu Asp Glu Ile Tyr Asn Arg
1135                1140                1145                1150

AAA TCT GTT TTA CTG ACG TTG ATA GCT GTG GTT TTA TCC TGT AGC CCT          3687
Lys Ser Val Leu Leu Thr Leu Ile Ala Val Val Leu Ser Cys Ser Pro
              1155                1160                1165

ATC TGC GAA AAA CAG GCT TTG TTT GCC CTG TGT AAA TCT GTG AAA GAG          3735
Ile Cys Glu Lys Gln Ala Leu Phe Ala Leu Cys Lys Ser Val Lys Glu
         1170                1175                1180

AAT GGA TTA GAA CCT CAC CTT GTG AAA AAG GTT TTA GAG AAA GTT TCT          3783
Asn Gly Leu Glu Pro His Leu Val Lys Lys Val Leu Glu Lys Val Ser
         1185                1190                1195

GAA ACT TTT GGA TAT AGA CGT TTA GAA GAC TTT ATG GCA TCT CAT TTA          3831
Glu Thr Phe Gly Tyr Arg Arg Leu Glu Asp Phe Met Ala Ser His Leu
1200                1205                1210

GAT TAT CTG GTT TTG GAA TGG CTA AAT CTT CAA GAT ACT GAA TAC AAC          3879
Asp Tyr Leu Val Leu Glu Trp Leu Asn Leu Gln Asp Thr Glu Tyr Asn
1215                1220                1225                1230

TTA TCT TCT TTT CCT TTT ATT TTA TTA AAC TAC ACA AAT ATT GAG GAT          3927
Leu Ser Ser Phe Pro Phe Ile Leu Leu Asn Tyr Thr Asn Ile Glu Asp
              1235                1240                1245

TTC TAT AGA TCT TGT TAT AAG GTT TTG ATT CCA CAT CTG GTG ATT AGA          3975
Phe Tyr Arg Ser Cys Tyr Lys Val Leu Ile Pro His Leu Val Ile Arg
         1250                1255                1260

AGT CAT TTT GAT GAG GTG AAG TCC ATT GCT AAT CAG ATT CAA GAG GAC          4023
Ser His Phe Asp Glu Val Lys Ser Ile Ala Asn Gln Ile Gln Glu Asp
         1265                1270                1275

TGG AAA AGT CTT CTA ACA GAC TGC TTT CCA AAG ATT CTT GTA AAT ATT          4071
Trp Lys Ser Leu Leu Thr Asp Cys Phe Pro Lys Ile Leu Val Asn Ile
         1280                1285                1290

CTT CCT TAT TTT GCC TAT GAG GGT ACC AGA GAC AGT GGG ATG GCA CAG          4119
Leu Pro Tyr Phe Ala Tyr Glu Gly Thr Arg Asp Ser Gly Met Ala Gln
1295                1300                1305                1310

CAA AGA GAG ACT GCT ACC AAG GTC TAT GAT ATG CTT AAA AGT GAA AAC          4167
Gln Arg Glu Thr Ala Thr Lys Val Tyr Asp Met Leu Lys Ser Glu Asn
              1315                1320                1325

TTA TTG GGA AAA CAG ATT GAT CAC TTA TTC ATT AGT AAT TTA CCA GAG          4215
Leu Leu Gly Lys Gln Ile Asp His Leu Phe Ile Ser Asn Leu Pro Glu
         1330                1335                1340

ATT GTG GTG GAG TTA TTG ATG ACG TTA CAT GAG CCA GCA AAT TCT AGT          4263
Ile Val Val Glu Leu Leu Met Thr Leu His Glu Pro Ala Asn Ser Ser
         1345                1350                1355
```

```
GCC AGT CAG AGC ACT GAC CTC TGT GAC TTT TCA GGG GAT TTG GAT CCT      4311
Ala Ser Gln Ser Thr Asp Leu Cys Asp Phe Ser Gly Asp Leu Asp Pro
            1360                1365                1370

GCT CCT AAT CCA CCT CAT TTT CCA TCG CAT GTG ATT AAA GCA ACA TTT      4359
Ala Pro Asn Pro Pro His Phe Pro Ser His Val Ile Lys Ala Thr Phe
1375                1380                1385                1390

GCC TAT ATC AGC AAT TGT CAT AAA ACC AAG TTA AAA AGC ATT TTA GAA      4407
Ala Tyr Ile Ser Asn Cys His Lys Thr Lys Leu Lys Ser Ile Leu Glu
                1395                1400                1405

ATT CTT TCC AAA AGC CCT GAT TCC TAT CAG AAA ATT CTT CTT GCC ATA      4455
Ile Leu Ser Lys Ser Pro Asp Ser Tyr Gln Lys Ile Leu Leu Ala Ile
            1410                1415                1420

TGT GAG CAA GCA GCT GAA ACA AAT AAT GTT TAT AAG AAG CAC AGA ATT      4503
Cys Glu Gln Ala Ala Glu Thr Asn Asn Val Tyr Lys Lys His Arg Ile
        1425                1430                1435

CTT AAA ATA TAT CAC CTG TTT GTT AGT TTA TTA CTG AAA GAT ATA AAA      4551
Leu Lys Ile Tyr His Leu Phe Val Ser Leu Leu Leu Lys Asp Ile Lys
    1440                1445                1450

AGT GGC TTA GGA GGA GCT TGG GCC TTT GTT CTT CGA GAC GTT ATT TAT      4599
Ser Gly Leu Gly Gly Ala Trp Ala Phe Val Leu Arg Asp Val Ile Tyr
1455                1460                1465                1470

ACT TTG ATT CAC TAT ATC AAC CAA AGG CCT TCT TGT ATC ATG GAT GTG      4647
Thr Leu Ile His Tyr Ile Asn Gln Arg Pro Ser Cys Ile Met Asp Val
                1475                1480                1485

TCA TTA CGT AGC TTC TCC CTT TGT TGT GAC TTA TTA AGT CAG GTT TGC      4695
Ser Leu Arg Ser Phe Ser Leu Cys Cys Asp Leu Leu Ser Gln Val Cys
            1490                1495                1500

CAG ACA GCC GTG ACT TAC TGT AAG GAT GCT CTA GAA AAC CAT CTT CAT      4743
Gln Thr Ala Val Thr Tyr Cys Lys Asp Ala Leu Glu Asn His Leu His
        1505                1510                1515

GTT ATT GTT GGT ACA CTT ATA CCC CTT GTG TAT GAG CAG GTG GAG GTT      4791
Val Ile Val Gly Thr Leu Ile Pro Leu Val Tyr Glu Gln Val Glu Val
    1520                1525                1530

CAG AAA CAG GTA TTG GAC TTG TTG AAA TAC TTA GTG ATA GAT AAC AAG      4839
Gln Lys Gln Val Leu Asp Leu Leu Lys Tyr Leu Val Ile Asp Asn Lys
1535                1540                1545                1550

GAT AAT GAA AAC CTC TAT ATC ACG ATT AAG CTT TTA GAT CCT TTT CCT      4887
Asp Asn Glu Asn Leu Tyr Ile Thr Ile Lys Leu Leu Asp Pro Phe Pro
                1555                1560                1565

GAC CAT GTT GTT TTT AAG GAT TTG CGT ATT ACT CAG CAA AAA ATC AAA      4935
Asp His Val Val Phe Lys Asp Leu Arg Ile Thr Gln Gln Lys Ile Lys
            1570                1575                1580

TAC AGT AGA GGA CCC TTT TCA CTC TTG GAG GAA ATT AAC CAT TTT CTC      4983
Tyr Ser Arg Gly Pro Phe Ser Leu Leu Glu Glu Ile Asn His Phe Leu
        1585                1590                1595

TCA GTA AGT GTT TAT GAT GCA CTT CCA TTG ACA AGA CTT GAA GGA CTA      5031
Ser Val Ser Val Tyr Asp Ala Leu Pro Leu Thr Arg Leu Glu Gly Leu
    1600                1605                1610

AAG GAT CTT CGA AGA CAA CTG GAA CTA CAT AAA GAT CAG ATG GTG GAC      5079
Lys Asp Leu Arg Arg Gln Leu Glu Leu His Lys Asp Gln Met Val Asp
1615                1620                1625                1630

ATT ATG AGA GCT TCT CAG GAT AAT CCG CAA GAT GGG ATT ATG GTG AAA      5127
Ile Met Arg Ala Ser Gln Asp Asn Pro Gln Asp Gly Ile Met Val Lys
                1635                1640                1645

CTA GTT GTC AAT TTG TTG CAG TTA TCC AAG ATG GCA ATA AAC CAC ACT      5175
Leu Val Val Asn Leu Leu Gln Leu Ser Lys Met Ala Ile Asn His Thr
            1650                1655                1660

GGT GAA AAA GAA GTT CTA GAG GCT GTT GGA AGC TGC TTG GGA GAA GTG      5223
Gly Glu Lys Glu Val Leu Glu Ala Val Gly Ser Cys Leu Gly Glu Val
        1665                1670                1675
```

```
GGT CCT ATA GAT TTC TCT ACC ATA GCT ATA CAA CAT AGT AAA GAT GCA    5271
Gly Pro Ile Asp Phe Ser Thr Ile Ala Ile Gln His Ser Lys Asp Ala
        1680                1685                1690

TCT TAT ACC AAG GCC CTT AAG TTA TTT GAA GAT AAA GAA CTT CAG TGG    5319
Ser Tyr Thr Lys Ala Leu Lys Leu Phe Glu Asp Lys Glu Leu Gln Trp
1695                1700                1705                1710

ACC TTC ATA ATG CTG ACC TAC CTG AAT AAC ACA CTG GTA GAA GAT TGT    5367
Thr Phe Ile Met Leu Thr Tyr Leu Asn Asn Thr Leu Val Glu Asp Cys
            1715                1720                1725

GTC AAA GTT CGA TCA GCA GCT GTT ACC TGT TTG AAA AAC ATT TTA GCC    5415
Val Lys Val Arg Ser Ala Ala Val Thr Cys Leu Lys Asn Ile Leu Ala
        1730                1735                1740

ACA AAG ACT GGA CAT AGT TTC TGG GAG ATT TAT AAG ATG ACA ACA GAT    5463
Thr Lys Thr Gly His Ser Phe Trp Glu Ile Tyr Lys Met Thr Thr Asp
            1745                1750                1755

CCA ATG CTG GCC TAT CTA CAG CCT TTT AGA ACA TCA AGA AAA AAG TTT    5511
Pro Met Leu Ala Tyr Leu Gln Pro Phe Arg Thr Ser Arg Lys Lys Phe
        1760                1765                1770

TTA GAA GTA CCC AGA TTT GAC AAA GAA AAC CCT TTT GAA GGC CTG GAT    5559
Leu Glu Val Pro Arg Phe Asp Lys Glu Asn Pro Phe Glu Gly Leu Asp
1775                1780                1785                1790

GAT ATA AAT CTG TGG ATT CCT CTA AGT GAA AAT CAT GAC ATT TGG ATA    5607
Asp Ile Asn Leu Trp Ile Pro Leu Ser Glu Asn His Asp Ile Trp Ile
            1795                1800                1805

AAG ACA CTG ACT TGT GCT TTT TTG GAC AGT GGA GGC ACA AAA TGT GAA    5655
Lys Thr Leu Thr Cys Ala Phe Leu Asp Ser Gly Gly Thr Lys Cys Glu
        1810                1815                1820

ATT CTT CAA TTA TTA AAG CCA ATG TGT GAA GTG AAA ACT GAC TTT TGT    5703
Ile Leu Gln Leu Leu Lys Pro Met Cys Glu Val Lys Thr Asp Phe Cys
        1825                1830                1835

CAG ACT GTA CTT CCA TAC TTG ATT CAT GAT ATT TTA CTC CAA GAT ACA    5751
Gln Thr Val Leu Pro Tyr Leu Ile His Asp Ile Leu Leu Gln Asp Thr
        1840                1845                1850

AAT GAA TCA TGG AGA AAT CTG CTT TCT ACA CAT GTT CAG GGA TTT TTC    5799
Asn Glu Ser Trp Arg Asn Leu Leu Ser Thr His Val Gln Gly Phe Phe
1855                1860                1865                1870

ACC AGC TGT CTT CGA CAC TTC TCG CAA ACG AGC CGA TCC ACA ACC CCT    5847
Thr Ser Cys Leu Arg His Phe Ser Gln Thr Ser Arg Ser Thr Thr Pro
            1875                1880                1885

GCA AAC TTG GAT TCA GAG TCA GAG CAC TTT TTC CGA TGC TGT TTG GAT    5895
Ala Asn Leu Asp Ser Glu Ser Glu His Phe Phe Arg Cys Cys Leu Asp
        1890                1895                1900

AAA AAA TCA CAA AGA ACA ATG CTT GCT GTT GTG GAC TAC ATG AGA AGA    5943
Lys Lys Ser Gln Arg Thr Met Leu Ala Val Val Asp Tyr Met Arg Arg
        1905                1910                1915

CAA AAG AGA CCT TCT TCA GGA ACA ATT TTT AAT GAT GCT TTC TGG CTG    5991
Gln Lys Arg Pro Ser Ser Gly Thr Ile Phe Asn Asp Ala Phe Trp Leu
        1920                1925                1930

GAT TTA AAT TAT CTA GAA GTT GCC AAG GTA GCT CAG TCT TGT GCT GCT    6039
Asp Leu Asn Tyr Leu Glu Val Ala Lys Val Ala Gln Ser Cys Ala Ala
1935                1940                1945                1950

CAC TTT ACA GCT TTA CTC TAT GCA GAA ATC TAT GCA GAT AAG AAA AGT    6087
His Phe Thr Ala Leu Leu Tyr Ala Glu Ile Tyr Ala Asp Lys Lys Ser
            1955                1960                1965

ATG GAT GAT CAA GAG AAA AGA AGT CTT GCA TTT GAA GAA GGA AGC CAG    6135
Met Asp Asp Gln Glu Lys Arg Ser Leu Ala Phe Glu Glu Gly Ser Gln
        1970                1975                1980

AGT ACA ACT ATT TCT AGC TTG AGT GAA AAA AGT AAA GAA GAA ACT GGA    6183
Ser Thr Thr Ile Ser Ser Leu Ser Glu Lys Ser Lys Glu Glu Thr Gly
        1985                1990                1995
```

```
ATA AGT TTA CAG GAT CTT CTC TTA GAA ATC TAC AGA AGT ATA GGG GAG      6231
Ile Ser Leu Gln Asp Leu Leu Leu Glu Ile Tyr Arg Ser Ile Gly Glu
2000                2005                2010

CCA GAT AGT TTG TAT GGC TGT GGT GGA GGG AAG ATG TTA CAA CCC ATT      6279
Pro Asp Ser Leu Tyr Gly Cys Gly Gly Gly Lys Met Leu Gln Pro Ile
2015                2020                2025                2030

ACT AGA CTA CGA ACA TAT GAA CAC GAA GCA ATG TGG GGC AAA GCC CTA      6327
Thr Arg Leu Arg Thr Tyr Glu His Glu Ala Met Trp Gly Lys Ala Leu
                2035                2040                2045

GTA ACA TAT GAC CTC GAA ACA GCA ATC CCC TCA TCA ACA CGC CAG GCA      6375
Val Thr Tyr Asp Leu Glu Thr Ala Ile Pro Ser Ser Thr Arg Gln Ala
        2050                2055                2060

GGA ATC ATT CAG GCC TTG CAG AAT TTG GGA CTC TGC CAT ATT CTT TCC      6423
Gly Ile Ile Gln Ala Leu Gln Asn Leu Gly Leu Cys His Ile Leu Ser
            2065                2070                2075

GTC TAT TTA AAA GGA TTG GAT TAT GAA AAT AAA GAC TGG TGT CCT GAA      6471
Val Tyr Leu Lys Gly Leu Asp Tyr Glu Asn Lys Asp Trp Cys Pro Glu
                2080                2085                2090

CTA GAA GAA CTT CAT TAC CAA GCA GCA TGG AGG AAT ATG CAG TGG GAC      6519
Leu Glu Glu Leu His Tyr Gln Ala Ala Trp Arg Asn Met Gln Trp Asp
2095                2100                2105                2110

CAT TGC ACT TCC GTC AGC AAA GAA GTA GAA GGA ACC AGT TAC CAT GAA      6567
His Cys Thr Ser Val Ser Lys Glu Val Glu Gly Thr Ser Tyr His Glu
                2115                2120                2125

TCA TTG TAC AAT GCT CTA CAA TCT CTA AGA GAC AGA GAA TTC TCT ACA      6615
Ser Leu Tyr Asn Ala Leu Gln Ser Leu Arg Asp Arg Glu Phe Ser Thr
        2130                2135                2140

TTT TAT GAA AGT CTC AAA TAT GCC AGA GTA AAA GAA GTG GAA GAG ATG      6663
Phe Tyr Glu Ser Leu Lys Tyr Ala Arg Val Lys Glu Val Glu Glu Met
            2145                2150                2155

TGT AAG CGC AGC CTT GAG TCT GTG TAT TCG CTC TAT CCC ACA CTT AGC      6711
Cys Lys Arg Ser Leu Glu Ser Val Tyr Ser Leu Tyr Pro Thr Leu Ser
    2160                2165                2170

AGG TTG CAG GCC ATT GGA GAG CTG GAA AGC ATT GGG GAG CTT TTC TCA      6759
Arg Leu Gln Ala Ile Gly Glu Leu Glu Ser Ile Gly Glu Leu Phe Ser
2175                2180                2185                2190

AGA TCA GTC ACA CAT AGA CAA CTC TCT GAA GTA TAT ATT AAG TGG CAG      6807
Arg Ser Val Thr His Arg Gln Leu Ser Glu Val Tyr Ile Lys Trp Gln
                2195                2200                2205

AAA CAC TCC CAG CTT CTC AAG GAC AGT GAT TTT AGT TTT CAG GAG CCT      6855
Lys His Ser Gln Leu Leu Lys Asp Ser Asp Phe Ser Phe Gln Glu Pro
            2210                2215                2220

ATC ATG GCT CTA CGC ACA GTC ATT TTG GAG ATC CTG ATG GAA AAG GAA      6903
Ile Met Ala Leu Arg Thr Val Ile Leu Glu Ile Leu Met Glu Lys Glu
                2225                2230                2235

ATG GAC AAC TCA CAA AGA GAA TGT ATT AAG GAC ATT CTC ACC AAA CAC      6951
Met Asp Asn Ser Gln Arg Glu Cys Ile Lys Asp Ile Leu Thr Lys His
    2240                2245                2250

CTT GTA GAA CTC TCT ATA CTG GCC AGA ACT TTC AAG AAC ACT CAG CTC      6999
Leu Val Glu Leu Ser Ile Leu Ala Arg Thr Phe Lys Asn Thr Gln Leu
2255                2260                2265                2270

CCT GAA AGG GCA ATA TTT CAA ATT AAA CAG TAC AAT TCA GTT AGC TGT      7047
Pro Glu Arg Ala Ile Phe Gln Ile Lys Gln Tyr Asn Ser Val Ser Cys
                2275                2280                2285

GGA GTC TCT GAG TGG CAG CTG GAA GAA GCA CAA GTA TTC TGG GCA AAA      7095
Gly Val Ser Glu Trp Gln Leu Glu Glu Ala Gln Val Phe Trp Ala Lys
            2290                2295                2300

AAG GAG CAG AGT CTT GCC CTG AGT ATT CTC AAG CAA ATG ATC AAG AAG      7143
Lys Glu Gln Ser Leu Ala Leu Ser Ile Leu Lys Gln Met Ile Lys Lys
                2305                2310                2315
```

```
TTG GAT GCC AGC TGT GCA GCG AAC AAT CCC AGC CTA AAA CTT ACA TAC    7191
Leu Asp Ala Ser Cys Ala Ala Asn Asn Pro Ser Leu Lys Leu Thr Tyr
2320                2325                2330

ACA GAA TGT CTG AGG GTT TGT GGC AAC TGG TTA GCA GAA ACG TGC TTA    7239
Thr Glu Cys Leu Arg Val Cys Gly Asn Trp Leu Ala Glu Thr Cys Leu
2335                2340                2345                2350

GAA AAT CCT GCG GTC ATC ATG CAG ACC TAT CTA GAA AAG GCA GTA GAA    7287
Glu Asn Pro Ala Val Ile Met Gln Thr Tyr Leu Glu Lys Ala Val Glu
            2355                2360                2365

GTT GCT GGA AAT TAT GAT GGA GAA AGT AGT GAT GAG CTA AGA AAT GGA    7335
Val Ala Gly Asn Tyr Asp Gly Glu Ser Ser Asp Glu Leu Arg Asn Gly
2370                2375                2380

AAA ATG AAG GCA TTT CTC TCA TTA GCC CGG TTT TCA GAT ACT CAA TAC    7383
Lys Met Lys Ala Phe Leu Ser Leu Ala Arg Phe Ser Asp Thr Gln Tyr
            2385                2390                2395

CAA AGA ATT GAA AAC TAC ATG AAA TCA TCG GAA TTT GAA AAC AAG CAA    7431
Gln Arg Ile Glu Asn Tyr Met Lys Ser Ser Glu Phe Glu Asn Lys Gln
        2400                2405                2410

GCT CTC CTG AAA AGA GCC AAA GAG GAA GTA GGT CTC CTT AGG GAA CAT    7479
Ala Leu Leu Lys Arg Ala Lys Glu Glu Val Gly Leu Leu Arg Glu His
2415                2420                2425                2430

AAA ATT CAG ACA AAC AGA TAC ACA GTA AAG GTT CAG CGA GAG CTG GAG    7527
Lys Ile Gln Thr Asn Arg Tyr Thr Val Lys Val Gln Arg Glu Leu Glu
            2435                2440                2445

TTG GAT GAA TTA GCC CTG CGT GCA CTG AAA GAG GAT CGT AAA CGC TTC    7575
Leu Asp Glu Leu Ala Leu Arg Ala Leu Lys Glu Asp Arg Lys Arg Phe
            2450                2455                2460

TTA TGT AAA GCA GTT GAA AAT TAT ATC AAC TGC TTA TTA AGT GGA GAA    7623
Leu Cys Lys Ala Val Glu Asn Tyr Ile Asn Cys Leu Leu Ser Gly Glu
            2465                2470                2475

GAA CAT GAT ATG TGG GTA TTC CGG CTT TGT TCC CTC TGG CTT GAA AAT    7671
Glu His Asp Met Trp Val Phe Arg Leu Cys Ser Leu Trp Leu Glu Asn
            2480                2485                2490

TCT GGA GTT TCT GAA GTC AAT GGC ATG ATG AAG AGA GAC GGA ATG AAG    7719
Ser Gly Val Ser Glu Val Asn Gly Met Met Lys Arg Asp Gly Met Lys
2495                2500                2505                2510

ATT CCA ACA TAT AAA TTT TTG CCT CTT ATG TAC CAA TTG GCT GCT AGA    7767
Ile Pro Thr Tyr Lys Phe Leu Pro Leu Met Tyr Gln Leu Ala Ala Arg
            2515                2520                2525

ATG GGG ACC AAG ATG ATG GGA GGC CTA GGA TTT CAT GAA GTC CTC AAT    7815
Met Gly Thr Lys Met Met Gly Gly Leu Gly Phe His Glu Val Leu Asn
            2530                2535                2540

AAT CTA ATC TCT AGA ATT TCA ATG GAT CAC CCC CAT CAC ACT TTG TTT    7863
Asn Leu Ile Ser Arg Ile Ser Met Asp His Pro His His Thr Leu Phe
            2545                2550                2555

ATT ATA CTG GCC TTA GCA AAT GCA AAC AGA GAT GAA TTT CTG ACT AAA    7911
Ile Ile Leu Ala Leu Ala Asn Ala Asn Arg Asp Glu Phe Leu Thr Lys
2560                2565                2570

CCA GAG GTA GCC AGA AGA AGC AGA ATA ACT AAA AAT GTG CCT AAA CAA    7959
Pro Glu Val Ala Arg Arg Ser Arg Ile Thr Lys Asn Val Pro Lys Gln
2575                2580                2585                2590

AGC TCT CAG CTT GAT GAG GAT CGA ACA GAG GCT GCA AAT AGA ATA ATA    8007
Ser Ser Gln Leu Asp Glu Asp Arg Thr Glu Ala Ala Asn Arg Ile Ile
            2595                2600                2605

TGT ACT ATC AGA AGT AGG AGA CCT CAG ATG GTC AGA AGT GTT GAG GCA    8055
Cys Thr Ile Arg Ser Arg Arg Pro Gln Met Val Arg Ser Val Glu Ala
            2610                2615                2620

CTT TGT GAT GCT TAT ATT ATA TTA GCA AAC TTA GAT GCC ACT CAG TGG    8103
Leu Cys Asp Ala Tyr Ile Ile Leu Ala Asn Leu Asp Ala Thr Gln Trp
            2625                2630                2635
```

```
AAG ACT CAG AGA AAA GGC ATA AAT ATT CCA GCA GAC CAG CCA ATT ACT     8151
Lys Thr Gln Arg Lys Gly Ile Asn Ile Pro Ala Asp Gln Pro Ile Thr
        2640                2645                2650

AAA CTT AAG AAT TTA GAA GAT GTT GTT GTC CCT ACT ATG GAA ATT AAG     8199
Lys Leu Lys Asn Leu Glu Asp Val Val Val Pro Thr Met Glu Ile Lys
2655                2660                2665                2670

GTG GAC CAC ACA GGA GAA TAT GGA AAT CTG GTG ACT ATA CAG TCA TTT     8247
Val Asp His Thr Gly Glu Tyr Gly Asn Leu Val Thr Ile Gln Ser Phe
        2675                2680                2685

AAA GCA GAA TTT CGC TTA GCA GGA GGT GTA AAT TTA CCA AAA ATA ATA     8295
Lys Ala Glu Phe Arg Leu Ala Gly Gly Val Asn Leu Pro Lys Ile Ile
        2690                2695                2700

GAT TGT GTA GGT TCC GAT GGC AAG GAG AGG AGA CAG CTT GTT AAG GGC     8343
Asp Cys Val Gly Ser Asp Gly Lys Glu Arg Arg Gln Leu Val Lys Gly
        2705                2710                2715

CGT GAT GAC CTG AGA CAA GAT GCT GTC ATG CAA CAG GTC TTC CAG ATG     8391
Arg Asp Asp Leu Arg Gln Asp Ala Val Met Gln Gln Val Phe Gln Met
        2720                2725                2730

TGT AAT ACA TTA CTG CAG AGA AAC ACG GAA ACT AGG AAG AGG AAA TTA     8439
Cys Asn Thr Leu Leu Gln Arg Asn Thr Glu Thr Arg Lys Arg Lys Leu
2735                2740                2745                2750

ACT ATC TGT ACT TAT AAG GTG GTT CCC CTC TCT CAG CGA AGT GGT GTT     8487
Thr Ile Cys Thr Tyr Lys Val Val Pro Leu Ser Gln Arg Ser Gly Val
        2755                2760                2765

CTT GAA TGG TGC ACA GGA ACT GTC CCC ATT GGT GAA TTT CTT GTT AAC     8535
Leu Glu Trp Cys Thr Gly Thr Val Pro Ile Gly Glu Phe Leu Val Asn
        2770                2775                2780

AAT GAA GAT GGT GCT CAT AAA AGA TAC AGG CCA AAT GAT TTC AGT GCC     8583
Asn Glu Asp Gly Ala His Lys Arg Tyr Arg Pro Asn Asp Phe Ser Ala
        2785                2790                2795

TTT CAG TGC CAA AAG AAA ATG ATG GAG GTG CAA AAA AAG TCT TTT GAA     8631
Phe Gln Cys Gln Lys Lys Met Met Glu Val Gln Lys Lys Ser Phe Glu
        2800                2805                2810

GAG AAA TAT GAA GTC TTC ATG GAT GTT TGC CAA AAT TTT CAA CCA GTT     8679
Glu Lys Tyr Glu Val Phe Met Asp Val Cys Gln Asn Phe Gln Pro Val
2815                2820                2825                2830

TTC CGT TAC TTC TGC ATG GAA AAA TTC TTG GAT CCA GCT ATT TGG TTT     8727
Phe Arg Tyr Phe Cys Met Glu Lys Phe Leu Asp Pro Ala Ile Trp Phe
        2835                2840                2845

GAG AAG CGA TTG GCT TAT ACG CGC AGT GTA GCT ACT TCT TCT ATT GTT     8775
Glu Lys Arg Leu Ala Tyr Thr Arg Ser Val Ala Thr Ser Ser Ile Val
        2850                2855                2860

GGT TAC ATA CTT GGA CTT GGT GAT AGA CAT GTA CAG AAT ATC TTG ATA     8823
Gly Tyr Ile Leu Gly Leu Gly Asp Arg His Val Gln Asn Ile Leu Ile
        2865                2870                2875

AAT GAG CAG TCA GCA GAA CTT GTA CAT ATA GAT CTA GGT GTT GCT TTT     8871
Asn Glu Gln Ser Ala Glu Leu Val His Ile Asp Leu Gly Val Ala Phe
        2880                2885                2890

GAA CAG GGC AAA ATC CTT CCT ACT CCT GAG ACA GTT CCT TTT AGA CTC     8919
Glu Gln Gly Lys Ile Leu Pro Thr Pro Glu Thr Val Pro Phe Arg Leu
2895                2900                2905                2910

ACC AGA GAT ATT GTG GAT GGC ATG GGC ATT ACG GGT GTT GAA GGT GTC     8967
Thr Arg Asp Ile Val Asp Gly Met Gly Ile Thr Gly Val Glu Gly Val
        2915                2920                2925

TTC AGA AGA TGC TGT GAG AAA ACC ATG GAA GTG ATG AGA AAC TCT CAG     9015
Phe Arg Arg Cys Cys Glu Lys Thr Met Glu Val Met Arg Asn Ser Gln
        2930                2935                2940

GAA ACT CTG TTA ACC ATT GTA GAG GTC CTT CTA TAT GAT CCA CTC TTT     9063
Glu Thr Leu Leu Thr Ile Val Glu Val Leu Leu Tyr Asp Pro Leu Phe
        2945                2950                2955
```

```
GAC TGG ACC ATG AAT CCT TTG AAA GCT TTG TAT TTA CAG CAG AGG CCG    9111
Asp Trp Thr Met Asn Pro Leu Lys Ala Leu Tyr Leu Gln Gln Arg Pro
    2960            2965                2970

GAA GAT GAA ACT GAG CTT CAC CCT ACT CTG AAT GCA GAT GAC CAA GAA    9159
Glu Asp Glu Thr Glu Leu His Pro Thr Leu Asn Ala Asp Asp Gln Glu
2975                2980                2985                2990

TGC AAA CGA AAT CTC AGT GAT ATT GAC CAG AGT TTC GAC AAA GTA GCT    9207
Cys Lys Arg Asn Leu Ser Asp Ile Asp Gln Ser Phe Asp Lys Val Ala
            2995                3000                3005

GAA CGT GTC TTA ATG AGA CTA CAA GAG AAA CTG AAA GGA GTG GAA GAA    9255
Glu Arg Val Leu Met Arg Leu Gln Glu Lys Leu Lys Gly Val Glu Glu
        3010                3015                3020

GGC ACT GTG CTC AGT GTT GGT GGA CAG GTG AAT TTG CTC ATA CAG CAG    9303
Gly Thr Val Leu Ser Val Gly Gly Gln Val Asn Leu Leu Ile Gln Gln
    3025                3030                3035

GCC ATA GAC CCC AAA AAT CTC AGC CGA CTT TTC CCA GGA TGG AAA GCT    9351
Ala Ile Asp Pro Lys Asn Leu Ser Arg Leu Phe Pro Gly Trp Lys Ala
    3040                3045                3050

TGG GTG TGATCTTCAG TATATGAATT ACCCTTTC                             9385
Trp Val
3055

(2) INFORMATION FOR SEQ ID NO:2:

(i) SEQUENCE CHARACTERISTICS:
        (A) LENGTH: 3056 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

Met Ser Leu Val Leu Asn Asp Leu Leu Ile Cys Cys Arg Gln Leu Glu
 1               5                  10                  15

His Asp Arg Ala Thr Glu Arg Lys Lys Glu Val Glu Lys Phe Lys Arg
                20                  25                  30

Leu Ile Arg Asp Pro Glu Thr Ile Lys His Leu Asp Arg His Ser Asp
            35                  40                  45

Ser Lys Gln Gly Lys Tyr Leu Asn Trp Asp Ala Val Phe Arg Phe Leu
50                  55                  60

Gln Lys Tyr Ile Gln Lys Glu Thr Glu Cys Leu Arg Ile Ala Lys Pro
65                  70                  75                  80

Asn Val Ser Ala Ser Thr Gln Ala Ser Arg Gln Lys Lys Met Gln Glu
                85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190
```

```
Ala Val Thr Lys Gly Cys Cys Ser Gln Thr Asp Gly Leu Asn Ser Lys
        195             200             205

Phe Leu Asp Phe Ser Lys Ala Ile Gln Cys Ala Arg Gln Glu Lys
    210             215             220

Ser Ser Ser Gly Leu Asn His Ile Leu Ala Ala Leu Thr Ile Phe Leu
225             230             235             240

Lys Thr Leu Ala Val Asn Phe Arg Ile Arg Val Cys Glu Leu Gly Asp
            245             250             255

Glu Ile Leu Pro Thr Leu Leu Tyr Ile Trp Thr Gln His Arg Leu Asn
        260             265             270

Asp Ser Leu Lys Glu Val Ile Ile Glu Leu Phe Gln Leu Gln Ile Tyr
        275             280             285

Ile His His Pro Lys Gly Ala Lys Thr Gln Glu Lys Gly Ala Tyr Glu
    290             295             300

Ser Thr Lys Trp Arg Ser Ile Leu Tyr Asn Leu Tyr Asp Leu Leu Val
305             310             315             320

Asn Glu Ile Ser His Ile Gly Ser Arg Gly Lys Tyr Ser Ser Gly Phe
            325             330             335

Arg Asn Ile Ala Val Lys Glu Asn Leu Ile Glu Leu Met Ala Asp Ile
        340             345             350

Cys His Gln Val Phe Asn Glu Asp Thr Arg Ser Leu Glu Ile Ser Gln
    355             360             365

Ser Tyr Thr Thr Thr Gln Arg Glu Ser Ser Asp Tyr Ser Val Pro Cys
370             375             380

Lys Arg Lys Lys Ile Glu Leu Gly Trp Glu Val Ile Lys Asp His Leu
385             390             395             400

Gln Lys Ser Gln Asn Asp Phe Asp Leu Val Pro Trp Leu Gln Ile Ala
            405             410             415

Thr Gln Leu Ile Ser Lys Tyr Pro Ala Ser Leu Pro Asn Cys Glu Leu
        420             425             430

Ser Pro Leu Leu Met Ile Leu Ser Gln Leu Leu Pro Gln Gln Arg His
    435             440             445

Gly Glu Arg Thr Pro Tyr Val Leu Arg Cys Leu Thr Glu Val Ala Leu
450             455             460

Cys Gln Asp Lys Arg Ser Asn Leu Glu Ser Ser Gln Lys Ser Asp Leu
465             470             475             480

Leu Lys Leu Trp Asn Lys Ile Trp Cys Ile Thr Phe Arg Gly Ile Ser
            485             490             495

Ser Glu Gln Ile Gln Ala Glu Asn Phe Gly Leu Leu Gly Ala Ile Ile
        500             505             510

Gln Gly Ser Leu Val Glu Val Asp Arg Glu Phe Trp Lys Leu Phe Thr
    515             520             525

Gly Ser Ala Cys Arg Pro Ser Cys Pro Ala Val Cys Cys Leu Thr Leu
530             535             540

Ala Leu Thr Thr Ser Ile Val Pro Gly Ala Val Lys Met Gly Ile Glu
545             550             555             560

Gln Asn Met Cys Glu Val Asn Arg Ser Phe Ser Leu Lys Glu Ser Ile
            565             570             575

Met Lys Trp Leu Leu Phe Tyr Gln Leu Glu Gly Asp Leu Glu Asn Ser
        580             585             590

Thr Glu Val Pro Pro Ile Leu His Ser Asn Phe Pro His Leu Val Leu
    595             600             605

Glu Lys Ile Leu Val Ser Leu Thr Met Lys Asn Cys Lys Ala Ala Met
610             615             620
```

```
Asn Phe Phe Gln Ser Val Pro Glu Cys Glu His His Gln Lys Asp Lys
625                 630                 635                 640

Glu Glu Leu Ser Phe Ser Glu Val Glu Leu Phe Leu Gln Thr Thr
            645                 650                 655

Phe Asp Lys Met Asp Phe Leu Thr Ile Val Arg Glu Cys Gly Ile Glu
                660                 665                 670

Lys His Gln Ser Ser Ile Gly Phe Ser Val His Gln Asn Leu Lys Glu
            675                 680                 685

Ser Leu Asp Arg Cys Leu Leu Gly Leu Ser Glu Gln Leu Leu Asn Asn
            690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Asn Ser Leu
            740                 745                 750

Met Gln Cys Ala Gly Glu Ser Ile Thr Leu Phe Lys Asn Lys Thr Asn
            755                 760                 765

Glu Glu Phe Arg Ile Gly Ser Leu Arg Asn Met Met Gln Leu Cys Thr
            770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
                820                 825                 830

Gly Glu Val Glu Ser Met Glu Asp Asp Thr Asn Gly Asn Leu Met Glu
            835                 840                 845

Val Glu Asp Gln Ser Ser Met Asn Leu Phe Asn Asp Tyr Pro Asp Ser
850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
                900                 905                 910

Thr Asn Thr Val Ser Phe Arg Ala Ala Asp Ile Arg Arg Lys Leu Leu
            915                 920                 925

Met Leu Ile Asp Ser Ser Thr Leu Glu Pro Thr Lys Ser Leu His Leu
930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
                980                 985                 990

His Val Leu His Val Val Lys Asn Leu Gly Gln Ser Asn Met Asp Ser
            995                 1000                1005

Glu Asn Thr Arg Asp Ala Gln Gly Gln Phe Leu Thr Val Ile Gly Ala
    1010                1015                1020

Phe Trp His Leu Thr Lys Glu Arg Lys Tyr Ile Phe Ser Val Arg Met
025                 1030                1035                1040

Ala Leu Val Asn Cys Leu Lys Thr Leu Leu Glu Ala Asp Pro Tyr Ser
```

-continued

```
                    1045                1050                1055
Lys Trp Ala Ile Leu Asn Val Met Gly Lys Asp Phe Pro Val Asn Glu
             1060                1065                1070

Val Phe Thr Gln Phe Leu Ala Asp Asn His His Gln Val Arg Met Leu
     1075                1080                1085

Ala Ala Glu Ser Ile Asn Arg Leu Phe Gln Asp Thr Lys Gly Asp Ser
         1090                1095                1100

Ser Arg Leu Leu Lys Ala Leu Pro Leu Lys Leu Gln Gln Thr Ala Phe
1105                1110                1115                1120

Glu Asn Ala Tyr Leu Lys Ala Gln Glu Gly Met Arg Glu Met Ser His
             1125                1130                1135

Ser Ala Glu Asn Pro Glu Thr Leu Asp Glu Ile Tyr Asn Arg Lys Ser
         1140                1145                1150

Val Leu Leu Thr Leu Ile Ala Val Val Leu Ser Cys Ser Pro Ile Cys
         1155                1160                1165

Glu Lys Gln Ala Leu Phe Ala Leu Cys Lys Ser Val Lys Glu Asn Gly
     1170                1175                1180

Leu Glu Pro His Leu Val Lys Lys Val Leu Glu Lys Val Ser Glu Thr
1185                1190                1195                1200

Phe Gly Tyr Arg Arg Leu Glu Asp Phe Met Ala Ser His Leu Asp Tyr
             1205                1210                1215

Leu Val Leu Glu Trp Leu Asn Leu Gln Asp Thr Glu Tyr Asn Leu Ser
         1220                1225                1230

Ser Phe Pro Phe Ile Leu Leu Asn Tyr Thr Asn Ile Glu Asp Phe Tyr
         1235                1240                1245

Arg Ser Cys Tyr Lys Val Leu Ile Pro His Leu Val Ile Arg Ser His
     1250                1255                1260

Phe Asp Glu Val Lys Ser Ile Ala Asn Gln Ile Gln Glu Asp Trp Lys
1265                1270                1275                1280

Ser Leu Leu Thr Asp Cys Phe Pro Lys Ile Leu Val Asn Ile Leu Pro
             1285                1290                1295

Tyr Phe Ala Tyr Glu Gly Thr Arg Asp Ser Gly Met Ala Gln Gln Arg
         1300                1305                1310

Glu Thr Ala Thr Lys Val Tyr Asp Met Leu Lys Ser Glu Asn Leu Leu
         1315                1320                1325

Gly Lys Gln Ile Asp His Leu Phe Ile Ser Asn Leu Pro Glu Ile Val
     1330                1335                1340

Val Glu Leu Leu Met Thr Leu His Glu Pro Ala Asn Ser Ser Ala Ser
1345                1350                1355                1360

Gln Ser Thr Asp Leu Cys Asp Phe Ser Gly Asp Leu Asp Pro Ala Pro
             1365                1370                1375

Asn Pro Pro His Phe Pro Ser His Val Ile Lys Ala Thr Phe Ala Tyr
         1380                1385                1390

Ile Ser Asn Cys His Lys Thr Lys Leu Lys Ser Ile Leu Glu Ile Leu
         1395                1400                1405

Ser Lys Ser Pro Asp Ser Tyr Gln Lys Ile Leu Leu Ala Ile Cys Glu
     1410                1415                1420

Gln Ala Ala Glu Thr Asn Asn Val Tyr Lys Lys His Arg Ile Leu Lys
1425                1430                1435                1440

Ile Tyr His Leu Phe Val Ser Leu Leu Leu Lys Asp Ile Lys Ser Gly
             1445                1450                1455

Leu Gly Gly Ala Trp Ala Phe Val Leu Arg Asp Val Ile Tyr Thr Leu
         1460                1465                1470
```

-continued

Ile His Tyr Ile Asn Gln Arg Pro Ser Cys Ile Met Asp Val Ser Leu
            1475                1480                1485

Arg Ser Phe Ser Leu Cys Cys Asp Leu Leu Ser Gln Val Cys Gln Thr
    1490                1495                1500

Ala Val Thr Tyr Cys Lys Asp Ala Leu Glu Asn His Leu His Val Ile
1505                1510                1515                1520

Val Gly Thr Leu Ile Pro Leu Val Tyr Glu Gln Val Glu Val Gln Lys
        1525                1530                1535

Gln Val Leu Asp Leu Leu Lys Tyr Leu Val Ile Asp Asn Lys Asp Asn
            1540                1545                1550

Glu Asn Leu Tyr Ile Thr Ile Lys Leu Leu Asp Pro Phe Pro Asp His
        1555                1560                1565

Val Val Phe Lys Asp Leu Arg Ile Thr Gln Gln Lys Ile Lys Tyr Ser
    1570                1575                1580

Arg Gly Pro Phe Ser Leu Leu Glu Glu Ile Asn His Phe Leu Ser Val
1585                1590                1595                1600

Ser Val Tyr Asp Ala Leu Pro Leu Thr Arg Leu Glu Gly Leu Lys Asp
        1605                1610                1615

Leu Arg Arg Gln Leu Glu Leu His Lys Asp Gln Met Val Asp Ile Met
            1620                1625                1630

Arg Ala Ser Gln Asp Asn Pro Gln Asp Gly Ile Met Val Lys Leu Val
        1635                1640                1645

Val Asn Leu Leu Gln Leu Ser Lys Met Ala Ile Asn His Thr Gly Glu
    1650                1655                1660

Lys Glu Val Leu Glu Ala Val Gly Ser Cys Leu Gly Glu Val Gly Pro
1665                1670                1675                1680

Ile Asp Phe Ser Thr Ile Ala Ile Gln His Ser Lys Asp Ala Ser Tyr
        1685                1690                1695

Thr Lys Ala Leu Lys Leu Phe Glu Asp Lys Glu Leu Gln Trp Thr Phe
            1700                1705                1710

Ile Met Leu Thr Tyr Leu Asn Asn Thr Leu Val Glu Asp Cys Val Lys
        1715                1720                1725

Val Arg Ser Ala Ala Val Thr Cys Leu Lys Asn Ile Leu Ala Thr Lys
    1730                1735                1740

Thr Gly His Ser Phe Trp Glu Ile Tyr Lys Met Thr Thr Asp Pro Met
1745                1750                1755                1760

Leu Ala Tyr Leu Gln Pro Phe Arg Thr Ser Arg Lys Lys Phe Leu Glu
        1765                1770                1775

Val Pro Arg Phe Asp Lys Glu Asn Pro Phe Glu Gly Leu Asp Asp Ile
            1780                1785                1790

Asn Leu Trp Ile Pro Leu Ser Glu Asn His Asp Ile Trp Ile Lys Thr
        1795                1800                1805

Leu Thr Cys Ala Phe Leu Asp Ser Gly Gly Thr Lys Cys Glu Ile Leu
    1810                1815                1820

Gln Leu Leu Lys Pro Met Cys Glu Val Lys Thr Asp Phe Cys Gln Thr
1825                1830                1835                1840

Val Leu Pro Tyr Leu Ile His Asp Ile Leu Leu Gln Asp Thr Asn Glu
        1845                1850                1855

Ser Trp Arg Asn Leu Leu Ser Thr His Val Gln Gly Phe Phe Thr Ser
            1860                1865                1870

Cys Leu Arg His Phe Ser Gln Thr Ser Arg Ser Thr Thr Pro Ala Asn
        1875                1880                1885

Leu Asp Ser Glu Ser Glu His Phe Phe Arg Cys Cys Leu Asp Lys Lys
    1890                1895                1900

```
Ser Gln Arg Thr Met Leu Ala Val Val Asp Tyr Met Arg Arg Gln Lys
1905                1910                1915                1920

Arg Pro Ser Ser Gly Thr Ile Phe Asn Asp Ala Phe Trp Leu Asp Leu
            1925                1930                1935

Asn Tyr Leu Glu Val Ala Lys Val Ala Gln Ser Cys Ala Ala His Phe
            1940                1945                1950

Thr Ala Leu Leu Tyr Ala Glu Ile Tyr Ala Asp Lys Lys Ser Met Asp
            1955                1960                1965

Asp Gln Glu Lys Arg Ser Leu Ala Phe Glu Glu Gly Ser Gln Ser Thr
            1970                1975                1980

Thr Ile Ser Ser Leu Ser Glu Lys Ser Lys Glu Glu Thr Gly Ile Ser
1985                1990                1995                2000

Leu Gln Asp Leu Leu Leu Glu Ile Tyr Arg Ser Ile Gly Glu Pro Asp
            2005                2010                2015

Ser Leu Tyr Gly Cys Gly Gly Lys Met Leu Gln Pro Ile Thr Arg
            2020                2025                2030

Leu Arg Thr Tyr Glu His Glu Ala Met Trp Gly Lys Ala Leu Val Thr
            2035                2040                2045

Tyr Asp Leu Glu Thr Ala Ile Pro Ser Ser Thr Arg Gln Ala Gly Ile
            2050                2055                2060

Ile Gln Ala Leu Gln Asn Leu Gly Leu Cys His Ile Leu Ser Val Tyr
2065                2070                2075                2080

Leu Lys Gly Leu Asp Tyr Glu Asn Lys Asp Trp Cys Pro Glu Leu Glu
            2085                2090                2095

Glu Leu His Tyr Gln Ala Ala Trp Arg Asn Met Gln Trp Asp His Cys
            2100                2105                2110

Thr Ser Val Ser Lys Glu Val Glu Gly Thr Ser Tyr His Glu Ser Leu
            2115                2120                2125

Tyr Asn Ala Leu Gln Ser Leu Arg Asp Arg Glu Phe Ser Thr Phe Tyr
            2130                2135                2140

Glu Ser Leu Lys Tyr Ala Arg Val Lys Glu Val Glu Glu Met Cys Lys
2145                2150                2155                2160

Arg Ser Leu Glu Ser Val Tyr Ser Leu Tyr Pro Thr Leu Ser Arg Leu
            2165                2170                2175

Gln Ala Ile Gly Glu Leu Glu Ser Ile Gly Glu Leu Phe Ser Arg Ser
            2180                2185                2190

Val Thr His Arg Gln Leu Ser Glu Val Tyr Ile Lys Trp Gln Lys His
            2195                2200                2205

Ser Gln Leu Leu Lys Asp Ser Asp Phe Ser Phe Gln Glu Pro Ile Met
            2210                2215                2220

Ala Leu Arg Thr Val Ile Leu Glu Ile Leu Met Glu Lys Glu Met Asp
2225                2230                2235                2240

Asn Ser Gln Arg Glu Cys Ile Lys Asp Ile Leu Thr Lys His Leu Val
            2245                2250                2255

Glu Leu Ser Ile Leu Ala Arg Thr Phe Lys Asn Thr Gln Leu Pro Glu
            2260                2265                2270

Arg Ala Ile Phe Gln Ile Lys Gln Tyr Asn Ser Val Ser Cys Gly Val
            2275                2280                2285

Ser Glu Trp Gln Leu Glu Glu Ala Gln Val Phe Trp Ala Lys Lys Glu
            2290                2295                2300

Gln Ser Leu Ala Leu Ser Ile Leu Lys Gln Met Ile Lys Lys Leu Asp
2305                2310                2315                2320

Ala Ser Cys Ala Ala Asn Asn Pro Ser Leu Lys Leu Thr Tyr Thr Glu
```

-continued

```
                    2325                2330                2335
    Cys Leu Arg Val Cys Gly Asn Trp Leu Ala Glu Thr Cys Leu Glu Asn
                2340                2345                2350
    Pro Ala Val Ile Met Gln Thr Tyr Leu Glu Lys Ala Val Glu Val Ala
                2355                2360                2365
    Gly Asn Tyr Asp Gly Glu Ser Ser Asp Leu Arg Asn Gly Lys Met
            2370                2375                2380
    Lys Ala Phe Leu Ser Leu Ala Arg Phe Ser Asp Thr Gln Tyr Gln Arg
2385                2390                2395                2400
    Ile Glu Asn Tyr Met Lys Ser Ser Glu Phe Glu Asn Lys Gln Ala Leu
                2405                2410                2415
    Leu Lys Arg Ala Lys Glu Glu Val Gly Leu Leu Arg Glu His Lys Ile
                2420                2425                2430
    Gln Thr Asn Arg Tyr Thr Val Lys Val Gln Arg Glu Leu Glu Leu Asp
                2435                2440                2445
    Glu Leu Ala Leu Arg Ala Leu Lys Glu Asp Arg Lys Arg Phe Leu Cys
                2450                2455                2460
    Lys Ala Val Glu Asn Tyr Ile Asn Cys Leu Leu Ser Gly Glu Glu His
2465                2470                2475                2480
    Asp Met Trp Val Phe Arg Leu Cys Ser Leu Trp Leu Glu Asn Ser Gly
                2485                2490                2495
    Val Ser Glu Val Asn Gly Met Met Lys Arg Asp Gly Met Lys Ile Pro
                2500                2505                2510
    Thr Tyr Lys Phe Leu Pro Leu Met Tyr Gln Leu Ala Ala Arg Met Gly
                2515                2520                2525
    Thr Lys Met Met Gly Gly Leu Gly Phe His Glu Val Leu Asn Asn Leu
                2530                2535                2540
    Ile Ser Arg Ile Ser Met Asp His Pro His His Thr Leu Phe Ile Ile
2545                2550                2555                2560
    Leu Ala Leu Ala Asn Ala Asn Arg Asp Glu Phe Leu Thr Lys Pro Glu
                2565                2570                2575
    Val Ala Arg Arg Ser Arg Ile Thr Lys Asn Val Pro Lys Gln Ser Ser
                2580                2585                2590
    Gln Leu Asp Glu Asp Arg Thr Glu Ala Ala Asn Arg Ile Ile Cys Thr
                2595                2600                2605
    Ile Arg Ser Arg Arg Pro Gln Met Val Arg Ser Val Glu Ala Leu Cys
                2610                2615                2620
    Asp Ala Tyr Ile Ile Leu Ala Asn Leu Asp Ala Thr Gln Trp Lys Thr
2625                2630                2635                2640
    Gln Arg Lys Gly Ile Asn Ile Pro Ala Asp Gln Pro Ile Thr Lys Leu
                2645                2650                2655
    Lys Asn Leu Glu Asp Val Val Val Pro Thr Met Glu Ile Lys Val Asp
                2660                2665                2670
    His Thr Gly Glu Tyr Gly Asn Leu Val Thr Ile Gln Ser Phe Lys Ala
                2675                2680                2685
    Glu Phe Arg Leu Ala Gly Gly Val Asn Leu Pro Lys Ile Ile Asp Cys
                2690                2695                2700
    Val Gly Ser Asp Gly Lys Glu Arg Arg Gln Leu Val Lys Gly Arg Asp
2705                2710                2715                2720
    Asp Leu Arg Gln Asp Ala Val Met Gln Gln Val Phe Gln Met Cys Asn
                2725                2730                2735
    Thr Leu Leu Gln Arg Asn Thr Glu Thr Arg Lys Arg Lys Leu Thr Ile
                2740                2745                2750
```

```
Cys Thr Tyr Lys Val Val Pro Leu Ser Gln Arg Ser Gly Val Leu Glu
    2755                2760                2765

Trp Cys Thr Gly Thr Val Pro Ile Gly Glu Phe Leu Val Asn Asn Glu
    2770                2775                2780

Asp Gly Ala His Lys Arg Tyr Arg Pro Asn Asp Phe Ser Ala Phe Gln
2785                2790                2795                2800

Cys Gln Lys Lys Met Met Glu Val Gln Lys Lys Ser Phe Glu Glu Lys
        2805                2810                2815

Tyr Glu Val Phe Met Asp Val Cys Gln Asn Phe Gln Pro Val Phe Arg
    2820                2825                2830

Tyr Phe Cys Met Glu Lys Phe Leu Asp Pro Ala Ile Trp Phe Glu Lys
    2835                2840                2845

Arg Leu Ala Tyr Thr Arg Ser Val Ala Thr Ser Ser Ile Val Gly Tyr
    2850                2855                2860

Ile Leu Gly Leu Gly Asp Arg His Val Gln Asn Ile Leu Ile Asn Glu
2865                2870                2875                2880

Gln Ser Ala Glu Leu Val His Ile Asp Leu Gly Val Ala Phe Glu Gln
        2885                2890                2895

Gly Lys Ile Leu Pro Thr Pro Glu Thr Val Pro Phe Arg Leu Thr Arg
    2900                2905                2910

Asp Ile Val Asp Gly Met Gly Ile Thr Gly Val Glu Gly Val Phe Arg
    2915                2920                2925

Arg Cys Cys Glu Lys Thr Met Glu Val Met Arg Asn Ser Gln Glu Thr
    2930                2935                2940

Leu Leu Thr Ile Val Glu Val Leu Leu Tyr Asp Pro Leu Phe Asp Trp
2945                2950                2955                2960

Thr Met Asn Pro Leu Lys Ala Leu Tyr Leu Gln Gln Arg Pro Glu Asp
        2965                2970                2975

Glu Thr Glu Leu His Pro Thr Leu Asn Ala Asp Asp Gln Glu Cys Lys
    2980                2985                2990

Arg Asn Leu Ser Asp Ile Asp Gln Ser Phe Asp Lys Val Ala Glu Arg
    2995                3000                3005

Val Leu Met Arg Leu Gln Glu Lys Leu Lys Gly Val Glu Glu Gly Thr
    3010                3015                3020

Val Leu Ser Val Gly Gly Gln Val Asn Leu Leu Ile Gln Gln Ala Ile
3025                3030                3035                3040

Asp Pro Lys Asn Leu Ser Arg Leu Phe Pro Gly Trp Lys Ala Trp Val
        3045                3050                3055

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

ACGTTACATG AGCCAG                                                        16

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear
```

(ii) MOLECULE TYPE: Other (xi) SEQUENCE DESCRIPTION: SEQ ID NO:4:

TCCAAATGTC ATGATTTTCA C                                                     21

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:5:

CTGGCCTATC TACAGC                                                           16

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:6:

CAACCTGCTA AGTGTGGGAT                                                       20

(2) INFORMATION FOR SEQ ID NO:7:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

CAGTGGGACC ATTGC                                                            15

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

TTCTGACCAT CTGAGGTCTC C                                                     21

(2) INFORMATION FOR SEQ ID NO:9:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:9:

GATCACCCCA TCACA          15

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:10:

TCACACCCAA GCTTTCCATC          20

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:11:

GGATCCTAAT ACGACTCACT ATAGGAACAG ACCACCATG          39

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:12:

GAAGTTGAGA AATTTAAGC          19

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:13:

AATGCAACTT CCGTAAGGC          19

(2) INFORMATION FOR SEQ ID NO:14:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:14:

GCAGATATCT GT          12

(2) INFORMATION FOR SEQ ID NO:15:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: Other (xi) SEQUENCE DESCRIPTION: SEQ ID NO:15:

GTAGGTTCTA GCGTGCTAGA                                           20

(2) INFORMATION FOR SEQ ID NO:16:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:16:

AATGACATTG CAGATATTT                                            19

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:17:

TCAGTGCTCT GACTGGCACT                                           20

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:18:

GCTTACTTGG AGCCATAATT C                                         21

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:19:

TGAAGGTCTG CAGGCTGAC                                            19

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:20:

TGGGAAAAGA CTTTCCTGTA AA                                            22

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:21:

CTATTGATTG ACTCTGCAGC C                                             21

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:22:

CTCTATGCAG AAATCTATGC AG                                            22

(2) INFORMATION FOR SEQ ID NO:23:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:23:

ATACCCTTAT TGAGACAATG CC                                            22

(2) INFORMATION FOR SEQ ID NO:24:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:24:

GTATTCAGGA GCTTC                                                    15

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:25:

```
ATGGCATCTG TACAGTGTCT                                                       20

(2) INFORMATION FOR SEQ ID NO:26:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:26:

CAGAACTGTA TTTCAGAATC AT                                                    22

(2) INFORMATION FOR SEQ ID NO:27:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:27:

ACATAACTCC TTCATAAACA GA                                                    22

(2) INFORMATION FOR SEQ ID NO:28:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:28:

AGTTGGGTAC AGTCATGGTA                                                       20

(2) INFORMATION FOR SEQ ID NO:29:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:29:

GAAAAGATGA AGCATATTCA TG                                                    22

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:30:

TTACTTGCTT AGATGTGAGA                                                       20

(2) INFORMATION FOR SEQ ID NO:31:
```

```
        (i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:31:

ATATGTTGGA ATCTTCATTC CG                                                 22

(2) INFORMATION FOR SEQ ID NO:32:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:32:

AAGCAAAATG AAAAATATGG                                                    20

(2) INFORMATION FOR SEQ ID NO:33:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: Other (xi) SEQUENCE DESCRIPTION: SEQ ID NO:33:

AAGTGTGATG GGGGTGA                                                       17
```